US008388935B2

(12) United States Patent  
Lin et al.

(10) Patent No.: US 8,388,935 B2
(45) Date of Patent: Mar. 5, 2013

(54) METHODS OF DIAGNOSING AND TREATING SMALL INTESTINAL BACTERIAL OVERGROWTH (SIBO) AND SIBO-RELATED CONDITIONS

(75) Inventors: Henry C. Lin, Albuquerque, NM (US); Mark Pimentel, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/315,671

(22) Filed: Dec. 9, 2011

(65) Prior Publication Data

US 2012/0263790 A1 Oct. 18, 2012

Related U.S. Application Data

(60) Continuation of application No. 12/768,531, filed on Apr. 27, 2010, now Pat. No. 8,110,177, which is a continuation of application No. 11/348,995, filed on Feb. 7, 2006, now Pat. No. 7,736,622, which is a division of application No. 09/837,797, filed on Apr. 17, 2001, now Pat. No. 7,048,906, which is a continuation-in-part of application No. 09/374,142, filed on Aug. 11, 1999, now Pat. No. 6,861,053, and a continuation-in-part of application No. 09/374,143, filed on Aug. 11, 1999, now Pat. No. 6,562,629, and a continuation-in-part of application No. 09/546,119, filed on Apr. 10, 2000, now Pat. No. 6,558,708.

(51) Int. Cl.
*A61K 49/00* (2006.01)
*A61K 35/00* (2006.01)
*A61K 45/00* (2006.01)

(52) U.S. Cl. ....... 424/9.2; 424/9.1; 424/116; 424/278.1; 424/439; 426/5; 426/71; 426/658; 426/800; 435/5; 435/29

(58) Field of Classification Search .................. 424/9.1, 424/9.2, 116, 278.1, 439; 426/5, 71, 658, 426/800, 801; 435/4, 29
See application file for complete search history.

(56) References Cited

U.S. PATENT DOCUMENTS

| | | | |
|---|---|---|---|
| 4,160,452 A | 7/1979 | Theeuwes | |
| 4,179,438 A | 12/1979 | Marchi et al. | |
| 4,183,960 A | 1/1980 | Asher et al. | |
| 4,193,985 A | 3/1980 | Bechgaard et al. | |
| 4,200,574 A | 4/1980 | Marchi et al. | |
| 4,256,108 A | 3/1981 | Theeuwes | |
| 4,265,874 A | 5/1981 | Bonsen et al. | |
| 4,341,785 A | 7/1982 | Marchi et al. | |
| 4,386,079 A | 5/1983 | Lahti | |
| 4,530,838 A | 7/1985 | Evans et al. | |
| 4,557,866 A | 12/1985 | Cannata et al. | |
| 4,572,833 A | 2/1986 | Pedersen et al. | |
| 4,611,011 A | 9/1986 | Yelnosky et al. | |
| 4,673,680 A | 6/1987 | Pendleton | |
| 4,690,822 A | 9/1987 | Uemura et al. |
| 4,701,457 A | 10/1987 | Yelnosky et al. |
| 4,863,744 A | 9/1989 | Urquhart et al. |
| 4,970,207 A | 11/1990 | Sato et al. |
| 4,987,136 A | 1/1991 | Kreek et al. |
| 4,990,617 A | 2/1991 | Boswell et al. |
| 5,041,431 A | 8/1991 | Halskov |
| 5,063,245 A | 11/1991 | Abreu et al. |
| 5,064,858 A | 11/1991 | Sapse |
| 5,120,306 A | 6/1992 | Gosselin |
| 5,219,871 A | 6/1993 | Cross et al. |
| 5,225,352 A | 7/1993 | Zanetta et al. |
| 5,225,407 A | 7/1993 | Oakley et al. |
| 5,236,901 A | 8/1993 | Burks et al. |
| 5,308,620 A | 5/1994 | Yen |
| 5,314,904 A | 5/1994 | Egidio et al. |
| 5,322,697 A | 6/1994 | Meyer |
| 5,352,679 A | 10/1994 | Ferrieri et al. |
| 5,354,757 A | 10/1994 | Flynn et al. |
| 5,362,756 A | 11/1994 | Riviere et al. |
| 5,380,522 A | 1/1995 | Day |
| 5,411,751 A | 5/1995 | Crissinger et al. |
| 5,426,028 A | 6/1995 | Levy et al. |
| 5,434,174 A | 7/1995 | Gidda et al. |
| 5,443,826 A | 8/1995 | Borody |
| 5,453,428 A | 9/1995 | Kaminski |
| 5,519,014 A | 5/1996 | Borody |
| 5,538,856 A | 7/1996 | Levy et al. |
| 5,547,961 A | 8/1996 | Ohta et al. |
| 5,550,132 A | 8/1996 | Benson et al. |
| 5,574,010 A | 11/1996 | McFadden |
| 5,589,168 A | 12/1996 | Allen et al. |
| 5,599,795 A | 2/1997 | McCann et al. |
| 5,604,203 A | 2/1997 | Balasubramaniam |
| 5,612,366 A | 3/1997 | Becker et al. |

(Continued)

FOREIGN PATENT DOCUMENTS

| | | |
|---|---|---|
| AU | 2002256254 | 10/2002 |
| AU | 2007201246 | 4/2007 |

(Continued)

OTHER PUBLICATIONS

Alvisi et al., "Treatment of Secretory Diarrhoeas: A Double-Blind Trial of the Effectiveness of Rifaximin (L105) and Neomycin," Clinical Trials Journal, (1984), 21(4):215-223.

(Continued)

*Primary Examiner* — Rodney P. Swartz
(74) *Attorney, Agent, or Firm* — Linda B. Huber; Nixon Peabody LLP

(57) ABSTRACT

Disclosed is a method of treating small intestinal bacterial overgrowth (SIBO) or a SIBO-caused condition in a human subject. SIBO-caused conditions include irritable bowel syndrome, fibromyalgia, chronic pelvic pain syndrome, chronic fatigue syndrome, depression, impaired mentation, impaired memory, halitosis, tinnitus, sugar craving, autism, attention deficit/hyperactivity disorder, drug sensitivity, an autoimmune disease, and Crohn's disease. Also disclosed are a method of screening for the abnormally likely presence of SIBO in a human subject and a method of detecting SIBO in a human subject. A method of determining the relative severity of SIBO or a SIBO-caused condition in a human subject, in whom small intestinal bacterial overgrowth (SIBO) has been detected, is also disclosed.

16 Claims, 13 Drawing Sheets

U.S. PATENT DOCUMENTS

| | | |
|---|---|---|
| 5,616,311 A | 4/1997 | Yen |
| 5,627,200 A | 5/1997 | Kreutter et al. |
| 5,645,997 A | 7/1997 | Kline et al. |
| 5,648,355 A | 7/1997 | Theoharides |
| 5,648,359 A | 7/1997 | Ohashi et al. |
| 5,660,828 A | 8/1997 | Rodriquez et al. |
| 5,668,143 A | 9/1997 | Ku et al. |
| 5,677,326 A | 10/1997 | Tauchiya et al. |
| 5,679,684 A | 10/1997 | Benson et al. |
| 5,684,017 A | 11/1997 | Harrison et al. |
| 5,691,343 A | 11/1997 | Sandborn |
| 5,696,093 A | 12/1997 | Tseng et al. |
| 5,703,100 A | 12/1997 | McDonald et al. |
| 5,707,642 A | 1/1998 | Yue |
| 5,716,643 A | 2/1998 | Yen |
| 5,725,804 A | 3/1998 | Yen |
| 5,726,187 A | 3/1998 | Gaster et al. |
| 5,728,380 A | 3/1998 | Allen et al. |
| 5,736,560 A | 4/1998 | Cosford et al. |
| 5,753,218 A | 5/1998 | Smith et al. |
| 5,753,253 A | 5/1998 | Meyer |
| 5,759,546 A | 6/1998 | Weinberg et al. |
| 5,759,565 A | 6/1998 | Azria et al. |
| 5,760,032 A | 6/1998 | Kitajima et al. |
| 5,776,524 A | 7/1998 | Reinhart |
| 5,780,026 A | 7/1998 | Yoshii et al. |
| 5,821,259 A | 10/1998 | Theoharides |
| 5,830,668 A | 11/1998 | Mordechai et al. |
| 5,833,987 A | 11/1998 | Noelle et al. |
| 5,834,215 A | 11/1998 | Garry et al. |
| 5,846,933 A | 12/1998 | Komgold et al. |
| 5,849,708 A | 12/1998 | Maratos-Flier |
| 5,852,041 A | 12/1998 | Cosford et al. |
| 5,858,403 A | 1/1999 | Borody et al. |
| 5,861,398 A | 1/1999 | Rabinovich et al. |
| 5,863,529 A | 1/1999 | Rodriguez |
| 5,863,552 A | 1/1999 | Yue |
| 5,869,262 A | 2/1999 | Gallatin et al. |
| 5,886,002 A | 3/1999 | Ferrari et al. |
| 5,912,227 A | 6/1999 | Croom, Jr. et al. |
| 5,916,869 A | 6/1999 | Croom, Jr. et al. |
| 5,945,033 A | 8/1999 | Yen |
| 5,968,741 A | 10/1999 | Plevy et al. |
| 5,968,748 A | 10/1999 | Bennett et al. |
| 5,977,175 A | 11/1999 | Lin |
| 5,980,945 A | 11/1999 | Ruiz |
| 6,013,285 A | 1/2000 | Yen |
| 6,013,622 A | 1/2000 | Bruno et al. |
| 6,013,633 A | 1/2000 | Balasubramanium et al. |
| 6,017,544 A | 1/2000 | Srivastava |
| 6,017,879 A | 1/2000 | Mutter et al. |
| 6,040,188 A | 3/2000 | Holman |
| 6,046,167 A | 4/2000 | Balasubramaniam |
| 6,140,355 A | 10/2000 | Egidio et al. |
| RE37,020 E | 1/2001 | Lin et al. |
| 6,191,102 B1 | 2/2001 | DiMarchi et al. |
| 6,235,718 B1 | 5/2001 | Balasubramanium et al. |
| 6,264,913 B1 | 7/2001 | Wagner |
| 6,267,988 B1 | 7/2001 | Meyer |
| 6,326,364 B1 | 12/2001 | Lin et al. |
| 6,391,343 B1 | 5/2002 | Yen |
| 6,558,708 B1 | 5/2003 | Lin |
| 6,562,629 B1 | 5/2003 | Lin et al. |
| 6,583,111 B1 | 6/2003 | DiMarchi et al. |
| 6,737,408 B1 | 5/2004 | Balasubramanium et al. |
| 6,805,852 B2 | 10/2004 | Lin et al. |
| 6,861,053 B1 | 3/2005 | Lin et al. |
| 7,045,620 B2 | 5/2006 | Viscomi et al. |
| 7,048,906 B2 | 5/2006 | Lin et al. |
| 7,056,686 B2 | 6/2006 | Lin et al. |
| 7,081,239 B2 | 7/2006 | Lin |
| 7,244,412 B2 | 7/2007 | Lin |
| 7,452,857 B2 | 11/2008 | Lin et al. |
| 7,585,838 B2 | 9/2009 | Lin et al. |
| 7,605,240 B2 | 10/2009 | Lin et al. |
| 7,608,245 B2 | 10/2009 | Lin |
| 7,615,207 B2 | 11/2009 | Lin |
| 7,718,608 B2 | 5/2010 | Lin et al. |
| 7,736,622 B2 | 6/2010 | Lin et al. |
| 7,935,799 B2 | 5/2011 | Lin et al. |
| 8,197,805 B2 | 6/2012 | Lin et al. |
| 2002/0018809 A1 | 2/2002 | Stoll |
| 2002/0068097 A1 | 6/2002 | Basu |
| 2003/0050308 A1 | 3/2003 | Brunner et al. |
| 2003/0124566 A1 | 7/2003 | Kong et al. |
| 2003/0152919 A1 | 8/2003 | Roelens et al. |
| 2003/0185754 A1 | 10/2003 | Cohen et al. |
| 2003/0215421 A1 | 11/2003 | McDonald et al. |
| 2004/0228846 A1 | 11/2004 | Pang et al. |
| 2005/0272754 A1 | 12/2005 | Viscomi et al. |
| 2006/0193871 A1 | 8/2006 | Lin |
| 2010/0209507 A1 | 8/2010 | Lin et al. |
| 2011/0171232 A1 | 7/2011 | Lin et al. |

FOREIGN PATENT DOCUMENTS

| | | |
|---|---|---|
| BE | 896241 A1 | 7/1983 |
| CN | 1099619 A | 3/1995 |
| EP | 0161534 | 11/1985 |
| EP | 0200902 | 11/1986 |
| EP | 0349949 | 1/1990 |
| EP | 0539319 | 4/1993 |
| EP | 1180367 | 2/2002 |
| EP | 1288224 | 3/2003 |
| EP | 0678018 | 4/2003 |
| EP | 1051194 | 5/2003 |
| EP | 1466610 | 10/2004 |
| EP | 1288223 | 12/2004 |
| EP | 1557421 | 7/2005 |
| EP | 1698630 | 9/2006 |
| EP | 1200828 | 10/2007 |
| EP | 2256498 | 12/2010 |
| EP | 2261664 | 12/2010 |
| EP | 2261665 | 12/2010 |
| EP | 2267445 | 12/2010 |
| EP | 2305213 | 4/2011 |
| FR | 2557453 A1 | 7/1985 |
| FR | 2769915 | 4/1999 |
| GB | 979244 A | 1/1965 |
| GB | 2181347 A | 4/1987 |
| JP | 2009102401 | 5/2009 |
| WO | WO 8502840 | 7/1985 |
| WO | WO 9403380 | 2/1994 |
| WO | WO 9422467 | 10/1994 |
| WO | WO 9618374 | 6/1996 |
| WO | WO 9636330 | 11/1996 |
| WO | WO 9820885 | 5/1998 |
| WO | WO 9836330 | 8/1998 |
| WO | WO 9846997 | 10/1998 |
| WO | WO 9856397 | 12/1998 |
| WO | WO 9924613 | 5/1999 |
| WO | WO 9926632 | 6/1999 |
| WO | WO 0047219 | 8/2000 |
| WO | WO 0064453 | 11/2000 |
| WO | WO 0111077 | 2/2001 |
| WO | WO 0111334 | 2/2001 |
| WO | WO 0176631 | 10/2001 |
| WO | WO 0247712 | 6/2002 |
| WO | WO 02083926 | 10/2002 |
| WO | WO 03026591 | 4/2003 |
| WO | WO 03057235 | 7/2003 |
| WO | WO 2005044823 | 5/2005 |
| WO | WO 2006094662 | 9/2006 |
| WO | WO 2006094737 | 9/2006 |

OTHER PUBLICATIONS

Anand et al., "Does Non-Dysenteric Intestinal Amoebiasis Exist?," Lancet, vol. 349, No. 9045 (Jan. 11, 1997), pp. 89-92.

Anderson, Beth W., et al., "Influence of Infusate Viscosity on Intestinal Absorption in the Rat," Gastroenterology, vol. 97, pp. 938-943 (Oct. 1989).

Attar et al., "Efficacy of Two Antibiotics and a Probiotic in the Treatment of Small Inestinal Bacterial Overgrowth," Gastroenterology, (1996), 110(4), p. A310, Meeting Abstract.

Asarian, L., et al., "Intracerebroventricular glucagon-like peptide-1 (7-36) amide inhibits sham feeding in rats without eliciting satiety," Physiol Behav, 64(3):367-72 (Jun. 1, 1998). Abstract Only.

Bagnol., D. et al., "Cellular localization and distribution of the cloned mu and kappa opioid receptors in rat gastrointestinal tract" Neuroscience, 81(2):579-91 (Nov. 1997). Abstract Only.

Banwell et al., "Small Intestinal Bacterial Overgrowth Syndrome," Gastroenterology, (1981), 80(4), pp. 834-845.

Barnes, R.M.R. et al., "Serum Antibodies Reative with *Saccharomyces cerevisiae* in Inflammatory Bowel Disease: Is IgA Antibody a Marker for Crohn's Disease?," Int Arch Allergy Appl Immunol, 92:9-15 (1990). XP-000979650.

Bartlett, J.G., "Treatment of antibiotic-associated Pseudomembranous colitis," Rev Infect Dis 1:S235-41 (6 Suppl) (Mar.-Apr. 1984) Abstract Only.

Baskin, D. G. et al., "Leptin sensitive neurons in the hypothalamus," Horm Metab Res, 31(5):345-50 (May 1999). Abstract Only.

Bergstrom, J., et al. "Mechanisms of uremic suppression of appetite," J. Ren Nutr, 9(3):129-32 (Jul. 1999). Abstract Only.

Bilchik, A. J. et al., "Peptide YY augments postprandial small intestinal absorbtion in the conscious dog," Am J. Surg 167(6):570-4 (Jun. 1994). Abstract Only.

Blevins, J. E. et al., "Brain regions where cholecystokinin suppresses feeding in rats," Brain Res. 860(1-2):1-10 (Mar. 31, 2000). Abstract Only.

Boero, M. et al., "Treatment for colitis caused by *Clostridium difficile*: Results of a randomized open study of rifaximine vs. vancomycin," Microbiologia Medica, 5(2): 74-77 (1990).

Booyse, Francois M. et al., "Effects of Chronic Oral Consumption of Nicotine on the Rabbit Aortic Endothelium," Am J Patho, vol. 102, No. 2, pp. 229-238 (1981).

Bozdech, J.M., et al., "Diagnosis of Crohn's disease," Hepatogastroenterology, 37(1):8-17 (Feb. 1990) Review; Abstract.

Brown, Michael S., "The Hyperlipoproteinemias and Other Disorders of Lipid Metabolism," Chapter 344 on Disorders of lipid metabolism, Harrison's Principles of Internal Medicine, 13th sup. Ed. pp. 2058-2069 (1994).

Brown, N. J. et al., "The effect of a 5-HT3-antagonist on the ileal brake mechanism in the rat," J. Pharm Pharmacol, 43(7):517-9 (Jul. 1991). Abstract Only.

Brown, N. J. et al., "Granisetron and ondansetron: effects on the ileal brake mechanism in the rat," J. Pharm Pharmacol 45(6):521-4 (Jun. 1993). Abstract Only.

Brown, N. J. et al., "The effect of an opiate receptor antagonist on the ileal brake mechanism in the rat," Pharmacology, 47(4):230-6 (Oct. 1993). Abstract Only.

Brown, N. J., et al. "Characteristics of lipid substances activating the ileal brake in the rat," Gut, 31(10):1126-1129 (Oct. 1990). XP 00613253.

Buhner, Sabine et al., "Characteristics of Postprandial Duodenal Motor Patterns in Dogs," Digestive Diseases and Sciences, vol. 34, No. 12, pp. 1873-1881 (Dec. 1989).

Bushnik, T. "Influence of bombesin on threshold for feeding and reward in the rat," Acta Neurobiol Exp (Warsz), 59(4):295-302 (1999). Abstract Only.

Cammack, J. et al., "Effect of prolonged exercise on the passage of a solid metal through the stomach and small intestine," Gut, vol. 23, pp. 957-961 (1982).

Carlson, G. M. et al., "Effects of Nicotine on Gastric antral and Duodenal Contractile Activity in the Dog," The Journal of Pharmacology and Experimental Therapeutics, vol. 172, No. 2, pp. 367-376 (1970).

Certo, M. et al., "Small-intestine bacterial contamination syndrome in subjects without "primary" intestinal pathologies: A frequent cause of chronic diarrhea," Nuove Prospettive in Terapia (New Prospects in Therapy), 1-11 (Jul. 1996).

Chang, T.W., et al., "Bacitracin treatment of antibiotic-associated colitis and diarrhea caused by *Clostridium difficile* toxin," Gastroenterology, 78(6):1584-6, (Jun. 1980) Abstract Only.

Chen, J. X. et al., "Guinea pig 5-HT transporter: cloning, expression, distribution, and function in intestinal sensory reception," Am. J. Physiol. 275 (3 Pt 1):G433-48 (Sep. 1998). Abstract Only.

Cherbut, C et al., "Effects of short-chain fatty acids on gastrointestinal motility," Scand J. Gasteroenterol Suppl, 222:58-61 (1997). Abstract Only.

Christophe, J. "Is there appetite after GLP-1 and PACAP?," Ann N Y Acad Sci, 865:323-35 (Dec. 11, 1998). Abstract Only.

Cohn, Clarence, "Feeding patterns and some aspects of cholesterol metabolism," Federation Proceedings, vol. 23, pp. 76-81 (1964).

Cohn, Clarence, "Meal-Eating, Nibbling, and Body Metabolism," The Journal of The American Dietetic Association, vol. 38, pp. 433-436 (May 1961).

Collins, S. M. et al., "Endogenous cholecystokinin and intestinal satiety," Am J. Physiol, 249 (6 Pt 2):R667-71 (Dec. 1985). Abstract Only.

Corazza, G.R. et al., "Non-absorbable antibiotics and small bowel bacterial overgrowth," Ital J Gasteroenterol, 24 Suppl 2:4-9 (1992).

Corazza, G.R. et al., "Treatment of Small Intestine Bacterial Overgrowth with Rifaximin, a Non-absorbable Rifamycin," The Journal of International Medical Research, 16: 312-316 (1998).

Cross-Mellor, S. K. et al., "Repeated injections of lipopolysaccharide attenuate the satiety effects of cholecystokinin," Neuroreport, 10(18):3847-51 (Dec. 1999). Abstract Only.

Culpepper-Morgan, J. A. et al., "Treatment of opioid-induced constipation with oral naloxone: a pilot study," Clin Pharmacol Ther, 52(1):90-5 (Jul. 1992). Abstract Only.

Cunningham, K. M. et al., "Gastrointestinal adaptation to diets of differing fat composition in human volunteers," Gut, vol. 32, pp. 483-486 (1991).

Cuoco et al., Letter to Am. J. of Gastroenterology, 96(7): 2281-82 (2001).

Darroch, C. J. et al., "Circulating antibodies to *Saccharomyces cerevisiae* (bakers'/brewers'yeast) in gastrointestinal disease," J. Clin Pathol, 52:47-53 (1999). XP-000980104.

Davis, Stanley S., et al., "The Effect of Density on the Gastric Emptying of Single- and Multiple-Unit Dosage Forms," Pharmaceutical Research, vol. 3, No. 4, pp. 208-213 (1986).

Dellert, S.F., et al., "The 13C-xylose breath test for the diagnosis of small bowel bacterial overgrowth in children," J Pediatr Gastroenterol Nutr 25(2):153-8 (Aug. 1997) Abstract Only.

Delin, et al., "Comparison of Gamma Camera and Withdrawal Methods for the Measurement of Gastric Emptying," Scand. J. Gastroent, 13:867-872 (1978).

Distefano, M. et al., "Rifaximin versus chlortetracycline in the short-term treatment of small intestinal bacterial overgrowth," Aliment Pharmacol Ther, 14: 551-556 (2000).

Dobson, Clair, L., et al., "The Effect of Oleic Acid on the Human Ileal Brake and Its Implications for Small Intestinal Transit of Tablet Formulations," Pharmaclinical Research, vol. 16, No. 1, 1999, pp. 92-96 (1999).

Dreznik, Zeev, MD, et al., "Effect of Ileal Oleate on Interdigestive Intestinal Motility of the Dog," Digestive Disease and Sciences, vol. 39, No. 7, pp. 1511-1518 (Jul. 1994).

Drossman, Douglas A., "Treatment for Bacterial Overgrowth in the Irritable Bowel Syndrome," Annals of Internal Medicine, (Oct. 17, 2006), 145(8):626-628.

Drossman, D.A., et al., "Furthur validation of the IBS-QOL: a disease-specific quality-of-life questionnaire," Am J Gastroenterol 95(4):999-1007 (Apr. 2000) Abstract Only.

Eberle-Wang, K. et al., "The CCK-A receptor antagonist devazepide, blocks the anorectic action of CCK but not peripheral serotonin in rats," Pharmacol Biochem Behav, 43(3):943-7 (Nov. 1992). Abstract Only.

Edes, Thomas E., M.D., "Diarrhea in Tube-Fed Patients: Feeding Formula Not Necessarily the Cause," The American Journal of Medicine, vol. 88, pp. 91-93, (Feb. 1990).

Edwards, S. et al., "Peripherally administered 5-hydroxytryptamine elicits the full behavioural sequence of satiety," Physiol Behav, 50(5):1075-7 (Nov. 1991).

El-Salhy, M. et al., "Colonic neuroendocrine peptide levels in patients with chronic idiopathic slow transit constipation," Ups J Med Sci, 103(3):223-30 (1998). Abstract Only.

Erickson, J. C. et al., "Attenuation of the obesity syndrome of ob/ob mice by the loss of neuropeptide Y," Science, 274(5293):1704-7 (Dec. 6, 1996). Abstract Only.

Faris, P. L. et al., "Effect of decreasing afferent vagal activity with ondansetron on symptoms of bulimia nervosa: a randomised, double-blind trial," Lancet, 355(9206):792-7 (Mar. 4, 2000). Abstract Only.

Farthing, M. J., "5-Hydroxytryptamine and 5-hydroxytryptamine-3 receptor antagonists," Scand J. Gastroenterol Suppl, 188:92-100 (1991). Abstract Only.

Farup, P.G., et al., "The symptomatic effect of cisapride in patients with irritable bowel syndrome and constipation," Scand J Gastroenterol 33(2):128-31 (Feb. 1998) Abstract Only.

Ferrara, A. et al., "Intraluminal release of serotonin during the interdigestive migrating complex in the canine small intestine," J. Surg Res, 41(3):308-11 (Sep. 1986). Abstract Only.

Ferrara, A. et al., "Intraluminal release of serotonin, substance P, and gastrin in the canine small intestine," Dig Dis Sci, 32(3):289-94 (Mar. 1987). Abstract Only.

Fine et al., "AGA Technical Review On The Evaluation and Management of Chronic Diarrhea," Gastroenterology, (Jun. 1999), 116(6), pp. 1464-1486.

Fox-Threlkeld, J. A. et al., "Peptide YY stimulates circular muscle contractions of the isolated perfused canine ileum by inhibiting nitric oxide release and enhancing acetylcholine release," Peptides, 14(6):1171-8 (Nov.-Dec. 1993). Abstract Only.

Foxx-Orenstein, A. E. et al., "5-HT4 receptor agonists and delta-opioid receptor antagonists act synergistically to stimulate colonic propulsion," Am J Physiol, 275 (5 Pt 1):G979-83 (Nov. 1998). Abstract Only.

Francis, C.Y., et al., "The irritable bowel severity scoring system: a simple method of monitoring irritable bowel syndrome and its progress," Aliment Pharmacol Ther, 11(2):395-402 (Apr. 1997) Abstract Only.

Frankenfield, David C., et al., "Soy-polysaccharide fiber: effect on diarrhea in tube-fed, head-injured patents," sup. 1-3, Am. J. Clin. Nutr., vol. 50, pp. 533-538 (1989).

Fraser, R., et al., "The Effect of Dietary Fat Load on the Size and Composition of Chylomicrons in Thoracic Dut Lymph," Q. Jl. Exp. Physiol., vol. 53, pp. 390-398, (1968).

Friedman, G. "Diet and the Irritable Bowel Syndrome," Gastroenterology Clinics of N. America, vol. 20, No. 2, pp. 313-324, 1991.

Fu, L. W. et al., "Role of 5-HT3 receptors in activation of abdominal sympathetic C fibre afferents during ischaemia in cats" J. Physiol (Lond), 509 (Pt 3):729-40 (Jun. 15, 1998). Abstract Only.

Fujimiya, M. et al., "Effect of carbachol on the release of peptide YY from isolated vascularly and luminally perfused rat ileum," Peptides, 16(5):939-44 (1995). Abstact Only.

Galligan, J. J., "Electrophysiological studies of 5-hyroxytryptamine receptors on enteric neurons," Behav Brain Res, 73(1-2):199-201 (1996). Abstract Only.

Gershon, M. D. et al., "5-HT receptor subtypes outside the central nervous system. Roles in the physiology of the gut," Neuropsychopharmacology, 3(5-6):385-95 (Oct.-Dec. 1990). Abstract Only.

Gershon, M. D. et al., "Serotonin: its role and receptors in enteric neurotransmission," Adv Exp Med Biol. 294:221-30 (1991). Abstact Only.

Gershon, M.D., "Review article: roles played by 5-hydroxytryptamine in the physiology of the bowel," Aliment Pharmacol Ther, 13 Suppl 2:15-30 (May 1999). Abstact Only.

Giralt, M. et al., "Both afferent and efferent nerves are implicated in cholecytokinin motor actions in the small intestine of the rat," Regul Pept, 81(1-3):73-80 (May 1999). Abstract Only.

Girardet, Roland E., M.D., et al., "Surigcal Techniques for Long-term Study of Thoracic Duct Ciruclation in Dogs," Journal of Surgical Research, vol. 165, pp. 168-175 (1973).

Goodgame et al., "Intensity of Infection In AIDS-Associated Cryptosporidiosis," Journal of Infectious Diseases, (1993), 167:704-709 (abstract).

Gotz, V. et al., "Medical management of antimicrobial-associated diarrhea and colitis," Pharmacotherapy, 2(2):100-9 (Mar.-Apr. 1982) Abstact Only.

Gotz, V., et al., "Prophylaxis against ampicillin-associated diarrhea with a *Lactobacillus* preparation," Am J Hosp Pharm 36(6):754-7 (Jun. 1979) Abstact Only.

Grider, J. R. et al., "5-hydroxytryptamine4 receptor agonists initiate the peristaltic reflex in human, rat, and guinea pig intestine," Gastroenterology, 115(2):370-80 (Aug. 1998). Abstact Only.

Groll, D., et al., "The IBS-36: a new quality of life measure for irritable bowel syndrome," Am J Gastroenterol 97(4):962-71 (Apr. 2002) Abstract Only.

Gruy-Kapral, Christine et al., "Conjugated Bile Acid Replacement Therapy for Short-Bowel Syndrome," Gastroenterology, vol. 116, pp. 15-21 (1999).

Guandalini et al., "*Lactobacillus* GG (L-GG) Improves Intestinal Barrier Function in Children With Crohn's Disease," JPGN, (Jun. 1999), 28(5), p. 556, Meeting Abstract.

Gunn et al., "Management of Irritable Bowel Syndrome," Postgraduate Med. J., vol. 79, pp. 154-158 (2003).

Gwinup, Grant, M.D., et al., "Effect of Nibbling Versus Gorging on Serum Lipids in Man," American Journal of Clinical Nutrition, vol. 13, pp. 209-213 (Oct. 1963).

Hayashi, Hiroshi, et al. "Fat feeding increases size, but not number, of chylomicrons produced by small intestine," The American Physiological Society, Ch. 22, pp. G709-G719 (1990).

Hollopeter, G. et al.. "Response of neuropeptide Y-deficient mice to feeding effectors," Regul Pept, 75-76:383-9 (Sep. 25, 1998). Abstract Only.

Huge, Andreas, et al. "Effects of Enteral Feedback Inhibition on Motility, Luminal Flow, and Absorption of Nutrients in Proximal Gut of Minipigs," Digestive Diseases and Sciences, vol. 40, No. 5, pp. 1024-1034 (May 1995). XP 000613720.

Hughes et al. "Intraventricular Calcitonin Gene-Related Peptide Inhibits Gastric Acid Secretion;" Peptides. vol. 5; p. 665-667; 1984.

Inui, A. "Feeding and body-weight regulation by hypothalamic neuropeptides—mediation of the actions of leptin," Trends Neurosci, 22(2):62-7 (Feb. 1999). Abstract Only.

Irwin, M. Isabel. B.H.Sc., M.Sc., Ph.D, et al. "Frequency and Size of Meals and Serum Lipids, Nitrogen and Mineral Retention, Fat Digestibility, and Urinary Thiamine and Riboflavin in Young Women," Am. J. Clin. Nutr., vol. 20, No. 8, pp. 816-821 (Aug. 1967).

Jackerott, M. et al. "Immunocytochemical localization of the NPY/PYY Y1 receptor in enteric neurons endothelial cells, and endorcine-like cells of the rat intestinal tract," J. Histochem Cytochem 45(12):1643-50 (Dec. 1997). Abstact Only.

Jagannathan, S.N., Ph.D. "Effects of Gormandizing and Semicontinuous Eating of Equicaloric Amounts of Formula-Type High Fat Diets on Plasma Cholesterol and Triglyceride Levels in Human Volunteer Subjects," Am. J. Clin. Nutr., vol. 15, pp. 90-93 (Aug. 1964).

Jenkins, David J.A., M.D., Ph.D., et al. "Nibbling Versus Gorging: Metabolic Advantages of Increased Meal Frequency," New Engl. J. Med., vol. 321, No. 14, pp. 929-934 (Oct. 5, 1989).

Jenkins, P.J., et al. "Severity of coronary atherosclerosis related to lipoprotein concentration," British Medical Journal, vol. 2, pp. 388-391 (1978).

Jin, J. G., et al. "Propulsion in guinea pig colon induced by 5-hdroxytryptamine (HT) via 5-HT4 and 5-HT3 receptors," J. Pharmacol Exp Ther, 288(1):93-7 (1999). Abstract Only.

Keinke, et al. "Mechanical Factors Regulating Gastric Emptying of Viscous Nutrients Meals in Dogs," Q. J. Exp. Physiol., 69:781-795 (1984).

Keinke, Oliver, et al. "Effect of Oleic Acid on Canine Gastroduodenal Motility," Pyloric Diameter and Gastric Emptying, Quarterly Journal of Experimental Physiology, vol. 68, pp. 675-686 (1983).

Kellum, J. M. et al. "Stroking human jejunal mucosa induces 5-HT release and CL secretion via afferent neurons and 5-HT4 receptors," Am J. Physiol, 277(3 Pt. 1):G515-20 (Sep. 1999). Abstract Only.

Khosla, R, et al. "The Effect of polycarbophil on the gastric emptying of pellets," J. Pharm. Pharmacol., vol. 39, pp. 47-49 (1987).

King, C.E. et al. "Breath Tests in the diagnosis of small intestine bacterial overgrowth," Critical Reviews in Clinical Laboratory Sciences, vol. 21(3), pp. 269-281 (1984).

King, P. J. et al. "Effect of cytokines on hypothalamic neuropeptide Y release in vitro," Peptides, 21(1):143-6 (Jan. 2000). Abstract Only.

King, P. J. et al. "Regulation of neuropeptide Y release from hypothalamic slices by melanocortin-4 agonists and leptin," Peptides 21(1):45-8 (Jan. 2000). Abstract Only.

King, P. J. et al. "Regulation of neuropeptide Y release by neuropeptide Y repeptor ligands and calcium channel antagonists in hypothalamic slices," J. Neurochem, 73(2):641-6 (1999). Abstract Only.

King, T.S. et al. "Abnormal colonic fermentation in irritable bowel syndrome," The Lancet, vol. 352(10), pp. 1187-1189 (1998).

Kirchgessner et al. "Identification of cells that express 5-hydroxytryptamine1A receptors in the nervous systems of the bowel and pancreas," J. Comp Neurol, 364(3):439-455 (Jan. 15, 1996). Abstract Only.

Kitchener, S. J. et al. "An examination of the behavioral specificity of hypophagia induced by 5-HT1b, 5-HT1C and 5-HT2 receptor agonists using the post-prandial satiety sequence in rats," Psychopharmacology, Berl, 113(3-4):369-77 (Jan. 1994). Abstract Only.

Knutson, D., et al., "Management of Crohn's disease—a practical approach," Am Fam Physician, 68(4):707-14 (Aug. 2003) Abstract Only.

Kofsky, P., et al., "*Clostridium difficile*—a common and costly colitis," Dis colon Rectum 34(3):244-8 (Mar. 1991). Abstract Only.

Kokot, F. et al. "Effects Neuropeptide Y on Appetite," Miner Electrolyte Metab, 25(4-6):303-305 (Dec. 1999). Abstract Only.

Kuemmerle, J.F. et al. "Serotonin neural receptors mediate motilin-induced motility in isolated, vascularly perfused canine jejunum," J. Surg Res 45(4):357-62 (Oct. 1998). Abstract Only.

Lai, K.K., et al. "*Clostridium difficile*-associated diarrhea: epidemiology, risk factors, and infection control," Infect Control Hosp Epidemiol 18(9): 628-32 (Sep. 1997) Abstract Only.

Laviano, A. "Peripherally injected IL-1 induces anorexia and increases brain tryptophan concentrations," Adv Exp Med Biol, 467:105-8(1999). Abstract Only.

Lembo et al. "Rifaximin for the Treatment of Diarrhea-Associated Irritable Bowel Syndrome: Short Term Treatment Leading to Long Term Sustained Response," Gastroenterology—AGA Abstracts, (Apr. 2008), 134(4, Suppl. 1):A545.

Lepionka, L. "Proximal gastric distension modifies ingestion rate in pigs," Reprod Nutr Dev, 37(4):449-57 (Jul.-Aug. 1997). Abstract Only.

Lin, H.C. "Oleate Slows Upper Gut Transit and Reduces Diarrhea in Patients with Rapid Upper Gut Transit and Diarrhea," Gastroenterology, 108(4):A638 (1995).

Lin, H.C. et al. "Acute Desensitization of Intestinal Motility Reponse (Abstract)," Gastroenterology, 103:1392 (1992).

Lin, H.C., et al. "Inhibition of gastric emptying by glucose depends on length of intestine exposed to nutrient," Am. J. Physiol., vol. 256, Ch. 19, pp. G404-G411 (1989).

Lin, H.C., et al. "Jejunal Brake, Inhibition of Intestinal Transit by Fat in the Proximal Small Intestine," Digestive Diseases and Sciences, XP 000613235, vol. 41, No. 2, pp. 326-329 (Feb. 1996).

Lin, H.C., et al. "Inhibition of Intestinal Transit by Fat Depends on Length of Exposure to Nutrient," Gastro., 106:A531 (1994) Abstract Only.

Lin, Henry C., et al. "Inhibition of gastric emptying by sodium oleate depends on length of intestine exposed to nutrient," Am. J. Physiology, vol. 259, Chap.22, pp. G1031-G1036 (1990).

Lin, Henry C. et al. "Intestinal Transit of Fat in Proximal Gut Depends on Accelerating Effect of CCK and Slowing Effect of Opioid Pathway," Digestive Diseases and Sciences, vol. 41, No. 9, Abstract A19 (Sep. 1996).

Lin, Henry C. et al. "PYY Release by Fat in the Proximal But Not Distal ½ of Gut Depends on Atropine-Blockable Cholinergic Pathway," Gastroenterology, vol. 114, No. 4, Hormones, Transmitters, Growth Factors, and their Receptors A1, Abstract G4744, (1998).

Lin, Henry C. et al. "Release of Cholecystokinin by proximal gut Fat is Independent of Chylomichron Transport," Gastroenterology, vol. 114, No. 4,Hormones, Transmitters, Growth Factors, and their Receptors A1, Abstract G4745 (1998).

Lin, Henry C. et al. "Slowing of Intestinal Transit by Fat in proximal Gut Depends on peptide YY," Neurogastroenterology and Motility, Blackwell Science Ltd. p. 82, Abstract 101 (1998).

Lin, Henry C. et al. "Fat-Induced Ileal Brake in the Dog Depends on peptide YY," Gastroenterology, vol. 110, pp. 1491-1495 (1996).

Lin, Henry C. et al. "Fat-Induced Ileal Brake Depends on Cholecystokinin," Gastroenterology, vol. 114, No. 4, A790 AGA Abstracts, Abstract G3252 (1998).

Lin, Henry C. et al. "Immunoneutralization of Calcitonin Gene-Related peptide (CGRP) During Inhibition of Intestinal Transit by Fat," Gastroenterology, vol. 114, No. 4, 790 AGA Abstracts, Abstract G3253 (1998).

Lin, Henry C. et al. Intestinal Transit Reponse to Fat in the Proximal Gut Depends on 5-Hydroxytryptamine, Gastroenterology, vol. 114 No. 4. A790 AGA Abstracts, Abstract G3254 (1998).

Lin, Henry C. et al. "Intestinal Transit is More Potently Inhibited by Fat in the Distal (Ileal Brake) than in the Proximal (Jejunal Brake) Gut," Digestive Diseases and Sciences, vol. 42, No. 1 pp. 19-25 (Jan. 1977).

Lin, Henry C. et al. "Frequency of gastric pacesetter potential depends on volume and site of distension," Am Physiol 270:G470-G475 (1996).

Lind, E., et al. "Crohn's disease. Clinical manifestations," Scand J Gastroenterol, 20(6):665-70 (Aug. 1985) Abstract Only.

Litvak, D. A. et al. "Characterization of two novel proabsorptive peptide YY analogs, BIM-43073D and BIM-43004C," Dig Dis Sci, 44(3):643-8 (Mar. 1999). Abstract Only.

Liu, C. D. et al. "Peptide YY: a potential proabsorptive hormone for the treatment of malabsorptive disorders," Am Surg, 62(3):232-6 (Mar. 1996). Abstract Only.

Liu, C. D. et al. "Intraluminal peptide YY induces absorption in vivo," Dis Colon Rectum, 40(4):478-82 (Apr. 1997). Abstract Only.

Liu, M. et al., "The role of enterostatin and apolipoprotein AIV on the control of food intake," Neuropeptides, 33(5):425-433 (Oct. 1999). Abstract Only.

Lynn et al., "Irritable Bowel Syndrome," The New England Journal of Medicine, (Dec. 23, 1994), 329(26):1940-1945.

MacIntosh, C. G. et al, "Effects of age on concentrations of plasma cholecystokinin, glucagon-like peptide 1, and peptide YY and their relation to appetite and pyloric motility," Am J Clin Nutr, 69(5):999-1006 (May 1999). Abstract Only.

Maida, V., et al., "Effects of cigarette smoking and dietary lipids on rat lipoprotein metabolism," Atherosclerosis, vol. 80, pp. 209-216 (1990).

Malservisi, S. et al., "An Alternative Treatment for Small Bowel Bacterial Overgrowth," Digestive Desease Week, A-244 (May 1997).

Mannon, P. J. et al., "Peptide YY/neuropeptide Y Y1 receptor expression in the epithelium and mucosal nerves of the human colon," Regul Pept, 83(1):11-9 (Aug. 1999). Abstract Only.

Marts, B.C., et al., "Patterns and prognosis of *Clostridium difficile* colitis," Dis Colon Rectum 37(8):837-45 (Aug. 1994) Abstract Only.

Mawe, G. M., "Peripheral neural serotonin receptors: identification and characterization with specific antagonists and agonists," Proc Natl Acad Sci USA, 83(24):9799-803 (Dec. 1986). Abstract Only.

McColl, K.E.L., et al. "Randomised trial endoscopy with testing for *Helicobacter pylori* compared with non-invasive *H pylori* testing alone in the management of dyspepsia," BMJ, vol. 324 (Apr. 2002), 999-1002.

McGill, Henry C., Jr. "Potential Mechansims for the Augmentation of Atherosclerosis and Atherosclerotic Disease by Cigarette Smoking," Preventive Medicine, vol. 8, pp. 390-403 (1979).

McHugh, P.R. et al. "The stomach, cholecystokinin, and satiety," Fed Proc, 45(5):1384-90 (Apr. 1986). Abstract only.

McKeown, L.A., "Breath Test Helps Sniff Out Irritable Bowel Syndrome: Majority of Sufferers May Have Treatable Bacterial Infections," WebMD Medical News, http://my.webmd.com/content/article/1728.66648 accessed Dec. 13, 2000.

Meissner, W., "Oral naloxone reverses opioid-associated constipation," Pain, 84(1):105-9 (Jan. 2000). Abstract Only.

Minina et al, "Development of an enterosoluble coating based on water-soluble shellac," Khim.-Farm, ZH., 12(2), 120-5 (Abstract), 1978.

Mishkin et al., Letter to Am. J. of Gastroenterology, 96(8): 2505-08 (2001).

Mjos, Ole D., et al., "Characterization of Remnants Produced during the Metabolism of Triglyceride-Rich Lipoproteins of Blood Plasma and Intestinal Lymph in the Rat," J. Clin. Investigation, vol. 56, pp. 603-615 (Sep. 1975).

Moran, T. H. et al. "Cholecystokinin suppresses food intake by inhibiting gastric emptying," Am J. Physiol, 242(5):R491-7 (May 1982). Abstract Only.

Morson, B.C., "Pathology of Crohn's disease," Ann R Coll Surg Engl, 72(3):150-1 (May 1990) Review.

Muranishi, S. et al. "Potential Absorption of Heparin from the Small Intestine and the Large Intestine in the Presence of Monoolein Mixed Micelles," Chem. Pharm. Bull. 25(5): 1159-1161 (1977).

Murthy, B.V. et al., "Intestinal pseudo-obstruction associated with oral morphine," Eur J Anaesthesiol, 15(3):370-1 (May 1998). Abstract only.

Naveilhan, P. et al., "Normal feeding behavior, body weight and leptin response require the neuropeptide Y Y2 receptor," Nat Med 5(10):1188-93 (Oct. 1999). Abstract Only.

Nayak et al., "Metronidazole Relieves Symptoms in Irritable Bowel Syndrome: The Confusion With So-Called 'Chronic Amebiases,'" Indian Journal of Gastroenterology, (1997), 16(4), pp. 137-139.

Noor, N., et al., "Effects of cisapride on symptoms and postcibal small-bowel motor function in patients with irritable bowel syndrome," Scand J. Gastroenterol 33(6): 605-11 (Jun. 1998) Abstract Only.

O'Brian, J.D., et al., Effects of codeine and loperamide on upper intestinal transit and absorption in normal subjects and patients with postvagotomy diarrhea, Gut, vol. 29 pp. 312-318 (1988).

O'Sullivan et al., "Probiotics in the Treatment of Irritable Bowel Syndrome (IBS): A Randomised Double Blind Placebo Controlled Crossover Study," Gastroenterology, (1996), 110(4), p. A727, Meeting Abstract.

Ohtani, N., et al., "Mediators For Ileal Brake Differ Between the Stomach and Small Intestine in Conscious Dogs," Gastroenterology, 108(4 Supp.) abst. 660 (1995).

Ormsbee, H. S. 3d, et al., "Action of serotonin on the gastrointestinal tract," Proc Soc Exp Biol Med, 178(3):333-8 (Mar. 1985). Abstract Only.

Pappas, T. N et al., "Gastric distension is a physiologic satiety signal in the dog," Dig Dis Sci, 34(10):1489-93 (Oct. 1989). Abstract Only.

Phillips, R. J. et al., "Gastric volume rather than nutrient content inhibits food intake," Am J. Physiol 271(3 Pt 2):R766-9 (Sep. 1996). Abstract Only.

Pimentel et al., "Eradication of Small Intestinal Bacterial Overgrowth Reduces Symptoms of Irritable Bowel Syndrome," Am. J. of Gastroenterology, 95(12):3503-06 (2000).

Pimentel, Mark, et al., "A 14-Day Elemental Diet Is Highly Effective in Normalizing the Lactulose Breath Test," Digestive Diseases and Sciences, vol. 49, No. 1 (Jan. 2004), pp. 73-77.

Pimentel, M., et al., "A link between irritable bowel syndrome and fibromyalgia may be related to findings on lactulose breath testing," Ann Rheum Dis (2004) 63:4 50-452.

Pimentel, Mark, et al., "Methane Production During Lactulose Breath Test is Associated with Gastrointestinal Disease Presentation," Digestive Diseases and Sciences, vol. 48, No. 1, Jan. 2003.

Pimentel, Mark, et al., "Normalization of Lactulose Breath Testing Correlates with Symptom Improvement in Irritable Bowel Syndrome: A Double-Blind, Randomized, Placebo-Controlled Study," The American Journal of Gastroenterology, vol. 98(2), 2003.

Pimentel, Mark, "Small Intestinal Bacterial Overgrowth: A Possible Association with Fibromyalgia," Journal of Musculoskeletal Pain, vol. 9(3), 2001.

Pimentel et al., "Selective Inhibition of Enteric Organisms By Mesalamine," Gastroenterology—AGA Abstracts, (1999), 116(4), Abstract No. G3452.

Pimentel et al., "The Effect of a Nonabsorbed Oral Antibiotic (Rifaximin) on the Symptoms of the Irritable Bowel Syndrome," Annals of Internal Medicine, (2005), 145:557-563.

Pironi, L., et al., "Fat-Induced Ileal Brake in Humans: A Dose-Dependant Phenomenon Correlated to the Plasma Levels of Peptide YY," Gastroenterology, vol. 105, pp. 733-739 (Sep. 1993).

Price, A.B., et al., "Inflammatory bowel disease: the surgical pathology of Crohn's disease and ulcerative colitis," Hum Pathol 6(1):7-29 (Jan. 1975) Abstract Only.

Quinton, F. et al., "Anti-*Saccharomyces cerevisiae* mannan antibodies combined with antineutrophil cytoplasmic autoantibodies in inflammatory bowel disease: prevalence and diagnostic role," Gut, vol. 42, pp. 788-791 (1998).

Read, et al., "Effect of Infusion of Nutrient Solutions Into the Ileum on Gastrointestinal Transit and Plasma Levels of Neurotens in and Enteroglucagon," Gastroenterology, 86(2):274-280 (1984).

Reasbeck, P. G. et al., "The effect of somatostatin on dumping after gastric surgery: A preliminary report," Surgery, vol. 99, No. 4, pp. 462-467 (Apr. 1986).

Redgrave, T.G., et al., "Changes in plasma very low density and low density lipoprotein content, composition, and size after a fatty meal in normo- and hypertriglyceridemic man," Journal of Lipid Research, vol. 20, pp. 217-229 (1979).

Rolak, L.A., "The diagnosis of multiple sclerosis," Neurol Clin, 14(1):27-43 (1996) Abstract Only.

Rombeau, John L. et al., "Enteral and Parenteral Nutrition on Patients with Enteric Fistulas and Short Bowel Syndrome," Surgical Clinics of North America, vol. 67, No. 3, pp. 551-571 (Jun. 1987).

Ruemmele, Frank, M., "Diagnostic Accuracy of Serological Assays in Pediatric Inflammatory Bowel Disease," Gastroenterology, vol. 115, pp. 822-829 (1998).

Sahu, A. et al. "Evidence that hypothalamic neuropeptide Y gene expression and NPY levels in the parventricular nucleus increase before the onset of hyperphagia in the experimental diabetes," Brain Res, 755(2):339-42 (May 1997). Abstract Only.

Sahu, A. "Evidence suggesting that galanin (GAL), melanin-concentrating hormone (MCH), neurotensin (NT), proopiomelano (POMC) and neuropeptide Y (NPY) are targets of leptin signaling in the hypothalamus," Endocrinology, 139(2):795-8 (Feb. 1998). Abstract Only.

Sanger, G. J. "5-Hydroxytryptamine and functional bowel disorders," Neurogastroenterol Motil, 8(4):319-31 (Dec. 1996). Abstract Only.

Sanger, G. J. "Hypersensitivity and hyperreactivity in the irritable bowel syndrome: An opportunity for drug discovery," Dig. Dis., 17(2):90-9 (1999). Abstract Only.

Sanger, G.J. et al. "Increased defecation during stress or after 5-hydroxytryptophan: selective inhibition by the 5-HT(4) receptor antagonist SB-207266," Br J Pharmacol, 130(3):706-12 (Jun. 2000). Abstract Only.

Santos, F. A. et al. "Quinine-induced inhibition of gastrointestinal transit in mice: possible involvement of endogenous opioids," Eur J Pharmacol, 364(2-3):193-7 (Jan. 1999). Abstract Only.

Saunders, David R., M.D., et al. "Absorption of triglyceride by human small intestine: dose-response relationships," sup.1-3, Am. J. Clin. Nutr. vol. 48, pp. 988-991 (1988).

Schemann, M, et al. "The Utility of Cellulose Meals for Studies on Gastrointestinal Motility in Dogs," Digestion, vol. 25, pp. 194-196 (1982).

Schemann, Michael, et al. "Postprandial Patterns of Canine Jejunal Motility and Transit of Luminal Content," Gastroenterology, vol. 90, pp. 991-1000 (1986).

Siegle, et al. "Effects of ileal infusions of nutrients on motor patterns of canine small intestine," American Journal of Physiology: Gastrointestinal and Liver Physiology, vol. 22, No. 1, pp. G78-G85 (Jul. 1990).

Silberbauer, C. J. et al. "Prandial lactate infusion inhibits spontaneous feeding in rats," Am J. Physiol Regul Integr Comp Physiol, 278(3);R646-R653 (Mar. 2000). Abstract Only.

Simansky, K. J. et al. "Peripheral serotonin is an incomplete signal for eliciting satiety in sham-feeding rats," Pharmacol Biochem Behav, 43: (3):847-54 (Nov. 1992). Abstract Only.

Simpson, James W. "Diet and Large Intestinal Disease in Dogs and Cats," Journal of Nutrition, vol. 128 (12 suppl) pp. 2717S-2722S (Dec. 1998).

Smith, B. K. "Activation of hypothalamic serotonin receptors reduced intake of dietary fat and protein but not carbohydrate," Am J. Phsiol 277(3 Pt 2):R802-11 (Sep. 1999). Abstract Only.

Soll, Andrew H., "Medical Treatment of Peptic Ulcer Disease," JAMA, Feb. 28, 1996, vol. 275, No. 8.

Soper, N.J., et al. "The 'Ileal Brake' After Ileal Pouch-Anal Anastomosis," Gastroenterology, 98(1):111-116 (Jan. 1990).

Sperber, A.D., et al. "Use of the Functional Bowel Disorder Severity Index (FBDSI) in a study of patients with the irritable bowel syndrome and fibromyalgia," Am J Gastroenterol 95(4):995-8 (Apr. 2000) Abstract Only.
Spiller, R.C., et al. "The ileal brake—inhibition of jejunal motility after ileal fat perfusion in man," Gut, 1984, vol. 25, 365-374.
Spiller, et al. "Further characterization of the "ileal brake" reflex in man—effect of ileal infusion of partial digests of fat, protein, and starch on jejunal motility and release of neurotens in, enteroglucagon, and peptide YY," Gut, 29:1042-1051 (1988).
Starha, L. et al., [Oral long-acting drugs. 8. Effects of palmitic and lauric acid and their glycerine esters on the slowing of the drug release], Cesk Farm, 21(7):311-4 (Sep. 1972). Title Only (Article in Czech).
Steadman, C. J. et al. "Selective 5-hydroxytryptamine type 3 receptor antagonism with ondansetron as treatment for diarrhea-predominant irritable bowel syndrome: a pilot study," Mayo Clin Proc, 67(8):732-8 (Aug. 1992). Abstract Only.
Surh et al., "Bacterial Contamination of the Small Bowel Evaluated By Breath Tests, [75]Se-Labelled Homocholic-Tauro Acid, and Scanning Electron Microscopy," Scandinavian Journal of Gastroenterology, (1990), 25(8):841-852.
Summers, R.W. "Computerized Analysis of Spike Burst Activity in the Small Intestine," IEEE Transactions on Biomedical Engineering, vol. BME-29, No. 5, pp. 309-314 (May 1982).
Swinard & Lowenthal, "Pharmaceutical Necessities—Emulsifying and Suspending Agents," Remington's Pharmaceutical Sciences, 17$^{th}$ sup. Ed., Gennaro (Ed.), Chapter 68, pp. 1296-1300 (1985).
Talley, N. J. "Review article: 5-hydroxytryptamine agonists and antagonists in the modulation of gastrointestinal motility and sensation: clinical implications," Aliment Pharmacol Ther, 6(3):273-89 (Jun. 1992). Abstract Only.
Tanaka, M., et al. "The pathological diagnosis and differential diagnosis of Crohn's disease," Hepatogastroenterology 37(1):18-31 (Feb. 1990) Abstract Only.
Thomas, D.R., et al. "Postantibiotic colonization with *Clostridium difficile* in nursing home patients," J Am Geriatr Soc 38(4):415-20 (Apr. 1990) Abstract Only.
Trespi, E. et al. "Intestinal Bacterial Overgrowth During Chronic Pacreatitis," Current Medical Research and Opinion 15(1): 47-52 (1999).
Tripp, G. et al. "DSM-IV and ICD-10: a comparison of the correlates of ADHD and hyperkinetic disorder," J Am Acad Child Adolesc Psychiatry, 38(2): 156-64 (Feb. 1999) Abstract Only.
Turton, M. D. et al., "A role for glucagon-like peptide-1 in the central regulation of feeding," Nature, 379(6560):69-72 (Jan. 4, 1996), Abstract Only.
Vaira et al. "Rifaximin suspension for the eradication of *Helicobacter pylori*," Current Therapeutic Research, (1997), 58(5):300-308. (Abstract).
Van Dijk, G. et al., "Glucagon-like peptide-1 (7-36) amide: a central regulator of satiety and interoceptive stress," Neuropeptides, 33(5):406-414 (Oct. 1999). Abstract Only.
Varga, G. et al. "Effect of deramciclane, a new 5-HT receptor antagonist, on cholecystokinin-induced changes in rat gastrointestinal function," Eur J Pharmacol, 367(2-3):315-23 (Feb. 19, 1999). Abstract Only.
Voigt, J. P. et al., "Evidence for the involvement of the 5-HT1A receptor in CCK induced satiety in rats," Naunyn Schmiedebergs Arch Pharmacol, 351(3):217-20 (Mar. 1995). Abstract Only.
Voigt, J. P. et al., "Feeding and 8-OH-DPAT-related release of serotnin in the rat lateral hypothalamus," Pharmacol Biochem Behav, 65(1):183-9 (Jan. 1, 2000). Abstract Only.
Wade, P. R. et al., "Analysis of the role of 5-HT in the enteric nervous system using anti-idiotopic antibodies to 5-HT receptors," Am J Physiol 266(3 Pt 1):G403-16 (Mar. 1994). Abstract Only.
Wade, P. R. et al., "Localization and function of a 5-HT transporter in crypt epithelia of the gastrointestinal tract," J. Neurosci, 16(7):2352-64 (Apr. 1, 1996). Abstract Only.
Warnick, G. Russell. "Enzymatic Methods for Quantification of Lipoprotein Lipids, Methods in Enzymology," vol. 129, pp. 101-123 (1986).

Way, et al. *Current Surgical Diagnosis & Treatment*, 9$^{th}$ sup. Ed., 1991; p. 1083.
Welch, I. McL., et al. "Effect of ileal infusion of lipid on jejunal motor patterns after a nutrient and nonnutrient meal," American Physiological Society, vol. 255, pp. G800-G806 (1988).
Wellman et al. "Intestinal Lavage in the Treatment of Crohn's Disease: A Pilot Study," Klinische Wochensschrift, vol. 60 No. 7, pp. 371-374, 1982.
Whitehead et al, "Systematic Review of the Comorbidity of Irritable Bowel Syndrome with Other Disorders: What are the Causes and Implications?" Gastroenterology, vol. 122, p. 1140-56 (2002).
Wolf, G. "Neuropeptides responding to leptin," Nutr Rev, 55(3):85-8 (Mar. 1997). Abstract Only.
Wu, Ai-Lien, et al. "Resistance of intestinal triglyceride transport capacity in the rat to adaptation to altered luminal environment," sup.1-3, Am. J. Clin. Nutr., vol. 29, pp. 157-168 (Feb. 1976).
Wu, Ai-Lien, et al. "Composition of lymph chylomicrons from proximal or distal rat small intestine," sup.1-3, Am. J. Clin. Nutr., vol. 33, pp. 582-589 (Mar. 1980).
Wu, Ai-Lien, et al. Transmucosal triglyceride transport rates in proximal and distal rat intestine in vivo, Journal of Lipid Research, vol. 16, pp. 251-257 (1975).
Yablon, S.A., et al. "Diarrhea in hospitalized patients," Am J. Phys Med Rehabil 71(2):102-7 (Apr. 1992) Abstract Only.
Yang et al., "Rifaximin versus Other Antibiotics in the Primary Treatment and Retreatment of Bacterial Overgrowth in IBS," Digestive Disease and Sciences, (2008), pp. 169-174, 53.
Young, G.P. "Colorectal disorders: A dietary management perspective," Asia Pacific J. Clin Nutr 9(Suppl.): S76-S82 (2000).
Yuan, C. S. et al. "The safety and efficacy of oral methylnaltrexone in preventing morphine-induced delay in oral-cecal transit time," Clin Pharmacol Ther, 61(4):467-75 (Apr. 1997). Abstract Only.
Yuan, C. S. et al., "Effects of intravenous methylnaltrexone on opioid-induced gut motility and transit time changes in subjects receiving chronic methadone therapy: a pilot study," Pain, 83(3):631-5 (Dec. 1999). Abstract Only.
Yuan, C. S. et al., "Methylnaltrexone for reversal of constipation due to chronic methadone use: a randomized controlled trial," JAMA, 283(3):367-72 (Jan. 19, 2000). (Abstract).
Zhou, X. T., et al. "Fat in Distal Gut Inhibits Intestinal Transit More Potently than Fat in Proximal Gut," Gastroenterology, vol. 108, No. 4, p. A714 (Abstract) (Apr. 1995). XP 000613263.
Zilversmit, D.B., "Chylomicrons," Chapter in *Structural and Functional Aspects of Lipoproteins in Living Systems*, Tria and Scanu Eds. Academic (press) New York, NY, Chapter C1, pp. 329-368 (1969).
Zilversmit, Donald B., Ph.D., "Atherogenesis: A Postprandial Phenomenon, George Lyman Duff Memorial Lecture," Circulation, vol. 60, No. 3, pp. 473-485 (1979).
NORMIX®, Rifaximina (Product insert), Scheda Tecnica (Jul. 4, 1997).
National Institute of Diabetes and Digestive and Kidney Diseases, Irritable Bowel Syndrome Fact Sheet, (Sep. 2007), NIH Publication No. 07-693.
Website reference: Great Smokies Diagnostic Laboratory (May 4, 1999).
PCT/US00/22168 ISR dated Jan. 23, 2001.
PCT/US00/22168 Written Opinion dated Jul. 26, 2001.
PCT/US00/22168 IPER dated Nov. 29, 2001.
PCT/US96/07165 ISR dated Jan. 6, 1997.
PCT/US96/07165 Written Opinion dated Apr. 28, 1997.
PCT/US96/07165 IPER dated Aug. 28, 1997.
EP00952739.1 Exam Report dated Apr. 28, 2004.
EP00952739.1 Exam Report dated Aug. 2, 2005.
PCT/US00/22030 Written Opinion dated Jul. 30, 2001.
PCT/US00/22030 IPER dated Dec. 6, 2001.
EP02725704.7 Exam Report dated Apr. 16, 2008.
EP02725704.7 Exam Report dated Jun. 26, 2007.
EP02725704.7 Exam Report dated Oct. 31, 2006.
EP02725704.7 Exam Report dated May 12, 2006.
AU2002256254 Notice of Acceptance dated Jan. 8, 2007.
AU2002256254 Examiner's Action dated Aug. 10, 2006.
AU2002256254 Examiner's Action dated Oct. 18, 2005.
AU2002256254 Examiner's Action dated Aug. 4, 2005.

AU2002256254 Search Report dated Oct. 13, 2005.
PCT/US02/12034 IPER dated Dec. 10, 2004.
PCT/US02/12034 Written Opinion dated Sep. 3, 2004.
PCT/US02/12034 ISR dated Jan. 23, 2003.
CA2444548 Examiner's Action dated Jul. 16, 2010.
CA2444548 Examiner's Action dated May 28, 2008.
CA2444548 Examiner's Action dated Jul. 19, 2007.
CA2444548 Examiner's Action dated Oct. 18, 2006.
JP2002-582263 Examiner's Action recd May 6, 2009.
JP2002-582263 Examiner's Action recd May 25, 2010.
PCT/US01/11238 ISR dated Oct. 18, 2001.
PCT/US01/11238 Written Opinion dated Aug. 19, 2002.
PCT/US01/11238 IPER dated Oct. 15, 2002.
European Search Report dated Oct. 19, 2010 for European Patent Application No. 10177153.3.
Biancone, L et al., Rifaximin in inactive crohn's disease: effect on the intestinal protein loss as assessed by the fecal [alpha] 1-antitrypsin clearance, Database accession No. EMB-1998371799, and Journal of Clinical Research, vol. 1, No. 293-301, 1998, pp. 289-301. Database EMBASE [online] Elsevier Science Publishers, Amsterdam, NL; 1998. Abstract Only.
Di Febo, G et al., "New trends in non-absorbable antibiotics in gastrointestinal disease", Database accession No. PREV199395094280, and Italian Journal of Gastroenterology, vol. 24, No. 9 Suppl. 2, 1992, pp. 10-13. Database Bios, Biosciences Information Service, Philadelphia, PA, U.S. 1992. Abstract Only.
Gionchetti P et al., Review—antibiotic treatment in inflammatory bowel disease: rifaximin, a new possible approach., European Review for Medical and Pharmacological Sciences, vol. 3, No. 1, Feb. 1999, pp. 27-30.
Scarpignato, C et al., "Managment of irritable bowel syndrome: novel approaches to the pharmacology of gut motility." Canadian Journal of Gastroenterology, vol. 13, Suppl. A, Mar. 1999, pp. 50A-65A.
Bayeli, P.F., et al. "Guide lines on intestinal dysmicrobism (SIBO Small Intestine Bacterial Overgrowth)," Minerva Gastroenterologica e Dietologica, 1999: 455 (4), pp. 297-308.
Bouhnik, Y., et al. "Bacterial populations contaminating the upper gut in patients with small intestinal bacterial overgrowth syndrome," Am. J. Gastroenterology, 1999: 94 (5), pp. 1327-1331.
Dinerman, H., et al. "Lyme Disease associated with fibromyalgia," Annals of Int. Med., 1992: 117: 281-285.
Gasbarrini, G. "Conclusions," Ital. J. Gastroenterol., 1992: 24, Suppl. 2; p. 23.
Gibson, G.R., et al. "Growth and activities of sulphate-reducing bacteria in gut contents of healthy subjects and patients with ulcerative colitis," FEMS Microbiology Ecol., 1991: 86:103.
Liu, C.D. et al. "A novel synthetic analog of peptide YY, BIM-43004, given intraluminally, is proabsorptive," J. Surgical Research, 1995: 59 (1), pp. 80-84.
Loubinoux, J., et al. "Sulfate-reducing bacteria in human feces and their association with inflammatory bowel diseases," FEMS Microbiology Ecol., 2002: 40, pp. 107-112.
Mishkin, et al. Letter, Am. J. Gastroenterology, Aug. 2001; vol. 96, No. 8, p. 2505.
Mörl, et al. "Structure-activity relationship of peptide-derived ligands at NPY receptors," in Neuropeptide Y and Related Peptides, vol. 162 of Handbook of Experimental Pharmacology, 2004; pp. 479-504.
Pallone, F., et al. "Antibacterial drugs in Crohn's disease," Ital. J. Gastroenterology, 1992: 24, Suppl. 2, pp. 17-18.
Pimentel, et al. Letter in response to Mishkin, Am. J. Gastroenterology, Aug. 2001; vol. 96, No. 8, pp. 2505-2506.
Pimentel, et al. Letter in response to Riordan, Am. J. Gastroenterology, Aug. 2001; vol. 96, No. 8, pp. 2507-2508.
Rachmilewitz, D., et al. "Sulphydryl blocker induced small intestinal inflammation in rats: a new model mimicking Crohn's disease," Gut, 1997: 41: 358-365.
Riordan, et al. Letter, Am. J. Gastroenterology, Aug. 2001; vol. 96, No. 8, pp. 2506-2507.
Roediger, W.E.W. et al., "Colonic sulfide in pathogenesis and treatment of ulcerative colitis," Digestive Diseases and Sciences, 1997: 42 (8), pp. 1571-1579.

PCT/US00/22030 ISR dated Feb. 28, 2001.
EP07075358 Extended Search Report dated Jul. 13, 2007.
EP07075358 Examination Report dated Aug. 20, 2008.
EP07075358 Examination Report dated Jan. 19, 2009.
EP10183223 Extended Search Report dated Jan. 4, 2011.
EP10183213 Extended Search Report dated Jan. 4, 2011.
AU2007201246 Exam Report dated Oct. 1, 2008.
AU2007201246 Notice of Acceptance dated Nov. 25, 2008.
EP10178066 Extended Search Report dated Oct. 20, 2010.
EP10181342 Search Report dated Feb. 15, 2011.
U.S. Appl. No. 09/374,142 Office Action dated Jul. 5, 2001.
U.S. Appl. No. 09/374,142 Office Action dated Aug. 29, 2001.
U.S. Appl. No. 09/374,142 Office Action dated Jun. 6, 2002.
U.S. Appl. No. 09/374,142 Office Action dated Nov. 13, 2002.
U.S. Appl. No. 09/374,142 Office Action dated Apr. 22, 2003.
U.S. Appl. No. 09/374,142 Office Action dated Dec. 4, 2003.
U.S. Appl. No. 09/374,142 Notice of Allowance dated Sep. 1, 2004.
U.S. Appl. No. 10/107,240 Office Action dated Feb. 11, 2003.
U.S. Appl. No. 10/107,240 Office Action dated Jun. 5, 2003.
U.S. Appl. No. 10/107,240 Office Action dated Jan. 2, 2004.
U.S. Appl. No. 10/107,240 Notice of Allowance dated May 4, 2004.
U.S. Appl. No. 10/915,193 Office Action dated Oct. 27, 2005.
U.S. Appl. No. 10/915,193 Notice of Allowance dated Dec. 28, 2005.
U.S. Appl. No. 11/234,516 Office Action dated Jul. 31, 2007.
U.S. Appl. No. 11/234,516 Office Action dated Aug. 17, 2007.
U.S. Appl. No. 11/234,516 Office Action dated Nov. 28, 2007.
U.S. Appl. No. 11/234,516 Notice of Allowance dated Jul. 31, 2008.
U.S. Appl. No. 11/838,672 Office Action dated Jul. 29, 2008.
U.S. Appl. No. 11/838,672 Office Action dated Sep. 26, 2008.
U.S. Appl. No. 11/838,672 Office Action dated Feb. 26, 2009.
U.S. Appl. No. 11/838,672 Office Action dated Jul. 8, 2009.
U.S. Appl. No. 11/838,672 Notice of Allowance dated Aug. 5, 2009.
U.S. Appl. No. 11/838,631 Office Action dated Jul. 25, 2008.
U.S. Appl. No. 11/838,631 Office Action dated Sep. 16, 2008.
U.S. Appl. No. 11/838,631 Office Action dated Mar. 9, 2009.
U.S. Appl. No. 11/838,631 Notice of Allowance dated Jul. 6, 2009.
U.S. Appl. No. 12/234,502 Office Action dated Oct. 22, 2009.
U.S. Appl. No. 12/234,502 Notice of Allowance dated Mar. 15, 2010.
U.S. Appl. No. 12/550,303 Office Action dated Jul. 26, 2010.
U.S. Appl. No. 12/550,303 Notice of Allowance dated Dec. 30, 2010.
U.S. Appl. No. 09/837,797 Office Action dated Sep. 16, 2002.
U.S. Appl. No. 09/837,797 Office Action dated Jan. 9, 2003.
U.S. Appl. No. 09/837,797 Office Action dated Feb. 9, 2004.
U.S. Appl. No. 09/837,797 Office Action dated Sep. 30, 2004.
U.S. Appl. No. 09/837,797 Office Action dated Jun. 6, 2005.
U.S. Appl. No. 09/837,797 Notice of Allowance dated Nov. 14, 2005.
U.S. Appl. No. 10/810,020 Office Action dated Jul. 14, 2005.
U.S. Appl. No. 10/810,020 Notice of Allowance dated Jan. 25, 2006.
U.S. Appl. No. 11/348,995 Office Action dated Mar. 14, 2008.
U.S. Appl. No. 11/348,995 Office Action dated Sep. 3, 2008.
U.S. Appl. No. 11/348,995 Office Action dated Jan. 12, 2009.
U.S. Appl. No. 11/348,995 Office Action dated Jun. 30, 2009.
U.S. Appl. No. 11/348,995 Notice of Allowance dated Jan. 29, 2010.
U.S. Appl. No. 11/411,733 Office Action dated Jun. 21, 2006.
U.S. Appl. No. 11/411,733 Office Action dated Dec. 22, 2006.
U.S. Appl. No. 11/411,733 Office Action dated Apr. 27, 2007.
U.S. Appl. No. 11/411,733 Office Action dated Jun. 8, 2007.
U.S. Appl. No. 11/411,733 Office Action dated Nov. 20, 2007.
U.S. Appl. No. 11/411,733 Office Action dated Feb. 2, 2009.
U.S. Appl. No. 10/853,824 Office Action dated Jun. 24, 2005.
U.S. Appl. No. 10/853,824 Notice of Allowance dated May 24, 2006.
U.S. Appl. No. 11/457,445 Office Action dated Mar. 28, 2008.
U.S. Appl. No. 11/457,445 Office Action dated Dec. 4, 2008.
U.S. Appl. No. 11/457,445 Office Action dated Apr. 7, 2009.
U.S. Appl. No. 11/457,445 Notice of Allowance dated Jun. 1, 2009.
U.S. Appl. No. 11/673,488 Office Action dated Mar. 28, 2008.
U.S. Appl. No. 11/673,488 Office Action dated Feb. 25, 2009.
U.S. Appl. No. 11/673,488 Notice of Allowance dated Aug. 7, 2009.
AU2001251396 Examiner's Report dated Feb. 22, 2005.
AU2001251396 Examiner's Report dated May 17, 2006.
AU2007200008 Examiner's Report dated Mar. 5, 2008.
CA2404889 Official Action dated Mar. 11, 2008.
EP 01924772.5-2107 Examination Report dated Feb. 2, 2007.

EP 01924772.5-2107 Examination Report dated Jan. 31, 2006.
EP 01924772.5-2107 Examination Report dated May 9, 2005.
EP 01924772.5-2107 Examination Report dated Oct. 22, 2003.
EP 01924772.5-2107 Third Party Observations dated Aug. 9, 2007.
EP 01924772.5-2107 Third Party Observations Report dated Oct. 11, 2006.
EP 07075724.0-2107 Extended Search Report dated Jan. 28, 2008.
EP 07075724.0-2107 Examination Report dated Jun. 4, 2006.
EP 07075723.2-2107 Extended Search Report dated Jan. 28, 2008.
EP 07075723.2-2107 Examination Report dated Jun. 5, 2008.
EP 07075757.0-2107 Extended Search Report dated Jan. 25, 2008.
KR 10-2002-7013608 Notice of Preliminary Rejection dated Feb. 28, 2006.
MX PA/a/2002/010030 Official Action dated 2005—Unofficial Translation.
U.S. Appl. No. 09/548,119 Office Action dated Dec. 11, 2001.
U.S. Appl. No. 09/548,119 Office Action dated Sep. 13, 2002.
U.S. Appl. No. 09/548,119 Notice of Allowance dated Dec. 17, 2002.
Allen, J.M. et al., Effects of Peptide YY and Neuropeptide Y on Gastric Emptying in Man. Digestion, 1984, vol. 30, pp. 255-262.
Chen, C.H. et al., PYY and NPY: Control of Gastric Motility via action on Y1 and Y2 Receptors in the DVS. Neurogasterroenteral and Motility, 1997, vol. 9, pp. 109-116.
King P.J. et al., Regulation of Neuropeptide Y Release by Neuropeptide Y Receptor Ligands and Calcium Channel Antagonists in Hypothalamic Slices. Journal of Neurochemistry, 1999. vol. 73 (2) pp. 641-646.
Lin, H.C. et al., Fat-Induced Ileal Brake in the Dog Depends on Peptide YY. Gastroenteralogy, 1996, vol. 110, pp. 1491-1495.
Morley J.E. et al., An Investigation of Tolerance to the Actions of Leptogenic and Anorexigenic Drugs in Mice. Life Sciences, vol. 41, pp. 2157-2165.
MacIntosh, C.G. et al., Effects of Age in Concentrations of Plasma Cholecystokini, Glucagon-like Peptide 1, and Peptide PYY and their Relation to Appetite and Pyloric Motility, American Journal of Clinical Nutrition, 1999, vol. 69, pp. 999-1006.
Pironi, L. et al., Fat-Induced Ileal Brake in Humans: A Dose-Dependent Phenomenon Correlated to the Plasma Levels of Peptide YY, Gastroenterology, 1993, , vol. 105, pp. 733-739.
PCT Publication WO 01/076631 dated Oct. 18, 2001.
PCT/US01/11238 IPRP dated Oct. 15, 2002.
EP Application No. 10181342.6 Extended Search Report dated Jun. 14, 2011.
Japanese Application No. 2009-016943 Office Action and English Translation dated Jul. 11, 2011.
Vanderhoof J.A. et al., Treatment Strategies for Small Bowel Bacterial Overgrowth in Short Bowel Syndrome. Journal of Pediatric Gastroenterology and Nutrition. (1998), 27(2):155-160.
Bearcroft, C.P., et al Postprandial plasma 5-hydroxtryptamine in diarrhea predominant irritable bowel syndrome: a study pilot. Gut, vol. 42, pp. 42-46 (1998).
Bueno, Lionel, at al Mediators and Pharmacology of Visceral Sensitivity: From Basic to Clinical Investigations Gastroenterology, vol. 112, pp. 1714-1743, (1997).
Coelho, Anne-Marie, et al., Mast Cell Degranulation Induces Delayed Rectal Allodynia in Rats; Role of Histamine and 5-HT. Digestive Diseases and Sciences, vol. 43, No. 4, pp. 727-737 (Apr. 1998).
Dobson, L. Clair, et al. Does the site of intestinal delivery of oleic acid alter the ileal brake response? International Journal of Pharmaceutics, vol. 195, pp. 63-70 (2000).
Donaldson, Jr. Robert M., Normal Bacterial Populations of the Intestine and Their Relation To Intestinal Function. The New England Journal of Medicine, vol. 270, No. 18, pp. 938-945 (Apr. 30, 1964).
Evans, Peter R. et at Gastroparesis and Small Bowel Dysmotility in Irritable Bowel Syndrome, Digestive Diseases and Sciences, vol. 42, No. 10 pp. 2087-2093 (Oct. 1997).
Florin, T. H. et al., A Role For Su(fate Reducing Bacteria in Ulceraive Colitis?, Gastroenterology, vol. 98, No. 5, part 2, p. A 170 Abstract Only.
Gorard, D.A. et al, Intestinal Motor Function in Irritable Bowel Syndrome, Dig. Dis., vol. 12 (2), pp. 72-84 (1994).

Goyal, M.B., Raj K. et al., Mechanisms of Disease, The Enteric Nervous System, The New England Journal of Medicine, vol. 334, No. 17, pp. 1106-1115 (Apr. 25, 1996).
Harvey, R.F. et al., Effect of Cholecystokinin on Colonic Motility and Symptoms in Patients with the Irritable-Bowel Syndrome, Based on a paper read to the British Society of Gastroenterology on Sep. 28, 1972, The Lancet, Saturday Jan. 6, 1973.
Heaton, K.W., Role of Dietary Fiber in Irritable Bowel Syndrome in R.W. Reed (ed.), Irritable bowel syndrome, Grune and Stratton, London, pp. 203-222 (1985).
Kellow, John E. et al., Enhanced Perception of Physiological Intestinal Motility in the Irritable Bowel Syndrome Gastroenterology, vol. 101: pp. 1621-1627 ( 1991 ).
Pang, X. et al., Mast Cell and Substance ?-Positive Nerve Involvement in a Patient with Both Irritable Bowel Syndrome and Interstitial Cystitis, Urology, vol. 47 (3), pp. 436-438 (1996).
Roediger, W.E.W. et al, Sulphide impairment of substrate oxidation in rat colonocytes: a biochemical basis for ulcerative colitis?, Clinical Science, vol. 85, pp. 623-627 (1993).
Roediger, E.W. et al., Reducing Sulfer Compounds of the Colon Impair Colonocyte Nutrition: Implications for Ulcerative Colitis, Gastroenterology, vol. 104, pp. 802-809, (1993).
Rosenberg, M. et al., Reproducibility and Sensitivity of Oral Malodor Measurements With A Portable Suphide Monitor, J. Dent Res. vol. 70(11),pp. 1436-1440, (Nov. 1991).
Suarez, F. et al., Differentiation of mouth versus gut as sire of origin of odoriferous breath gases after garlic ingesstion, Am J. Physiol, vol. 276 (2 pt) 1), pp. G425-G430 (1999).
Thompson, Grant W., Irritable bowel syndrome: pathogenesis and management, The Lancet, vol. 341, pp. 1569-1572 (Jun. 19, 1993).
Triadafilopoulos, George M.D. et al., Bowel Dysfunction in Fibromyalgia Syndrome Digestive Diseases and Sciences, vol. 36 No. 1, pp. 59-64 (Jan. 1991).
Valori, R.M. et al., Effects of Different Types of Stress and of "Prokinetic" Drugs on the Control of the Fasting Motor Complex in Humans, Gastronenterology, vol. 90, pp. 1890-1900 (1986).
Wangel D.G. et al., Intestinal motility in man, Ill; mechanisms of constipation and diarrhea with particular reference to the irritable colon syndrome, Gastroenterol, vol. 48, No. 1, pp. 69-84 (1965).
Wesselmann ,U et al., Pelvic pain; a chronic visceral pain syndrome, Curr, Pain Headache Rep. vol. 5(1), pp. I3-I9 (2001). Abstract Only.
Whitehead, Williams E. et al., Symptoms of Psychologic Distress Associated with Irritable Bowel Syndrome Gastroenterology, vol. 95, pp. 709-714, (1988).
Whitehead, William E. et al., Tolerance for Rectosigmoid Distention in Irritable Bowel Syndrome Gastroenterology, vol. 98, No. 5, pp. 1187-1192 (1990).
Woods, J.D. et al., Fundamentals of Neurogastroenterology, Gut, vol. 45 (Supp II), pp. II6-II16.
XP-000978709 Mark Pimentel, et al. Eradication of Small Intestinal Bacterial Overgrowth Decreases the Gastrointestinal Symptoms in Fibromyalgia, Gastroenterology, vol. 118, No. 4 Supl. 2 Part 1, p. AGA A413 (Apr. 2000).
XP-000978710 Mark Pimentel, et al. Comparison of Peak Breath Hydrogen Production in Patients with Irritable Bowel Syndrome, Chronic Fatigue Syndrome and Fibromyalgia, Gastroenterology. vol. 18. No. 4 Suppl. 2 Part I, p. AGA A413 (Apr. 2000).
XP-000979125 Mark Pimentel, et al. Eradication of Small Intestinal Bacterial Overgrowth Decreases Symptoms in Chronic Fatigue Syndrome: A Double Blind. Randomized Study, Gastroenterology, vol. 118, No. 4 Suppl. 2 Part 1, p. AGA A414 (Apr. 2000) Arthritis & Rheumatism, vol. 42, No. 9 Suppl., p. S343 ( 1999).
XP-000979873 E. Lederman, et al. Bacterial Overgrowth in the Neoterminal Ileum After Ileocolonic Resection for Crohn's Disease, Gastroenterology, vol. 112, No. 4 Suppl., p. A 1023 (1997).
XP000979874 P. Rutgeerts, et al. Small Bowel Bacterial Overgrowth. Ileal Dysfunction and Stool Fat Excretion in Patients with Unoperated Crohn's Disease. Gastroenterology, vol. 76. No. 5 Part 2. p. 1232 (1979).
XP-000981459 R.E. Cater, II The Clinical Importance of Hypochlorhydria (A Consequence of Chronic *Helicobater* Infection): Its Impossible Etiological Role in Mineral Amino Acid Malabsorption, Depression and Other Symptoms. Medical Hypotheses vol. 39, No. 4, pp. 375-383 (1992).
XP-000980196 Raymond Karcher, Ph.D., et al! Using a Cutoff of < 10ppm for Breath Hydrogen Testing: A Review of Five Years' Experience. Annals of Clinical and Laboratory Science vol. 29. No. I. pp. 1-8 (Jan. 1999).
XP-000980200 Yuji Funayma et al. Anti-bacterial Treatment for Postoperative Bacterial Overgrowth in Crohn's Disease. Gastroenterology, vol. 112, No. 4 Supp., p. A1444 (1997) SSAT Abstracts.
XP-002159720 G. Galatola et al., Diagnosis of Bacterial Contamination of the Small Intestine Using the I g '14C Xylose Breath Test in Various Gastrointestinal Diseases. Minerva Gastroenterol. Dietol.. vol. 37. pp. 169-175 (1991). Abstract Only.
XP-000980123 S. A. Albano et al., Small Intestinal Bacterial Overgrowth in Systemic Lupus Erythematosus (SLE). Arthritis & Rheumatism, vol. 42, No. 9 Suppl., p. S305, Abstract 1409a (Nov. 13-14, 1999).
XP-000979785 C. Prantera et al., An Antibiotic Regimen for the Treatment of Active Crohn's Disease: A Randomized. Controlled Clinical Trial of Metronidazole plus Ciprofloxacin, The American Journal of Gastroenterology vol. 91, No. 2, pp. 328-332 (1996).
XP-000979794 F. Casellas et al., Potential Usefulness of Hydrogen Breath Test with d-Xylose in Clinical Management of Intestinal Malabsorption, Digestive Diseases and Science, vol. 38, No. 2, pp. 321-327 (Feb. 1993).
XP-000981761 A. Schneider et al., Value of the 14C-D-Xylose Breath Test in Patients with Intestinal Bacterial Overgrowth, Digestion, 32:86-91 (1985).
XP-000980122 M. Pimentel et al., Eradication of Small Intestinal Bacterial Overgrowth Decreases Symptoms in Fibromyalgia: A Double Blind Randomized Study, Arthritis & Rheumatism, vol. 42, No. 9 Suppl., p. S343, Abstract 1632 (Nov. 13-14, 1999).
International Search Report, mailed Oct. 18, 2001 regarding PCT/US01/11238.
Warren, R.P., et al. "Elevated serotonin levels in autism: association with the major histocompatibility complex", Neuropsychobiology, 1996, vol. 34, No. 2, pp. 72-75.
Bernstein, L.H., et al. "Experimental production of elevated serum folate in dogs with intestinal blind loops. II. Nature of bacterially produced folate coenzymes in blind loop fluid", The American Journal of Clinical Nutrition, 1975, vol. 28, pp. 925-929.
Branski, D., et al. "Intrahepatic cholestasis for 15 years without cirrhosis", Journal of Clinical Gastroenterology, 1980, vol. 2, No. 3, pp. 251-257.
Balestri, P.L., et al. "Elevated bile acid serum concentrations in uremics", Nephron, 1996, vol. 72, No. 2, p. 325.
Morain et al., Elemental Diet as Primary Treatment of Acute Crohn's Disease: A Controlled Trail, British Medical Journal, (Jun. 23, 1984), pp. 1859-1862, 281.
Batt, R.M., Exocrine Pancreatic Insufficiency, Gastroenterology, (May 1993), pp. 595-608, 23(3).
Rao et al., Intestinal Lymphangiectasia Secondary to Radiotherapy and Chemotherapy, Digestive Diseases and Sciences, (Aug. 1987), pp. 939-942, 32(8).
Suarez et al., Pancreatic Supplements Reduce Symptomatic Response of Healthy Subjects to a High Fat Meal, Digestive Diseases and Sciences, (Jul. 1999), pp. 1317-1321, 44(7).
Tim et al., The Use of an Elemental Diet in Gastro-Intestinal Diseases, South African Medical Journal, (Oct. 9, 1976), pp. 1752-1756, 50 (43).
Costello, et al, The effect of an elemental diet on stool output in irritable bowel syndrome, Proceedings of the Nutrition Society vol. 53 No. 3 pp. 223A (1994).
Morisse, et al, Effect if a Fructo-Oligo-Saccharides Compound in Rabbits Experimentally infected with E. coli. Journal of Applied Rabbit Research. vol. 15, pp. 1137-1143 (1992).
Young, G. Colorectal disorders: A Dietary management perspective, Asia Pacific J. Clin Nutr. vol. 9 (Suppl), pp. S76-S82 (2000).
Cummings, J.H et al. The control and consequences of bacterial fermentation in the human colon. J of Applied Bacteriology vol. 70 pp. 443-459 (1991).
Simpson J.W. Diet and Large Intestinal Disease in Dogs and Cats, J. of Nutrition, vol. 128 pp. 2717S-2722S (1998).

Alander, M. et al. The effect of probiotic strains on the microbiota of the Simulator of the Human Intestinal Microbial Ecosystem (SHIME), Int J. Food Microbiol 46(1):71-9 (1999): Abstract Only.
Alpert J.E. et al. Attention deficit hyperactivity disorder in childhood among adults with major depression. Psychiatry Res. 62(3):213-219 (Jun. 1, 1999). Abstract Only.
Annesse, V. et al. Gastrointestinal motility disorders in patients with inactive Crohn's disease. Scand J. Gastroenteral. 32(11):1107-17 (Nov. 1997). Abstract Only.
Autschbach, F. et al. In situ expression of interleukin-10 in noninflammed human gut and in inflammatory bowel disease. Am J. Pahtol. 153(1):120-30 (Jul. 1998). Abstract Only.
Bennett, G. et al. Nerve growth factor induced hyperalgesia in the rat hind paw is dependent on circulating neutrophils, Pain, 77:315-322 (1998).
Babyatsky, M.W. et al. Expression of transforming growth factors alpha and beta in colic mucosa in inflammatory bowel disease. Gastroenterology. 110(4): 975-84 (Apr. 1996). Abstract Only.
Bell. I.R. et al., Illness form low levels of environmental chemicals: relevance to chronic fatigue syndrome and fibromyalgia. The American Journal of Medicine. vol. 105 (3A), pp. 74S-82S (Sep. 28, 1998).
Bjornsson, E.S., Comparison between physiologic and erythromycin-induced interdigestive motility, Scand J. Gastroenteral 30(2):139-45 (Feb. 1995). Abstract Only.
Bruin, K,F. et al. Modulation of cytokine release from human monocytes by drugs used in the therapy of inflammatory bowel diseases. Eur J. Gastroenteral Hepatol, 7(8):791-5 (Aug. 1995). Abstract Only.
Bruno, Richard L. et al., Parallel& etween Post-Polio Fatigue and Chronic Fatigue Syndrome: A Common Pathophysiology? The American Journal of Medicine. 105(3A):66S-73S (1998).
Camoglio, L. et al. Altered expression of interferon-gamma and interleukin-4 in inflammatory bowel disease, Inflamm Bowel Dis, 4(4):285-90 (Nov. 1998). Abstract Only.
Casafont, M.F. et al., Small bowel bacterial overgrowth in patients with alcoholic cirrhosis. Dig Dis Sci. 41(3):552-6 (Mar. 1996). Abstract Only.
Casini-Raggi, V. et al., Mucosal imbalance of IL-1 and IL-1 receptor antagonist in inflammatory bowel disease. A novel mechanism of chronic intestinal inflammation. J Immunol. 154(5):2434-40 (Mar. 1, 1995).Abstract Only.
Castedal M. Postprandial peristaisis in the human duodenum. Neurogastroenteral Motil, 10(3):227-33 (Jun. 1998). Abstract Only.
Chang C.S. et al. Small intestine dysmotility and bacterial overgrowth in cirrhotic patients with apontaneous bacterial peritonitis. Hepatology, 28(5):1187-90 (Nov. 1998). Abstract Only.
Chang C.S. Increased accuracy of the carbon-14 D-xylose breath test in detecting small-intestinal bacterial overgrowth by correction with the gastric emptying rate. Eur J. Nucl Med, 22(10): 1118-22 (Oct. 1995). Abstract Only.
Chesta, J., Abnormalities in proximal small bowel motility in patients with cirrhosis, Hepatology, 17(5):828-32 (May 1993). Abstract Only.
Cominelli, F. Interleukin-1 and interleukin-1 receptor antagonist in inflammatory bowel disease , Aliment Pharmacol Ther, 10 Suppl 2:49-53; discussion 54 (1996). Abstract Only.
Corazza G.R., The diagnosis of small bowel bacterial overgrowth. Reliability of jejunal culture and inadequacy of breath hydrogen testin. Gastroenterology 98(2):302-9 (Feb. 1990). Abstract Only.
Corazza, G. Prevalence and consistency of low breath H2 excretion following lactulose ingestion. Possible implications for the clinical use of the H2 breath test. Dig Dis Sci 38(11):2010-6 (Nov. 1993). Abstract Only.
Daig, R. et al. Increased interleukin 8 expression in the colon mucosa of patients with inflammatory bowel disease. Gut, 38(2):216-22 (Feb. 1996). Abstract Only.
Dantzer, R et al., Cytokines and Sickness Behavior, Annals New York Academy of Sciences, vol. 840, pp. 586-590 (May 1, 1998).
De Becker, Pascale et al., Autonomic Testing in Patients with Chronic Fatigue Syndrome, The American Journal of Medicine, vol. 105(3A), pp. 22S-26S. (Sep. 28, 1998).
de Boissieu, D. et al. Small-bowel bacterial overgrowth in children with chronic diarrhea, abdominal pain or both, The Journal of Pediatrics, vol. 128, No. 2 pp. 203-207 (Feb. 1996).

de Campos, R.O.P. et al., Systemic treatment with *Mycobacterium bovis* bacillus calmette-guerin (BCG) potentiates kinin B, receptor agaonist-induced nociception and oedema formation in the formalin test in mice, Neuropeptides, vol. 32, No. 5m pp. 393-343 (1998).
Dellert, S. F. et al., the 13C-xylose breath test for the diagnosis of small bowel bacterial overgrowth in children. J. Pediatr Gastroenterl Nutr, 25(2);153-8 (Aug. 1997). Abstract Only.
Demitract, Mark A. Neuroendocrine Aspects of Chronic Fatigue Syndrome: A Commentary, The American Journal of Medicine. vol. 105(3A), pp. 11S-14S (Sep. 28, 1998).
Dinarello, C.A., Role of pro- and anti-inflammatory cytokines during inflammation: experimental and clinical findings, J Biol Regul Homeost Agents, 11(3): 91-103 (Jul.-Sep. 1997)/ Abstract Only.
Evans, P.R. et al., Gastroparesis and small bowel dysmotility in irritable bowel syndrome. Dig Dis Sci. 42(10):2087-93 (Oct. 1997). Abstract Only.
Faraone, S.V. et al. Psychiatic, neuropscholigical, and psychosocial features of DSM-IV subtypes of attention-deficit/hyperactivity disorder: results from a clinically referred sample. J Am Acad Child Adolesc Psychiatry, 37(2): 185-93 (Feb. 1998). Abstract Only.
Feghali, C.A. et al., Cytokines in acute and chronic inflammation. Front Biosci, 2:d12-28 (Jan. 1997). Abstract Only.
Feher, E. et al., Direct morphological evidence of neuroimmunomoudulation in colonic mucosa of patients with Crohn's disease, Neuroimmunomodulation, 4(5-6):250-7 (Sep.-Dec. 1997). Abstract Only.
Fellermann, K. et al. Steroid-unresponsive acute attacks of inflammatory bowel disease: immunomodulation by tacrolimus (FK506), Am J. Gastroenterol, 93(10):1860-6 (Oct. 1998). Abstract Only.
Fenner, H. [No title available] Z Rheumatol, 57(5):294-7 (Oct. 1998). Abstract Only.
Funakoshi, K et al., spectrum of cytokine gene expression in intestinal mucosal lesions of Crohn's Disease and ulcerative colitis. Digestion 59(1):73-8 (1998). Abstract Only.
Gardiner, G. et al. Development of a Probiotic Cheddar Cheese Containing Human-Derived *Lactobacillus paracasei* Strains, Applied and Environmental Microbiology, vol. 64, No. 6, pp. 2192-2199 (1998).
Gielkena, H.A. et al. Interdigestive antroduodenal motility and gastric acid secretion, Aliment Phamacol Ther, 12(1):27-33 (Jan. 1998). Abstract Only.
Glaser, R. Stress-Associated Immune Modulation: Relevance to Viral Infections and Chronic Fatigue Syndrome. The American Journal of Medicine. vol. 105 (3A), pp. 35S-42S (Sep. 28, 1998).
Gorard, D. A. et al. Ambulatory small intestinal motility in 'diarrhoea' predominant irritable bowel syndrome, Gut 35(2):203-10 (1994). Abstract Only.
Gorard, D.A. et al. Intestinal motor function in irritable bowel syndrome. Dig Dis 12(2):72-84 (Mar.-Apr. 1994). Abstract Only.
Guimbaud, R. et al. Network of inflammatory cytokines and correlation with disease activity in ulcerative colitis. Am J Gastroenterol, 93(12):2397-404 (Dec. 1998). Abstract Only.
Hang, L. et al. Cytokine repertoire of epithelial cells lining the human urinary tract. J. Urol 159(6):2185-92 (Jun. 1998). Abstract Only.
Harlow, B. L. Reproductive Correlates of Chronic Fatigue Syndrome. The American Journal of Medicine. Bol 105(3A), pp. 94S-99S (Sep. 28, 1998).
Hellstrom, P.M. et al., Role of bile in regulation of gut motility. J Intern Med 237(4):395-402 (Apr. 1995). Abstract Only.
Hori, T. e tal., Pain Modulatory Actions of Cytokines and Prostaglandin E2 in the Brain, Annals New York Academy of Sciences, vol. 840, pp. 269-281 (May 1, 1998).
Hudziak, J. J. et al. Latent class and factor analysis of DSM-IV ADHD: a twin study of female adolescents. J Am Acad Child Adolesc Psychiatry, 37 (8):848-57 (Aug. 1998). Abstract Only.
Hyams, J.S. et al. Relationship of interleukin-1 receptor antagonist to mucosal inflammation in inflammatory bowel disease. J Pediatr Gastroenterol Nutr, 21(4):419-25 (Nov. 1995). Abstract Only.
Jason, L. et al. Estimating the Prevalence of Chronic Fatigue Syndrome Among Nurses. The American Journal of Medicine. vol. 105 (3A), pp. 91-93S (Sep. 28, 1998).

Kanik, K.S. et al. Distinct patterns of cytokine secretion characterize new onset synovitis versus chronic rheumatoid srthritis, J. Rheumatol 25(1):16-22 (Jan. 1998). Abstract Only.
Kellow J.E. et al. Enhanced perception of physiological intestinal motility in the irritable bowel syndrome. Gastroenterology, 101(6):1621-7 (Dec. 1991). Abstract Only.
Kerlin, P. et al. Breath hydrogen testing in bacterial overgrowth of the small intestine. Gastroenterology, 95(4): 982-8 (Oct. 1988). Abstract Only.
King, C. E. et al. Comparison of the 1-gram (14C)xylose, 10-gram lactulose-H2, and overgrowth. Gastroenterology 91(6):147-51 (Dec. 1996). Abstract Only.
Kontula, P. et al., The effect of lactose derivatives on intestinal lactic acid bacteria, J. Dairy Sci 82(2);249-56 (Feb. 1999). Abstract Only.
Kuboyama, S. Increased circulating levels of interleukin-1 receptor antagonist in patients with inflammatory bowel disease Kurume Med J. 45(1); 33-7 (1998). Abstract Only.
Kucharzik, T. Circulating anti-inflammatory cytokine IL-10 in patients with inflammatory bowel disease (IBD), Clin Exp Immunol, 100(3):452-6 (Jun. 1995). Abstract Only.
Kucharzik T. et al., Immunoregulatory properties of IL-13 in patients with inflammatory bowel disease; comparison with IL-4 and IL-10. Clin Exp Immunol 104(3). 483-90 (Jun. 1996). Abstract Only.
Kucharzik, T. Synergistic effect of immunoregulatory cytokines on peripheral blood monocytes from patients with inflammatory bowel disease, Dig Dis Sci 42(4): 805-12 (Apr. 1997). Abstract Only.
LaManca, J.J. Influence of Exhaustive Treadmill Exercise on Cognitive Funtioning in Chronic Fatigue Syndrome. The American Journal of Medicine, vol. 105(3A). pp. 59S-65S (Sep. 28, 1998).
Lange, Fudrun et al. Neuroimaging in Chronic Fatigue Syndrome. The American Journal of Medicine. vol. 105(3A), pp. 50S-53S (Sep. 28, 1998).
Leiper, K. et al. Adjuvant post-operative therapy. Bailleres Clin Gastroenterol, 12(1):179-99 (Mar. 1998). Abstract Only.
Lembeke, B. Breath tests in intestinal diseases and functional gastrointestinal diagnosis. Schweiz Rundsch Med Prax, 85(25-26):1060-7 (Jun. 18, 1997). Abstract Only.
Levine, P.H. What we know about chronic fatigue syndrome and its relevance to the practicing physician. The American Journal of Medicine. vol. 105(3A), pp. 100S-103S (Sep. 28, 1998).
Lewindon P.J et al. Bowel dysfunction in cystic fibrosis: importance of breath testing. J. Paediatr Child Health, 34(1):79-82 (Feb. 1998). Abstract Only.
Lugering, N. et al. Current concept of the role of monocytes/macrophages in inflammatory bowel-disease—balance of proinflammatory and immunisuppressive mediators. Ital J. Gastroenterol Hepatol, 30(3):338-44 (Jun. 1998). Abstract Only.
Luiking, Y.C. et al. Migrating motor complex cycle duration is determined by gastric or duodenal origin of phase III, Am. J. Physiol. 275(6 Pt 1): G1246-1251 (Dec. 1998). Abstract Only.
MacDermott, R.P. Alterations of the mucosal immune system in inflammatory bowel disease. J Gastroenterol, 31(6):907-16 (Dec. 1996).
Marlin, R.G., An evaluation of multidisciplinary intervention for chronic fatigue syndrome with long-term follow-up, and a comparison with untreated controls. The American Journal of Medicine. vol. 105(3A)pp. 110S-114S (Sep. 28, 1998).
Mack, D.R. et al. Small bowel bacterial overgrowth as a cause of chronic diarrhea after liver transplantation in children. Liver Transpl Surg, 4(2):166-9 (Mar. 1998). Abstract Only.
Maini, R.N. A perspective on anti-cytokine and anti-T cell-directed therapies in rheumatoid arthritis Clin Exp Rheumatol, 13 Suppl 12:S35-40 (Sep.-Oct. 1995). Abstract Only.
Mastropaolo, G. et al. Evaluation of the drogen breath test in man: definition and elimination of the early hydrogen peak, Gut, 28(6):721-5 (Jun. 1987). Abstract Only.
Matsukawa, A. Analysis of the inflammatory cytokine network among TNF alpha, IL-1 beta, IL-1 receptor antagonist, and IL-8 and LPS-induced rabbit arthritis. Lab Invest. 76(5): 629-38 (May 1997). Abstract Only.
Matsukawa, A. et al. Sequential generation of cytokines during the initiative phase of inflammation, with reference to neutrophils, Inflamm Res, 47 Suppl 3:S137-44.

Morencos F. et al. Small Bowel Bacterial Overgrowth in Patients with Alcoholic Cirrhosis, Dig. Dis Sci. vol. 40, No. 6 (Jun. 1995).

Muller, S. et al. Activated CD+4 and CD8+ cytotoxic cells present in increased numbers in the intestinal mucosa from patients with active inflammatory bowel disease, Am J. Pathol, 152(1):261-8 (Jan. 1998). Abstract Only.

Murata, Y., The role of proinflammatory and immunoregulatory cytokines in the pathogenesis of ulcerative colitis. J Gastroenterol, 30 Suppl 8:56-60, (Nov. 1995). Abstract Only.

Murphy, K. Adults with attention deficit hyperactivity disorder: assessment and treatment considerations, SEmin Speech Lang, 17(3):245-53; quiz 254 (Aug. 1996). Abstract Only.

McVay, L.D. Changes in human mucosa gamma delta T cell repertoire and function associated with the disease process in inflammatory bowel disease, Mol Med 3(3):183-203 (Mar. 1997). Abstract Only.

Naidu, A. S. et al., Probiotic spectra of lactic acid bacteria (LAB), Crit Rev Food Sci Nutr, 39(1):13-126 (Jan. 1999). Abstract Only.

Nassif, A. et al. Role of cytokines and platelet-activating factor in inflammatory bowel disease. Implications for therapy. Dis colon Rectum, 39(2):217-23 (Feb. 1996).Abstract Only.

Natelson, B.H. Immunologic Parameters in Chronic Fatigue Syndrome, Major Depression, and Multiple Sclerosis. The American Journal of Medicine. vol. 105(3A), pp. 43S-49S (Sep. 28, 1998).

Nielson, O.H. Intestinal interleukin-8 concentration and gene expression in inflammatory bowel disease. Scand J. Gastroenterol, 32(10): 1028-34 (Oct. 1997). Abstract Only.

Niessner, M. Altered Th1/Th2 cytokine profiles in the intestinal mucosa of patients with inflammatory bowel disease as assessed by quantitative reversed transcribed polymerase chain reaction (RT-PCR), Clin Exp Immunol, 101(3):428-35 (Sep. 1995). Abstract Only.

Nieuwenhuijs, V.B. et al. Disrupted bile flow affects interdigestive small bowel motility in rats, Surgery. 122(3):600-8 (Sep. 1997). Abstract Only.

Nieuwenhuijs, V.B. et al. The role of interdigestive small bowel motility in the regulation of gut microflora, bacterial overgrowth, and bacterial translocation in rats, Ann Surg, 228(2):188-93 (Aug. 1998). Abstract Only.

Nieuwenhuijs, V.B. et al. The effects of ABT-229 and octreotide on interdigestive small bowel motility, bacterial overgrowth and bacterial translocation in rats. Eur J. Clin Invest. 29(1);33-40 (Jan. 1999). Abstract Only.

Panja, A. et al., The regulation and functional consequence of proinflammatory cytokine binding on human intestinal epitherlial cells. J. Immunol. 161(7):3675-84 (Oct. 1998). Abstract Only.

Parkes, M. et al. Contribution of the IL-2 and IL-10 genes to inflammatory bowel disease (IBD) susceptibility, Clin Exp Immunol. 113(1): 28-32 (Jul. 1998). Abstract Only.

Peterson, R.L. et al. Molecular effects of recombinant human interleukin-11 in the HLA-B27 rat model of inflammatory bowel disease, Lab Invest. 78(12):1503-12 (Dec. 1998). Abstract Only.

Poole, S. et al., Bradykinin B1 and B2 receptors, tumour necrosis factor alpha and inflammatory hyperalgesia, Br J. Pharmacol, 126(3):649-56 (Feb. 1999). Abstract Only.

Propst, A. et al., Interleukin-1 receptor antagonist in differential diagnosis of inflammatory bowel diseases, Eur J. Gastroentereol Hepatol, 7(11):1031-6 (Nov. 1995). Abstract Only.

Radford-Smith, G., Cytokines and inflammatory bowel disease. Baillieres Clin Gastroenterol. 10(1):151-64 (Mar. 1996). Abstract Only.

Reimund, J.M et al., Antioxidants inhibit the in vitro production of inflammatory cytokines in Crohn's disease and ulcerative colitis. Eur J. Clin Invest. 28(2):145-50 (Feb. 1998). Abstract Only.

Rhodes, J.M et al. The lactulose hydrogen breath test as a diagnostic test for small-bowel bacterial overgrowth. Scand J. Gastroenterol 14(3):333-6 (1979). Abstract Only.

Riordan, S.M. et al., Small intestinal bacterial overgrowth in the symptomatic elderly, The American Journal of Gastroenterology. vol. 92 No. 1, pp. 47-51 (1997).

Riordan, S.M et al., The lactulose breath hydrogen test and small intestinal overgrowth. Am J. Gastroenterol, 91(9):1795-803 (Sep. 1996). Abstract Only.

Rogler, G. et al., Cytokines in inflammatory bowel disease, World J. Surg 22(4):382-9 (Apr. 1998).Abstract Only.

Rowe, P.C. et al. Neurally Mediated Hypotension and Chronic Fatigue syndrome. The American Journal of Medicine. vol. 103(3A), pp. 15S-21S (Sep. 28, 1998).

Ruseler-van Embden, J.G. et al., Anaerobic gram-negative faecal flora in patients with Crohn's disease and healthy subjects. Antoine Van Leeuwennhock, 49(2):125-32 (Jun. 1983). Abstract Only.

Saiki, T. et al., Detection of pro- and anti-inflammatory cytokines in stools of patients with inflammatory bowel disease. Scand J Gastroenterol. 33(6):616-22 (Jun. 1998). Abstract Only.

Sakai, T. et al. Interleukin 15 activity in the rectal mucosa of inflammatory bowel disease. Gastroenterology. 114(6):1237-43 (Jun. 1998). Abstract Only.

Sartor, R.B. Pathogenesis and Immune Mechanisms of Chronic Inflammatory Bowel Disease. The American Journal of Gastroenterology. vol. 92, No. 12, pp. 5S-11S (1997).

Schmidt, T. et al. Ambulatory 24-hour jejunal motility in diarrhea-predominant irritable bowel syndrome, Scand J. Gastroenterol 31(6):581-9 (Jun. 1996). Abstract Only.

Schneider, A. et al., Value of the 14C-D-xylose breath test in patients with intestinal bacterial overgrowth. Digestion. 32(2):86-91 (1985). Abstract Only.

Schreiber, S. et al., Impaired response of activated mononuclear phagocytes to interleukin 4 in inflammatory bowel disease. Gastroenterology 108(1); 21-33 (Jan. 1995). Abstract Only.

Schreiber, S. et al. Immunoregulatory role of interleukin 10 in patients with inflammatory bowel disease. Gastroenterology 108(5):1434-44 (May 1995). Abstract Only.

Schreiber, S. Experimental immunomodulatory therapy of inflammatory bowel disease. Neth J. Med. 53(6): S24-31 (Dec. 1998). Abstract Only.

Sharpe, M. Cognitive Behavior Therapy for Chronic Fatigue Syndrome: Efficacy and Implications. The American Journal of Medicine. vol. 105(3A): pp. 104S-109S (Sep. 28, 1998).

Shigematsu, S. Therapeutic potential of interleukin-1 receptor antagonist in inflammatory bowel disease. Kurume Med J. 45(2):175-9 (1998). Abstract Only.

Soderholm, J.D et al., Epithelial Permeability to Proteins in the Noninflamed ileum of Crohn's Disease. Gastroenterology vol. 117, pp. 65-72 (1999).

Spanhaak, S. The effect of consumption of milk fermented by *Lactobacillus casei* strain Shirota on the intestinal microflora and immune parameters in humans. Eur J. Clin Nutr. 52(12):899-907 (Dec. 1998). Abstract Only.

Stack, WA et al., Randomised controlled trial of CDP571 antibody to tumour necrosis factor-alpha in Crohn's disease. Lancet 349(9051):521-4 (Feb. 22, 1997). Abstract Only.

Stotzer, P.O et al., Interdigestive and postprandial motility in small-intestinal bacterial overgrowth. Scand J. Gastroenterol. 31(9):875-80 (Sep. 1996). Abstract Only.

Strocchi, A. et al. Detection of malabsorption of low doses of carbohydrate: accuracy of various breath H2 criteria. Gastroenterology 105(5):1404-10 (Nov. 1993).Abstract Only.

Swanink, C.M. et al. *Yersinia enterocolitica* and the chronic fatigue syndrome. J Infect. 36(3):269-72 (May 1998). Abstract Only.

Swart, G.R. et al., 13C breath test in gastroenterological practice. Scand J. Gastroenterol Suppl. 225:13-8 (1998).Abstract Only.

Steele, L. et al., The Epidemiology of Chronic Fatigue in San Francisco. The American Journal of Medicine. vol. 105(3A), pp. 83S-90S (Sep. 28, 1998).

Shirachi, A. Therapeutic implication of interleukin-10 in inflammatory bowel disease. Kurume Med J. 45(1):63-7 (1998). Abstract Only.

Targan, S. et al. A short-term study of chimeric monoclonal antibody cA2 to tumor necrosis factor alpha for Crohn's Disease. The New England Journal of Medicine. vol. 337, No. 15 pp. 102935 (Oct. 9, 1997).

Targan, S et al., The Utility of ANCA and ASCA in Inflammatory Bowel Diseases, Inflammatory Bowel Disease, vol. 5, No. 1, pp. 61-63 (Feb. 1999).

Terman, M. et al. Chronic Fatigue syndrome and Seasonal Affective disorder: Comorbidity, diagnostic overlap and implications for treatment. The American Journal of Medicine. vol. 105(3A), pp. 115S-124S (Sep. 28, 1998).

Tirelli, U. et al. Brain Positron Emission Tomography (PET) in Chronic Fatigue Syndrome: Preliminary Data. The American Journal of Medicine. vol. 105(3A): pp. 54S-28S (Sep. 28, 1998).

Triadafilopoulos, G. et al. Bowel dystunction in fibromyalgia syndrome. Digestive Diseases and Sciences. vol. 36, No. 1, pp. 59-64 (Jan. 1991).

van den Berg, W.B. Joint inflammation and cartilage destruction may occur uncoupled, Springer Semin Immunopathol. 320(1-2): 149-64 (1998). Abstract Only.

Vanderhoof, J.A. et al. Treatment strategies for small bowel bacterial overgrowth in short bowel syndrome. J. Pediatr Gastroenterol Nutr 27(2); 155-60 (Aug. 1998). Abstract Only.

Vanderhoof, J.A. et al. Use of probiotics in childhood gastrointestinal disorders. J. Pediatr Gastroenterol Nutr 27(3): 323-32 (Sep. 1998). Abstract Only.

van Dulleman, H.M. et al. Treatment of Crohn's disease with anti-tumor necrosis factor chimeric monoclonal antibody (cA2), Gastroenterology, 109(1):129-35 (Jul. 1995). Abstract Only.

van Hogezand, R.A. et al. Selective immunomodulation in patients with inflammatory bowel disease-future therapy or reality? Neth J. Med. 48(2):64-7 (Feb. 1996). Abstract Only.

van Hogezand, R.A. et al. The future role of anti-tumour necrosis factor-alpha products in the treatmenr of Crohn's disease. Drugs. 56(3):299-305 (Sep. 1998). Abstract Only.

Varni, J.W. et al. Chronic Pain and Emotional Distress in Children and Adolescents. Dev. Behav. Ped. vol. 17, No. 3, pp. 154-161 (Jun. 1996).

Verkijk, M. et al. Effect of gastrin on antroduodenal motility: role of intraluminal acidity. Am J. Physiol. 274(5 PT 1): G1209-16. Abstract Only.

Weckmann, A.L. et al., Cytokine inhibitors in autoimmune disease, Semin Atthritis Rheum, 26(2):539-57 (Oct. 1996). Abstract Only.

Wolf, B.W. et al., Safety and tolerance of *Lactobacillus reuteri* supplementation to a population infected with the human immunodeficiency virus. Food Chem Toxicol. 36(12):1085-94 (Dec. 1998). Abstract Only.

Wolfe, F. et al. Aspects of Fibromyalgia in the General Population: Sex, Paid Threshold, and Fibromyalgia Symptoms. The Journal of Rheumatology. vol. 22, pp. 151-156 (1995).

Wolfe, F. Fibromyalgia: The Clinical Syndrome, Rheumatic Disease Clinics of North America. vol. 15, No. 1 pp. 1-17 (Feb. 1989).

Woo, P. Cytokines in juvenile chronic arthritis. Bailleres Clin Rheumatol. 12(2):219-28 (May 1998). Abstract Only.

Whiteside, T.L. et al. Natural Killer Cells and Natural Killer Cell Activity in chronic Fatigue Syndrome. The American Journal of Medicine. vol. 105(3A), pp. 27S-34S (Sep. 28, 1998).

U.S. Appl. No. 13/073,169 Restriction Requirement dated Sep. 2, 2011.

U.S. Appl. No. 13/073,189 Non-Final Office Action dated Oct. 21, 2011.

European Application No. 10177153.3 Examination Report dated Sep. 21, 2011.

European Application No. 10183213.7 Extended Search Report dated Sep. 30, 2011.

Canadian Application No. 2,444,548 Office Action dated Sep. 28, 2011.

European Application No. 10178066.6 Examination Report dated Jul. 11, 2011.

Stone et al. Lupus Erythematosus: Treatment with Penicillin. British Journal of Dermatology and Syphilis. (1946). 52 (5-6):122-123.

Weingarten et al. Meningitis Due to Penicillin-Resistant *Streptococcus pneumoniae* in Adults. Reviews of Infectious Diseases. (1990) 12(1):118-124.

METHODS OF DIAGNOSING AND TREATING SMALL INTESTINAL BACTERIAL OVERGROWTH (SIBO) AND SIBO-RELATED CONDITIONS

STATEMENT REGARDING FEDERALLY-SPONSORED RESEARCH

The U.S. Government has a paid-up license in this invention and the right in limited circumstances to require the patent owner to license others on reasonable terms as provided for by the terms of Grant No. DK46459 awarded by the National Institutes of Health.

This application claims the benefit of priority under 35 U.S.C. §120 as a continuation of U.S. patent application Ser. No. 12/768,531, filed on Apr. 27, 2010 and issued as U.S. Pat. No. 8,110,177 on Feb. 7, 2012, which is a continuation of U.S. application Ser. No. 11/348,995, filed Feb. 7, 2006 and issued as U.S. Pat. No. 7,736,622 on Jun. 15, 2010, which is a divisional of U.S. patent application Ser. No. 09/837,797, filed Apr. 17, 2001 and issued as U.S. Pat. No. 7,048,906 on May 23, 2006, which is a continuation-in-part of U.S. patent application Ser. No. 09/374,142, filed on Aug. 11, 1999 and issued as U.S. Pat. No. 6,861,053 on Mar. 1, 2005, a continuation-in-part of U.S. patent application Ser. No. 09/374,143, filed on Aug. 11, 1999 and issued as U.S. Pat. No. 6,562,629 on May 13, 2003, and a continuation-in-part of U.S. patent application Ser. No. 09/546,119, filed on Apr. 10, 2000 and issued as U.S. Pat. No. 6,558,708 on May 6, 2003.

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts. It relates to a method of diagnosing and treating small intestinal bacterial overgrowth (SIBO), and conditions caused by SIBO.

2. Discussion of the Related Art

Small intestinal bacterial overgrowth (SIBO), also known as small bowel bacterial overgrowth (SBBO), is an abnormal condition in which aerobic and anaerobic enteric bacteria from the colon proliferate in the small intestine, which is normally relatively free of bacterial contamination. SIBO is defined as greater than $10^6$ CFU/mL small intestinal effluent (Risk Donaldson, Jr., *Normal bacterial populations of the intestine and their relation to intestinal function*, N. Engl. J. Med. 270:938-45 [1964]). Typically, the symptoms include abdominal pain, bloating, gas and alteration in bowel habits, such as constipation and diarrhea.

Irritable bowel syndrome, Crohn's disease, chronic fatigue syndrome, chronic pelvic pain syndrome, fibromyalgia, depression, attention deficit/hyperactivity disorder, autism, and autoimmune diseases, e.g., multiple sclerosis and systemic-lupus erythematosus, are all clinical conditions of unclear etiology. No association has bee made heretofore between any of the afore-going diagnostic categories and SIBO.

Irritable bowel syndrome (IBS) is the most common of all gastrointestinal disorders, affecting 11-14% of adults and accounting for more than 50% of all patients with digestive complaints. (G. Triadafilopoulos et al., *Bowel dysfunction in fibromyalgia*, Digestive Dis. Sci. 36(1):59-64 [1991]; W. G. Thompsoir *Irritable Bowel syndrome: pathogenesis and management*, Lancet 341:1569-72 [1993]). It is thought that only a minority of people with IBS actually seek medical treatment. Patients with IBS present with disparate symptoms, for example, abdominal pain predominantly related to defecation, alternating diarrhea and constipation, abdominal distention, gas, and excessive mucus in the stool.

A number of possible causes for IBS have been proposed, but none has been fully accepted. (W. G. Thompson [1993]). These hypotheses included a fiber-poor Western diet, intestinal motility malfunction, abnormal pain perception, abnormal psychology or behavior, or psychophysiological response to stress.

A high fiber diet increases stool bulk and shortens gut transit time. However the presence of IBS in non-Western countries, such as China and India, and the failure of dietary fiber supplements to treat-IBS in double-blind clinical trials are inconsistent with the "fiber hypothesis" for the causation of IBS. (W. Bi-zhen and P. Qi-Ying, *Functional bowel disorders in apparently healthy Chinese people*, Chin. J. Epidemiol. 9:345-49 [1988]; K. W. Heaton, *Role of dietary fibre in irritable bowel syndrome*. In: R. W. Read [ed.], *Irritable bowel syndrome*, Grune and Stratton, London, pp. 203-22 [1985]; W. G. Thompson et al., *Functional bowel disorders and functional abdominal pain*, Gastroenterol. Int. 5:75-92 [1992]).

Those experiencing chronic IBS pain are often depressed and anxious. Treatment with tricyclic antidepressants has been used to raise the pain threshold of some IBS patients; (W. G. Thompson [1993]). Abreu et al. and Rabinovich et al. taught the use of corticotropin-releasing factor antagonists to relieve stress-related symptoms, including depression and anxiety, in IBS, anorexia nervosa, and other disorders. (M. E. Abreu, Corticotropin-releasing factor antagonism compounds, U.S. Pat. No. 5,063,245; A. K. Rabinovich et al., Benzoperimidine-carboxylic acids and derivatives thereof, U.S. Pat. No. 5,861,398). Becker et al. taught the use of serotonin antagonists to treat depression and anxiety associated with IBS and other conditions. (D. P. Becker et al., Meso-azacyclic aromatic acid amides and esters as serotonergic agents, U.S. Pat. No. 5,612,366).

Those with IBS symptoms have not been shown to have a different psychological or psychosocial make-up from the normal population. (W. E. Whitehead et al., *Symptoms of psychologic distress associated with irritable bowel syndrome: comparison of community and medical clinic samples*, Gastroenterol. 95:709-14 [1988]). But many IBS patients appear to perceive normal intestinal activity as painful. For example, IBS patients experience pain at lower volumes of rectal distention than normal or have a lower than normal threshold for perceiving migrating motor complex phase I activity. (W. E: Whitehead et al., *Tolerance for rectosigmoid distension in irritable bowel syndrome*, Gastroenterol. 98:1187-92 [1990]; J. E. Kellow et al., *Enhanced perception of physiological intestinal motility in the irritable bowel syndrome*, Gastroenterol. 101(6):1621-27 [1991]):

Bowel motility in IBS patients differs from normal controls in response to various stimuli such as drugs, hormones, food, and emotional stress. (D. G. Wangel and D. J. Deller, *Intestinal motility in man, III: mechanisms of constipation and diarrhea with particular reference to the irritable bowel*, Gastroentrol. 48:69-84 [1965]; R. F. Harvey and A. E. Read, *Effect of cholecystokinin on colon motility on and symptoms in patients with irritable bowel syndrome*, Lancet i:1-3 [1973]; R. M. Valori et al., *Effects of different types of stress and "prokinetic drugs" on the control of the fasting motor complex in humans*, Gastroenterol. 90:1890-900 [1986]).

Evans et al. and Gorard and Farthing recognized that irritable bowel syndrome is frequently associated with disordered gastro-intestinal motility. (P. R. Evans et al., *Gastroparesis and small bowel dysmotility in irritable bowel syndrome*, Dig. Dis. Sci. 42(10):2087-93 [1997]; D. A. Gorard and M. J. Farthing, *Intestinal motor function in irritable bowel syndrome*, Dig. Dis. 12(2):72-84 [1994]). Treatment directed to bowel dysmotility in IBS includes the use of serotonin antagonists (D. P. Becker et al., Meso-azacyclic aromatic acid amides and esters as serotonergic agents, U.S. Pat. No. 5,612,366; M. Ohta et al., Method of treatment of intestinal diseases, U.S. Pat. No. 5,547,961) and cholecystokinin antagonists (Y. Sato et al., Benzodiazepine derivatives, U.S. Pat. No. 4,970,207; H. Kitajima et al., Thienylazole compound and thienotriazolodiazepine compound, U.S. Pat. No. 5,760,032). But colonic motility index, altered myoelectical activity in the colon, and small intestinal dysmotility have not proven to be reliable diagnotic tools, because they are not IBS-specific: (W. G. Thompson [1993]).

Because there has been no known underlying cause for IBS, treatment of IBS has been primarily directed to symptoms of pain, constipation or diarrhea symptoms.

For example, administration of the polypeptide hormone relaxin, used to relax the involuntary muscles of the intestines, is a treatment taught to relieve the pain associated with IBS. (S. K. Yue, Method of treating myofascial pain syndrome with relaxin, U.S. Pat. No. 5,863,552).

Borody et al taught the use of a picosulfate-containing laxative preparation to treat constipation in IBS, small intestinal bacterial overgrowth, and acute or chronic bacterial bowel infections. (T. J. Borody et al., Picosulfate-containing preparation for colonic evacuation, U.S. Pat. No. 5,858,403). Barody also taught the use of an anti-inflammatory agent to treat IBS. (T. J. Barody, Treatment of non-inflammatory and non-infectious bowel disorders, U.S. Pat. No. 5,519,014). In addition, constipation in IBS has been treated with amidinourea compounds. (J. Yelnosky et al., Amidinoureas for treating irritable bowel syndrome, U.S. Pat. Nos. 4,701,457 and 4,611,011).

Kuhla et al. taught the use of triazinone compounds to relieve IBS symptoms of constipation, diarrhea, and abdominal pain (D. E. Kuhla et al., Triazinones for treating irritable bowel syndrome, U.S. Pat. No. 4,562,188). And Kitazawa et al. taught the use of napthy- and phenyl-sulfonylalkanoic acid compounds to treat IBS symptoms (M. Kitazawa et al., Naphthysulfonylalkanoic acid compounds and pharmaceutical compositions thereof, U.S. Pat. No. 5,177,069; M. Kitazawa et al., Phenylsulfonylalkanoic acid compounds and pharmaceutical compositions thereof, U.S. Pat. No. 5,145,869). Day taught an IBS treatment involving the administration of an anion-binding, polymer and a hydrophilic-polymer, (C. E. Day, Method for treatment of irritable bowel syndrome, U.S. Pat. No. 5,380,522). And Borody et al. taught the use of salicylic acid derivatives to treat IBS. (T. J. Borody et al., Treatment of non-inflammatory and non-infectious bowel disorders, U.S. Pat. No. 5,519,014).

A probiotic approach to the treatment of IBS has also been tried. For example, Allen et al. described the use of a strain of *Enterococcus faecium* to alleviate symptoms. (W. D. Allen et al., Probiotic containing *Enterococus faecium* strain NCIMB 40371, U.S. Pat. No. 5,728,380 and Probiotic, U.S. Pat. No. 5,589,168). Borody taught a method of treating irritable bowel syndrome by at least partial removal of the existing intestinal microflora by lavage and replacement with a new bacterial community introduced by fecal inoculum from a disease-screened human donor or by a composition comprising *Bacteroides* and *Escherichia coli* species. (T. J. Borody, Treatment of gastro-intestinal disorders with a fecal composition or a composition of *bacteroides* and *E. coli*, U.S. Pat. No. 5,443,826).

Fibromyalgia (FM) is a syndrome of intense generalized pain and widespread local tenderness, usually associated with morning stiffness, fatigue, and sleep disturbances. (F. Wolfe, *Fibromyalgia: the clinical syndrome*, Rheum. Dis. Clin. N. Amer. 15(1):1-17 [1989]). Fibromyalgia is often associated with IBS (34-50% of FM cases) or other gastrointestinal symptoms, Raynaud's phenomenon, headache, subjective swelling, paresthesias, psychological abnormality or functional disability, sometimes with overlapping symptoms of coexisting arthritis, lower back and cervical disorders, and tendonitis. Fibromyalgia affects 1-5% of the population and is more prevalent among women than men (G. Triadafilopoulos et al. [1991]).

As in IBS, a diagnosis of FM correlates with a decreased pain threshold among FM patients compared to non-patients. (F. Wolfe et al., *Aspects of Fibromyalgia in the General Population: Sex, Pain Threshold, and Fibromyalgia Symptoms*, J. Rheumatol. 22:151-56 [1995]). But other conventional laboratory evaluations of FM patients are uniformly normal. (G. Triadafilopoulos et al. [1991]). The symptoms of FM patients are typically treated with anti-inflammatory agents and low dose tricyclic antidepressants. Administration of relaxin for involuntary muscle dysfunction is also a treatment taught to relieve the pain associated with fibromyalgia. (S. K. Yue, Method of treating myofascial pain syndrome with relaxin, U.S. Pat. No. 5,863,552). However, there has been no known cause of FM to which diagnosis and/or treatment could be directed.

Chronic fatigue syndrome (CFS) affects more than a half million Americans. (P. H., Levine, *What we know about chronic fatigue syndrome and its relevance to the practicing physician*, Am. J. Med. 105(3A):100S-03S [1998]). Chronic fatigue syndrome is characterized by a sudden-onset of persistent, debilitating fatigue and energy loss that lasts at least six months and cannot be attributed to other medical or psychiatric conditions; symptoms include headache, cognitive and behavioral impairment, sore throat, pain in lymph nodes and joints, and low grade fever. (M. Terman et al., *Chronic Fatigue Syndrome and Seasonal; Affective Disorder: Comorbidity, Diagnostic Overlap, and Implications for Treatment*, Am. J. Med. 105(3A):115S-24S [1998]). Depression and related, symptoms are also common, including sleep disorders, anxiety, and worsening of premenstrual symptoms or other gynecological complications. (A. L. Komaroff and D. Buchwald, *Symptoms and signs of chronic fatigue syndrome*, Rev. Infect. Dis. 13:S8-S11 [1991]; B. L. Harlow et al., *Reproductive correlates of chronic fatigue syndrome*, Am. J. Med. 105(3A):94S-99S [1998]). Other physiologic abnormalities are also associated with CFS in many patients, including neurally-mediated hypotension, hypocortisolism, and immunologic dysregulation. (P. H. Levine [1998]). A subgroup of CFS patients complain of exacerbated mood state, diminished ability to work and difficulty awakening during winter months, reminiscent of seasonal affective disorder. (M. Terman et al. [1998]).

The etiology of CFS has been unknown, and the heterogeneity of CFS symptoms has precluded the use of any particular diagnostic laboratory test. (P. H. Levine [1998]). Symptomatic parallels have been suggested between CFS and a number of other disease conditions, resulting from viral infection, toxic exposure, orthostatic hypotension, and stress, but none of these has been shown to have a causal role in CFS. (E.g., I. R. Bell et al., *Illness from low levels of environmental chemicals: relevance to chronic fatigue syndrome and fibro-* myalgia, Am. J. Med. 105(3A):74S-82S [1998]; R. L. Bruno et al., *Parallels between post-polio fatigue and chronic fatigue syndrome: a common pathophysiology?*, Am. J. Med. 105(3A):66S-73S [1998]; R. Glaser and J. K. Kiecolt-Glaser; *Stress-associated immune modulation: relevance to viral infections and chronic fatigue syndrome*, Am. J. Med. 105 (3A):35S-42S. [1998]; P. C. Rowe and H. Calkins, *Neurally mediated hypotension and chronic fatigue syndrome*, Am. J. Med. 105(3A):15S21S [1998]; L. A. Jason et al., *Estimating the prevalence of chronic fatigue syndrome among nurses*, Am. J. Med. 105(3A):91S-93S [1998]). One study reported that there was no support for an etiological role in CFS of *Yersinia enterocolitica* infection. (C. M. Swanink et al., *Yersinia entercolitica and the chronic fatigue syndrome*, J. Infect. 36(3):269-72 [1998]). Accordingly, there has been no known cause to which diagnosis and/or treatment of CSF could be directed.

Consequently, the diagnosis and treatment of CFS have continued to be directed to symptoms, rather than to an underlying treatable cause. For example, the use of relaxin has been described for relaxing the involuntary muscles and thus relieve pain associated with CFS (S. K. Yue, Method of treating myofascial pain syndrome with relaxin, U.S. Pat. No. 5,863,552).

Attention deficit/hyperactivity disorder (ADHD) is a heterogeneous behavioral disorder of unknown etiology that always appears first in childhood, affecting 3-20% of elementary school-age children, and continues to affect up to 3% of adults. (Reviewed in L. L. Greenhill, *Diagnosing attention deficit/hyperactivity disorder in children*, J. Clin. Psychiatry 59 Suppl 7:31-41 [1998]). Those affected with ADHD symptoms typically exhibit inattentiveness and distractibility (AD type), hyperactive and impulsive behavior (HI type), or a combination of these, to a degree that impairs normal functioning and is often socially disruptive. (M. L. Wolraich et al., *Examination of DSM-IV criteria for attention deficit/hyperactivity disorder in a county-wide sample*, J. Dev. Behav. Pediatr. 19(3): 162-68 [1998]; J. J. Hudziak et al., *Latent class and factor analysis of DSM-IV ADHD: a twin study of female adolescents*, J. Am. Acad. Child Adolesc. Psychiatry 37(8): 848-57 [1998]). Often prescribed are central nervous system stimulants, tricyclic antidepressants, antihypertensives, analgesics, or antimanic drugs, but there has been no known cause of ADHD to which diagnosis and/or treatment could be directed. (S. C. Schneider and G. Tan, *Attention deficit/hyperactivity disorder. In pursuit of diagnostic accuracy*, Postgrad. Med. 101(4):231-2, 235-40 [1997]; W. J. Barbaresi, *Primary-care approach to the diagnosis and management of attention deficit/hyperactivity disorder*, Mayo Clin. Proc. 71(5):463-71 [1996]).

There has also been no known cause for autoimmune diseases, including multiple sclerosis and systemic lupus erythematosus. Multiple sclerosis (MS) is a neurologic disease that primarily strikes teens and young adults under 35 years. Affecting 350,000 Americans, MS is the most: frequent cause of neurologic disability except for traumatic injuries; MS affects twice as many females compared to males. (S. L. Hauser, *Multiple Sclerosis and other demyelinating diseases In: Harrison's Principles of Internal Medicine*, 13th ed., K. J. Isselbacher et al. (eds.), McGraw-Hill, pp. 2287-95 [1994]). The disease is characterized by chronic inflammation, scarring, and selective destruction of the myelin sheath around neural axons of the central nervous system, and is thought to be caused by autoimmune responses. A treatment for MS taught by Weiner et al. is related to oral administration of autoantigens to the patient to suppress the autoimmune response by eliciting suppressor T-cells specific for myelin basic protein (MBP). There are no specific diagnostic tests for MS; diagnosis is based on clinical recognition of destructive patterns of central nervous system injury that are produced by the disease. (S. L. Hauser [1994]) Nerve damage may be mediated by cytokines, especially TNF-α, which has been found to be selectively toxic to myelin and to oligodendrocytes in vitro. Elevated levels of TNF-α and IL-2 were measured in MS patients. (J. L. Trotter et al., *Serum cytokine levels in chronic progressive multiple sclerosis: interleukin-2 levels parallel tumor necrosis factor-alpha levels*, J. Neuroimmunol. 33(1):29-36 [1991]; H. L. Weiner et al., Treatment of multiple sclerosis by oral administration of autoantigens, U.S. Pat. No. 5,869,054). Another treatment for MS involves the administration of a vitamin D compound. (H. F. DeLuca et al., Multiple sclerosis treatment, U.S. Pat. No. 5,716,946). However, there has been no known cause of MS to which diagnosis and/or treatment could be directed.

Systemic lupus erythematosus (SLE) is an autoimmune rheumatic disease characterized by deposition in tissues of autoantibodies and immune complexes leading to tissue injury (B. L. Kotzin, *Systemic lupus erythematosus*, Cell 85:303-06 [1996]). In contrast to autoimmune diseases such as MS and type 1 diabetes mellitus, SLE potentially involves multiple organ systems directly, and its clinical manifestations are diverse and variable. (Reviewed by B. L. Kotzin and J. R. O'Dell, *Systemic lupus erythematosus, In: Samler's Immunologic Diseases*, 5th ed., M. M. Frank et al., eds., Little Brown & Co., Boston, pp. 667-97 [1995]). For example, some patients may demonstrate primarily skin rash and joint pain, show spontaneous remissions, and require little medication. At the other end of the spectrum are patients who demonstrate severe and progressive kidney involvement that requires therapy with high doses of steroids and cytotoxic drugs such as cyclophosphamide. (B. L. Kotzin [1996]):

The serological hallmark of SLE, and the primary diagnostic test available, is elevated serum levels of IgG antibodies to constituents of the cell nucleus, such as double-stranded DNA (dsDNA); single-stranded DNA (ss-DNA), and chromatin. Among these autoantibodies, IgG anti-dsDNA antibodies play a major role in the development of lupus glomerulonephritis (GN). (B. H. Hahn and B. Tsao, *Antibodies to DNA, In: Dubois Lupus Erythematosus*, 4th ed., D. J. Wallace and B. Hahn, eds, Lea and Febiger, Philadelphia, pp. 195-201 [1993]; Ohnishi et al., *Comparison of pathogenic and non-pathogenic murine antibodies to DNA: Antigen binding and structural characteristics*, Int. Immunol. 6:817-30 [1994]). Glomerulonephritis is a serious condition in which the capillary walls of the kidney's blood purifying glomeruli become thickened by accretions on the epithelial side of glomerular basement membranes. The disease is often chronic and progressive and may lead to eventual renal failure.

The mechanisms by which autoantibodies are induced in these autoimmune diseases remains unclear. As there has been no known cause of SLE, to which diagnosis and/or treatment could be directed, treatment has been directed to suppressing immune responses, for example with macrolide antibiotics, rather than to an underlying cause. (E.g., Hitoshi et al., Immunosuppressive agent, U.S. Pat. No. 4,843,092).

Another disorder for which immunosuppression has been tried is Crohn's disease. Crohn's disease symptoms include intestinal inflammation and the development of intestinal stenosis and fistulas; neuropathy often accompanies these symptoms. Anti-inflammatory drugs, such as 5-aminosalicylates (e.g., mesalamine) or corticosteroids, are typically prescribed, but are not always effective. (Reviewed in V. A. Botoman et al., *Management of Inflammatory Bowel Disease*, Am. Fam. Physician 57(1):57-68 [1998]). Immunosuppression with cyclosporine is sometimes beneficial for patients resistant to or intolerant of corticosteroids. (J. Brynskov et al., *A placebo-controlled double-blind randomized trial of cyclosprorine therapy, inactive chronic Crohn's disease*, N. Engl. J. Med. 321(13):845-50 [1989]).

Nevertheless, surgical correction is eventually required in 90% of patients; 50% undergo colonic resection. (K. Leiper et al., *Adjuvant post-operative therapy*, Baillieres Clin. Gastroenterol. 12(1):179-99 [1998]; F. Makowiec et al., *Long-term follow-up after resectional surgery in patients with Crohn's disease involving the colon*, Z. Gastroenterol. 36(8):619-24 [1998]). The recurrence rate after surgery is high, with 50% requiring further surgery within 5 years. (K. Leiper et al. [1998]; M. Besnard et al., *Postoperative outcome of Crohn's disease in 30 children*, Gut 43(5):634-38 [1998]).

One hypothesis for the etiology of Crohn's disease is that a failure of the intestinal mucosal barrier, possibly resulting from genetic susceptibilities and environmental factors (e.g., smoking), exposes the immune system to antigens from the intestinal lumen including bacterial and food antigens (e.g., Söderholm et al., *Epithelial permeability to proteins in the non-inflamed ileum of Crohn's disease?*, Gastroenterol. 117:65-72 [1999]; D. Hollander et al., *Increased intestinal permeability in patients with Crohn's disease and their relatives. A possible etiologic factor*, Ann. Intern. Med. 105:883-85 [1986]; D. Hollander, *The intestinal permeability barrier. A hypothesis to its involvement in Crohn's disease*, Scand. J. Gastroenterol. 27:721-26 [1992]). Another hypothesis is that persistent intestinal infection by pathogens such as *Mycobacterium paratuberculosis, Listeria monocytogenes*, abnormal *Escherichia coli*, or paramyxovirus, stimulates the immune response; or alternatively, symptoms result from a dysregulated immune response to ubiquitous antigens, such as normal intestinal microflora and the metabolites and toxins they produce. (R. B. Sartor, *Pathogenesis and Immune Mechanisms of Chronic Inflammatory Bowel Diseases*, Am. J. Gastroenterol. 92(12):5S-11S [1997]). The presence of IgA and IgG anti-*Saccharomyces cerevisiae* antibodies (ASCA) in the serum was found to be highly diagnostic of pediatric Crohn's disease. (F. M. Ruemmele et al., *Diagnoitic accuracy of serological assays in pediatric inflammatory bowel disease*, Gastroenterol. 115(4):822-29 [1998]; E. J. Hoffenberg et al., *Serologic testing for inflammatory bowel disease*, J. Pediatr. 134(4):447-52 [1999]).

In Crohn's disease, a dysregulated immune response is skewed toward cell-mediated immunopathology. (S. I. Murch, *Local and systemic effects of macrophage cytokines in intestinal inflammation*, Nutrition 14:780-83 [1998]). But immunosuppressive drugs, such as cyclosporine, tacrolimus, and mesalamine have been used to treat corticosteroid-resistant cases of Crohn's disease with mixed-success. (J. Brynskov et al [1989]; K. Fellerman et al., *Steroid-unresponsive acute attacks of inflammatory bowel disease: immunomodulation by tacrolimus* [FK506], Am. J. Gastroenterol. 93(10):1860-66 [1998]). An abnormal increase in colonic permeability is also seen in patients with Crohn's disease. (Vermeire S. et al., *Anti-Saccharomyces cerevisiae antibodies (ASCA), phenotypes of IBD, and intestinal permeability: a study in IBD families*, Inflamm Bowel Dis. 7(1):8-15 [2001]).

Recent efforts to develop diagnostic and treatment tools against Crohn's disease have focused on the central role of cytokines. (S. Schreiber, *Experimental immunomodulatory therapy of inflammatory bowel disease*, Neth. J. Med. 53(6):S24-31 [1998]; R. A. van Hogezand and H. W. Verspaget, *The future role of anti-tumour necrosis factor-alpha products in the treatment of Crohn's disease*, Drugs 56(3):299-305 [1998]). Cytokines are small secreted proteins or factors (5 to 20 kD) that have specific effects on cell-to-cell interactions, intercellular communication, or the behavior of other cells. Cytokines are produced by lymphocytes, especially $T_H1$ and $T_H2$ lymphocytes, monocytes, intestinal macrophages, granulocytes, epithelial cells, and fibroblasts. (Reviewed in G. Rogler and T. Andus, *Cytokines in inflammatory bowel disease*, World J. Surg. 22(4):382-89 [1998]; H. F. Galley and N. R. Webster, *The immuno-inflammatory cascade*, Br. J. Anaesth. 77:11-16 [1996]). Some cytokines are pro-inflammatory (e.g., tumor necrosis factor [TNF]-α, interleukin [IL]-1 (α and β), IL-6, IL-8, IL-12, or leukemia inhibitory factor [LIF]); others are anti-inflammatory (e.g., IL-1 receptor antagonist [IL-1ra], IL-4, IL-10, IL-11, and transforming growth factor [TGF]-β). However, there may be overlap and functional redundancy in their effects under certain inflammatory conditions.

In active cases of Crohn's disease, elevated concentrations of TNF-α and IL-6 are secreted into the blood circulation, and TNF-α, IL-1, IL-6, and IL-8 are produced in excess locally by mucosal cells. (Id.; K. Funakoshi et al., *Spectrum of cytokine gene expression in intestinal mucosal lesions of Crohn's disease and ulcerative colitis*, Digestion-59(1):73-78 [1998]). These cytokines can have far-ranging effects on physiological systems including bone development, hematopoiesis, and liver, thyroid, and neuropsychiatric function. Also, an imbalance of the IL-1β/IL-1ra ratio, in favor of pro-inflammatory IL-1β, has been observed in patients with Crohn's disease. (G. Rogler and T. Andus [1998]; T. Saiki et al., *Detection of pro- and anti-inflammatory cytokines in stools of patients with inflammatory bowel disease*, Scand. J. Gastroenterol. 33(6):616-22 [1998]; S. Dionne et al., *Colonic explant production of IL-1 and its receptor antagonists is imbalanced in inflammatory bowel disease (IBD)*, Clin. Exp. Immunol. 112 (3):435-42 [1998]; But see S. Kuboyama, *Increased circulating levels of interleukin-1 receptor antagonist in patients with inflammatory bowel disease*, Kurume Med. J. 45(1):33-37 [1998]). One study suggested that cytokine profiles in stool samples could be a useful diagnostic tool for Crohn's disease. (T. Saiki et al. [1998]).

Treatments that have been proposed for Crohn's disease, include the use of various cytokine antagonists (e.g., IL-1ra), inhibitors (e.g., of IL-1β converting enzyme and antioxidants) and anti-cytokine antibodies. (G. Rogler and T. Andus [1998]; R. A. van Hogezand and H. W. Verspaget [1998]; J. M. Reimund et al., *Antioxidants inhibit the in vitro production of inflammatory cytokines in Crohn's disease and ulcerative colitis*, Eur. J. Clin. Invest. 28(2):145-50 [1998]; N. Lugering et al., *Current concept of the role of monocytes/macrophages in inflammatory bowel disease-balance of pro-inflammatory and immunosuppressive mediators*, Ital. J. Gastroenterol. Hepatol, 30(3):338-44 [1998]; M. E. McAlihdon et al., *Expression of interleukin 1 beta and interleukin 1 beta converting enzyme by intestinal macrophages in health and inflammatory bowel disease*, Gut 42(2):214-19 [1998]). In particular, monoclonal antibodies against TNF-α have been tried with some success in the treatment of Crohn's disease. (S. R. Targan et al., *A short-term study of chimeric monoclonal antibody cA2 to tumor necrosis factor alpha for Crohn's disease. Crohn's Disease cA2 Study Group*, N. Engl. J. Med. 337(15):1029-35 [1997]; W. A. Stack et al., *Randomised controlled trial of CDP571 antibody to tumour necrosis factor-alpha in Crohn's disease*, Lancet 349(9051):521-24 [1997]; H. M. van Dullemen et al., *Treatment of Crohn's disease with anti-tumor necrosis factor chimeric monoclonal antibody (cA2)*, Gastroenterol. 109(1):129-35 [1995]).

Another approach to the treatment of Crohn's disease has focused on at least partially eradicating the bacterial community that may be triggering the inflammatory response and replacing it with a non-pathogenic community. For example, McCann et al. (McCann et al., Method for treatment of idiopathic inflammatory bowel disease, U.S. Pat. No. 5,599,795) disclosed a method for the prevention and treatment of Crohn's disease in human patients. Their method was directed to sterilizing the intestinal tract with at least one antibiotic and at least one anti-fungal agent to kill off the existing flora and replacing them with different, select, well-characterized bacteria taken from normal humans. Borody taught a method of treating Crohn's disease by at least partial removal of the existing intestinal microflora by lavage and replacement with a new bacterial community introduced by fecal inoculum from a disease-screened human donor or by a composition comprising *Bacteroides* and *Escherichia coli* species. (T. J. Barody, Treatment of gastro-intestinal disorders with a fecal composition or a composition of *bacteroides* and *E. coli*, U.S. Pat. No. 5,443,826). However, there has been no known cause of Crohn's disease to which diagnosis and/or treatment could be directed.

Pain is a common symptom associated with irritable bowel syndrome, fibromyalgia, chronic fatigue syndrome, chronic pelvic pain syndrome, depression, ADHD, autoimmune diseases, and Crohn's disease. While the experience of pain is intertwined with a person's emotions, memory, culture, and psychosocial situation (D. A. Drossman and W. G. Thompson, *Irritable bowel syndrome: a graduated multicomponent treatment approach*, Ann. Intern. Med. 116:1009-16 [1992]), evidence shows that certain cytokine mediated-immune responses can influence the perception of pain. Cytokines can be released in response to a variety of irritants and can modulate the perception of pain. For example, exposure of human bronchial epithelial cells to irritants, including acidic pH, results in a receptor-mediated release of inflammatory cytokines IL-6, IL-8, and TNF-α (B. Veronesi et al., *Particulate Matier initiates inflammatory cytokine release by activation of capsaicin and acid receptors in a human bronchial epithelial cell line*, Toxicol. Appl. Pharmacol: 154:106-15 [1999]). Irritant receptors on cell surfaces, e.g., receptors sensitive to noxious stimuli, such as capsaicin and pH, mediate the release of cytokines and also mediate the release of neuropeptides from sensory nerve fibers, which is known to result in a neurogenic inflammatory processes and hyperalgesia (excessive sensitivity to pain). (Id.; R.O.P. de Campos et al., *Systemic treatment with Mycobacterium bovis bacillus calmett-guerin (BCG) potentiates kinin $B_1$ receptor agonist-induced nociception and oedema formation in the formalin test in mice*, Neuropeptides 32(5):393-403 [1998]).

The perception of pain, is also influenced by the mediation of kinin $B_1$ and $B_2$ receptors, which bind peptides called kinins, e.g., the nonapeptide bradykinin or the decapeptide kallidin (lysyl bradykinin). While the precise mechanism of action is unknown, kinins cause the release of other pro-inflammatory and hyperalgesic mediators such as neuropeptides. Cytokines IL-1 (α and β), IL-2, IL-6, and TNF-α are thought to activate kinin $B_1$ receptor, and thus can contribute to enhanced perception of pain. (R.O.P. de Campos et al. [1998]. The endotoxin of *Escherichia coli* significantly activated kinin $B_1$ receptor-mediated neurogenic and inflammatory pain responses in animals. (M. M. Campos et al., *Expression of $B_1$ kinin receptors mediating paw oedema formalin-induced nociception. Modulation by glucocorticoids*, Can. J. Physiol. Pharmacol. 73:812-19 [1995]).

It has also been shown that IL-1β, IL-6, and TNF-α, administered to the mammalian brain, can modulate pain perception via prostaglandin-dependent processes. (T. Hori et al., *Pain modulatory actions of cytokines and prostaglandin $E_2$ in the Brain*, Ann. N.Y. Acad. Sci. 840:269-81 [1998]). Granulocytes, which accumulate in nearly all forms of inflammation, are non-specific amplifiers and effectors of specific immune responses, and they can also modulate the perception of pain. Neutrophils, a type of granulocyte cell, are known to accumulate in response to IL-1β, and neutrophil accumulation plays a crucial positive role in the development of nerve growth factor (NGF)-induced hyperalgesia. (G. Bennett et al., *Nerve growth factor induced hyperalgesia in the rat hind paw is dependent on circulating neutrophils*, Pain 77(3):315-22 [1998]; see also E. Feher et al., *Direct morphological evidence of neuroimmunomodulation in colonic mucosa of patients with Crohn's disease*, Neuroimmunomodulation 4(5-6):250-57 [1997]).

Visceral hyperalgesia, or pain hypersensitivity, is a common clinical observation in small intestinal bacterial overgrowth (SIBO), Crohn's disease, chronic pelvic pain syndrome, and irritable bowel syndrome (IBS). As many as 60% of subjects with IBS have reduced sensory thresholds for rectal distension compared to normal subjects. (H. Mertz et al., *Altered rectal perception is a biological marker of patients with the irritable bowel syndrome*, Gastroenterol.109:40-52 [1995]). While the experience of pain is intertwined with a person's emotions, memory, culture, and psychosocial situation (D. A. Drossman and W. G. Thompson, *Irritable bowel syndrome: a graduated multicomponent treatment approach*, Ann. Intern. Med. 116:1009-16 [1992]) and the etiology for this hyperalgesia has remained elusive, evidence shows that certain cytokine mediated-immune responses can influence the perception of pain. Cytokines, including IL-1(α and β), IL-2, IL-6, and TNF-α, can be released in response to a variety of irritants and can modulate the perception of pain, possibly through the mediation of kinin $B_1$ and/or $B_2$ receptors (see, M. M. Campos et al., *Expression of $B_1$ kinin receptors mediating paw oedema formalin-induced nociception. Modulation by glucocorticoids*, Can. J. Physiol. Pharmacol. 73:812-19 [1995]; R.O.P. de Campos et al., *Systemic treatment with Mycobacterium bovis bacillus calmett-guerin (BCG) potentiates kinin $B_1$ receptor agonist-induced nociception and oedema formation in the formalin test in mice*, Neuropeptides 32(5):393-403 [1998]). Cytokine and neuropeptide levels are altered in IBS. An increase in substance P (neuropeptide)-sensitive nerve endings has been observed in subjects with IBS. (X. Pang et al., *Mast cell substance P-positive nerve involvement in a patient with both irritable bowel syndrome and interstitial cystitis*, Urology 47:436-38 [1996]). It has also been hypothesized that there is a sensitization of afferent pathways in IBS. (E. A. Mayer et al., *Basic and clinical aspects of visceral hyperalgesia*, Gastroenterol 1994; 107:271-93 [1994]; L. Bueno et al., *Mediators and pharmacology of visceral sensitivity: from basic to clinical investigations*, Gastroenterol. 112:1714-43 [1997]).

Fibromyalgia, typically involving global musculoskeletal and/or cutaneous pain, is, by definition; a hyperalgesic state since the American College of Rheumatology defines fibromyalgia as a history of global pain in the setting of 11 out of 18 predefined tender points. (F. Wolfe et al., *The American College of Rheumatology 1990 criteria for the classification of fibromyalgia*, Arthritis Rheum. 33:160-72 [1990]). Evidence implies that the hyperalgesia of fibromyalgia is not simply trigger point-related but rather a global hyperalgesia. (L. Vecchiet et al., *Comparative sensory evaluation of parietal tissues in painful and nonpainful areas in fibromyalgia and myofascial pain syndrome*, In: Gebhart G F, Hammond D L, Jensen. T S, editors, *Progress in Pain Research and Management*, Vol. 2, Seattle: IASP Press, pp. 177-85 [1994]; J Sorensen et al., *Hyperexcitability in fibromyalgia*, J. Rheumatol. 25:152-55 [1998]).

Cytokine and neuropeptide levels are altered in IBS, fibromyalgia, and Crohn's disease. It has been shown that levels of substance P, a neuropeptide: associated with nociception, are elevated in the cerebrospinal fluid of subjects with fibromyalgia. (H. Vaeroy et al., *Elevated CSF levels of substance P and high incidence of Raynaud's phenomenon in patients with fibromyalgia: new features for diagnosis*, Pain 32:21-26 [1988]; I. J. Russell et al., *Elevated cerebrospinal fluid levels of substance P in patients with the fibromyalgia syndrome*, Arthritis Rheum. 37:1593-1601 [1994]). And an increase in substance P-sensitive nerve endings has been observed in subjects with IBS and Crohn's disease, (X. Pang et al., *Mast cell substance P-positive nerve involvement in a patient with both irritable bowel syndrome and interstitial cystitis*, Urology 47:436-38 [1996]; (C. R. Mantyh et al., *Receptor binding sites for substance P, but not substance K or neuromedin K, are expressed in high concentrations by arterioles, venules, and lymph nodules in surgical specimens obtained from patients with ulcerative colitis and Crohn's disease*, Proc. Natl. Acad. Sci. 85:3235-39 [1988]; S. Mazumdat and K. M. Das, *Immunocytochemical localization of vasoactive intestinal peptide and substance P in the colon from normal subjects and patients with inflammatory bowel disease*, Am. J. Gastrol 87:176-81 [1992]; C. R. Mantyh et al., *Differential expression of substance P receptors in patients with Crohn's disease and ulcerative colitis*, Gastroenterol. 1995; 109:850-60 [1995]).

Patients with chronic pelvic pain are usually evaluated and treated by gynecologists, gastroenterologists, urologists, and internists, but in many patients with chronic pelvic pain the examination and work-up remain unrevealing, and no specific cause of the pain, such as endometriosis, can be identified. In these cases the patient is commonly said to be suffering from a "chronic pelvic pain syndrome." Once the diagnosis of chironic pelvic pain is made, treatment is typically directed to symptomatic pain management, rather than to an underlying cause. (Wesselmann U, Czakanski P P, *Pelvic pain: a chronic visceral pain syndrome*, Curr. Pain Headache Rep. 5(1): 13-9 [2001]).

Mental functioning and feelings of fatigue or depression can also be influenced by immune responses. Peripherally released pro-inflammatory cytokines, such as IL-1, IL-6 and TNF-α, act on brain cellular targets and have been shown to depress spontaneous and learned behavior in animals; the vagus nerve has been shown to mediate the transmissions of the immune message to the brain, resulting in production of pro-inflammatory cytokines centrally in the brain. (R. Dantzer et al., *Cytokines and sickness behavior*, Ann. N.Y. Acad. Sci. 840:586=90 [1998]). In addition, there is bidirectional interplay between neurotransmitters and the immune system; lymphocytes and macrophages bear surface receptors for the stress hormone corticotrophin releasing hormone (CRH), and they respond to CRH by enhanced lymphocyte proliferation and feedback upregulation of hypothalamic CRH production. (S. H. Murch [1998]).

Pituitary production of proopiomelanocortins, such as endorphins and enkephalins, is upregulated by IL-1 and IL-2, possibly mediated by CRH, and lymphocytes and macrophages recognize these endogenous opiates via surface receptors. (S. H. Murch [1998]) Lymphocytes ($T_H2$) and macrophages also produce and process enkephalin to an active form, Macrophage-derived cytokines, such as TNF-α, IL-1, and IL-6, are known to modulate neurotransmitter release and to affect overall neural activity; cytokines can induce classic illness behavior such as somnolence, apathy, depression, irritability, confusion, poor memory, impaired mental concentration, fever and anorexia.

While immunological responses: of various; severities can lead to symptoms characteristic of irritable bowel syndrome, fibromyalgia, chronic pelvic pain syndrome, chronic fatigue syndrome, impaired mentation and/or memory, depression, autism, ADHD; autoimmune diseases, and Crohn's disease, there has been a definite need to determine a causal factor, for each of these diagnostic categories, to which diagnostic testing and treatment can be directed effectively.

SIBO has, until recently, mostly been suspected in subjects with significant malabsorptive sequelae. Most of the described cases of SIBO involve anatomic alterations such as physical obstruction (E. A. Deitch et al., *Obstructed intestine as a reservoir for systemic infection*, Am. J. Surg. 159:394 [1990]), surgical changes (e.g., L. K. Enander et al., *The aerobic and anaerobic microflora of the gastric remnant more than 15 years after Billroth II resection*, Scand. J. Gastroenterol. 17:715-20 [1982]); direct communication of the small intestine with colonic contents such as fistulae (O. Bergesen et al., *Is vitamin B12 malabsorption in bile fistula rats due to bacterial overgrowth? A study of bacterial metabolic activity in the small bowel*, Scand. J. Gastroenterol. 23:471-6 [1988]) and ileocecal valve dysfunction (surgical or otherwise) (W. O. Griffin, Jr, et al., *Prevention of small bowel contamination by ileocecal valve*, S. Med. J: 64: 1056-8. [1971]; P. Rutgeerts et al., *Ileal dysfunction and bacterial overgrowth inpatients with Crohn's disease*, Eur, J. Clin. Invest. 11:199-206 [1981]). Less commonly, SIBO has been associated with chronic pancreatitis (E. Trespi and A. Ferrieri, *Intestinal bacterial overgrowth during chronic pancreatitis*, Curr. Med. Res. Opin. 15:47-52 [1999]), hypochlorhydria (e.g., S. P. Pereira et al., *Drug-induced hypochlorhydria causes high duodenal bacterial counts in the elderly*, Aliment. Pharmacol. Ther. 12:99-104 [1998]), and immunodeficiency (C. Pignata et al., *Jejunal bacterial overgrowth and intestinal permeability in children with immunodeficiency syndromes*, Gut 31:879-82 [1990]; G. M. Smith et al., *Small intestinal bacterial overgrowth in patients with chronic lymphocytic leukemia*, J. Clin. Pathol. 43:57-9 [1990]).

SIBO has been associated with infections of the abdominal cavity in cases of alcoholic cirrhosis. (F. Casafont Morencos et al, *Small bowel bacterial overgrowth in patients with alcoholic cirrhosis*, Dig. Dis: Sci. 40(6): 1252-1256 [1995]; J. Chesta et al., *Abnormalities in proximal small bowel motility in patients with cirrhosis*, Hepatology 17(5):828-32 [1993]; C. S. Chang et al., *Small intestine dysmotility and bacterial overgrowth in cirrhotic patients with spontaneous bacterial peritonitis*, Hepatology 28(5): 1187-90 [1998]). SIBO has also been associated with symptoms of chronic diarrhea, anorexia or nausea in elderly patients, and the prevalence of overgrowth in subjects over 75 years old is reported to be as high as 79% even in the absence of clinically evident clues of overgrowth or achlorhydria. (S. M. Riordan et al., *Small intestinal bacterial overgrowth in the symptomatic elderly*, Am. J. Gastroenterol. 92(1):47-51 [1997]). SIBO is also associated with chronic digestive symptoms in children, especially infants under two years of age (D. De Boissieu et al., *Small-bowel bacterial overgrowth in children with chronic digestive diarrhea, abdominal pain, or both*, J. Pediatr. 128(2):203-07 [1996]), and with chronic diarrhea after liver transplantation in children. (D. R. Mack et al., *Small bowel bacterial overgrowth as a cause of chronic diarrhea after liver transplantation in children*, Liver Transpl. Surg: 4(2): 166-69 [1998]):

Although diabetic enteropathy (F. Goldstein et al., *Diabetic diarrhea and steatorrhea Microbiologic and clinical* observations, Ann. Intern. Med. 1970; 72:215-8 [1970]), idiopathic intestinal pseudo-obstruction (A. J. Pearson et al., *Intestinal pseudo-obstruction with bacterial overgrowth in the small intestine*, Am. J. Dig. Dis. 14:200-05 [1969]) and scleroderma (I. J. Kahn et al., *Malabsorption in intestinal scleroderma: Correction with antibiotics*, N. Engl. J. Med. 274: 1339-44 [1966]) are all known to produce motility disturbances leading to SIBO. Two previous reports have examined small bowel motility among anatomically and medically naive SIBO subjects. (G. Vantrappen et al., *The interdigestive motor complex of normal subjects and patients with bacterial overgrowth of the small intestine*, J. Clin. Invest. 59: 1158-66 [1977]; P. O, Stotzer et al., *Interdigestive and postprandial motility in small-intestinal bacterial overgrowth*, Scand: J. Gastroenterol. 31:875-80 [1996]). These authors suggest that the majority of subjects with SIBO in the absence of other predisposing conditions, lack the phase III of interdigestive motility during short term recordings.

Phase III of interdigestive motility is a period of phasic contractions propagating through the length of the small intestine, approximately once every $87.2 \pm 5.4$ minutes in the fasting state. (E. E. Soffer et al., *Prolonged ambulatory duodeno-jejunal manometry in humans: Normal values and gender effect*, Am. J. Gastrol. 93:1318-23 [1998]). This fasting event is responsible for sweeping residue including, small bowel contaminants, such as accumulated bacteria, into the colon in preparation for the next meal. (V. B. Nieuwenhujuijs et al., *The role of interdigestive small bowel motility in the regulation of gut microflora, bacterial overgrowth, and bacterial translocation in rats*, Ann. Surg. 228: 188-93 [1998]; E. Husebye, *Gastrointestinal motility disorders and bacterial overgrowth*, J. Intern. Med. 237:419-27 [1995]). The endogenous peptide, motilin, is involved in the mediation of this event. (G. Vantrappen et al., *Motilin and the interdigestive migrating motor complex in man*, Dig. Dis. Sci. 24:497-500 [1979]). Other prokinetic agents, such as erythromycin, are believed to act on the motilin receptor and have been shown to rapidly induce an interdigestive motility event in dogs and humans. (M. F. Otterson and S. K. Sarna, *Gastrointestinal motor effect of erythromycin*, Am. J. Physiol. 259:G355-63; T. Tomomasa et al., *Erythromycin induces migrating motor complex in human gastrointestinal tract*, Dig. Dis. Sci. 31:157-61 [1986]).

In general, the speed of transit through the small intestine is normally regulated by inhibitory mechanisms located in the proximal and distal small intestine known as the jejunal brake and the ileal brake. Inhibitory feedback is activated to slow transit when end products of digestion make contact with nutrient sensors of the small intestine. (E.g., Lin, H. C., U.S. Pat. No. 5,977,175; Dobson, C. L. et al., *The effect of oleic acid on the human ileal brake and its implications for small intestinal transit of tablet formulations*, Pharm. Res. 16(1): 92-96 [1999]; Lin, H. C. et al., *Intestinal transit is more potently inhibited by fat in the distal (Ileal brake) than in the proximal (jejunal brake) gut*, Dig. Dis. Sci. 42(1):19-25 [1997]; Lin, H. C. et al., *Jejunal brake: inhibition of intestinal transit by fat in the proximal small intestine*, Dig. Dis. Sci., 41(2):326-29 [1996a]).

Specifically, jejunal and ileal brakes slow transit by the release of gut peptides such as peptide YY and by the activation of neural pathways such as those involving endogenous opioids. (Lin, H. C. et al., *Fat-induced ileal brake in the dog depends on peptide YY*, Gastroenterol. 110(5):1491-95 [1996b]). Transit is then slowed by the stimulation of non-propagative intestinal contractions which inhibit movement of the lumenal content. The removal or impairment of these inhibitory mechanisms can lead to abnormally rapid transit. For example, in patients with a history of resection of the terminal ileum, intestinal transit can become uncontrolled and abnormally accelerated when the ileal brake is no longer intact. Time for processing of food can then be so reduced that few end products of digestion are available to trigger the jejunal brake as the remaining inhibitory mechanism.

Peptide YY and its analogs or agonists have been used to manipulate endocrine regulation of cell proliferation, nutrient transport, and intestinal water and electrolyte secretion. (E.g., Balasubramantiam, Analogs of peptide yy and uses thereof, U.S. Pat. No. 5,604,203; WO9820885A1; EP692971A1; Croom et al., Method of enhancing nutrient uptake, U.S. Pat. No. 5,912,227; Litvak, D. A. et al., *Characterization of two novel proabsorptive peptide YY analogs, BIM-43073D and BIM-43004C*, Dig. Dis. Sci. 44(3):643-48 [1999]). A role for peptide YY in the regulation of intestinal motility, secretion, and blood flow has also been suggested, as well as its use in a treatment of malabsorptive disorders (Liu, C. D. et al, *Peptide YY: a potential proabsorbtive hormone for the treatment of malabsorptive disorders*, Am. Surg. 62(3):232-36 [1996]; Liu, C. D. et al., Intralumenal peptide YY induces colonic absorption in vivo, Dis. Colon Rectum 40(4):478-82 [1997]; Bilchik, A. J. et al., *Peptide YY augments postprandial small intestinal absorption in the conscious dog*, Am. J. Surg. 167 (6):570-74 [1994]).

Lin et al. immuno-neutralized peptide YY in vivo to block the ileal brake response and, thus, showed that it is mediated by peptide YY. (Lin, H. C. et al., *Fat-induced ileal brake in the dog depends on peptide YY*, Gastroenterology, 110(5):1491-95 [1996b]). Serum levels of peptide YY increase during the ileal brake response to nutrient infusion into the distal ileum. (Spiller, R. C. et al, *Further characterisation of the 'ileal brake' reflex in man-effect of ileal infusion of partial digests of fat, protein, and starch on jejunal motility and release of neurotensin, enteroglucagon, and peptide YY*, Gut, 29(8): 1042-51 [1988]; Pironi, L. et al., *Fat-induced ileal brake in humans: a dose-dependent phenomenon correlated to the plasma levels of peptide YY.*, Gastroenterology, 105(3):733-9 [1993]; Dreznik, Z. et al., *Effect of ileal oleate on interdigestive intestinal motility of the dog*, Dig. Dis. Sci., 39(7):1511-8 [1994]; Lin, C. D. et al., *Interlumenal peptide YY induces colonic absorption in vivo*, Dis. Colon Rectum, 40(4):478-82 [April 1997]). In contrast, in vitro studies have shown peptide YY infused into isolated canine ileum dose-dependently increased phasic circular muscle activity. (Fox-Threlkeld, J. A. et al., *Peptide YY stimulates circular muscle contractions of the isolated perfused canine ileum by inhibiting nitric oxide release and enhancing acetylcholine release*, Peptides, 14(6): 1171-78 [1993]).

Kreutter et al. taught the use of $\beta_3$-adrenoceptor agonists and antagonists for the treatment of intestinal motility disorders, as well as depression, prostate disease and dyslipidemia (U.S. Pat. No. 5,627,200).

Bagnol et al. reported the comparative immunovisualization of mu and kappa opioid receptors in the various cell layers of the rat gastrointestinal tract, including a comparatively large number of kappa opioid receptors in the myenteric plexus. (Bagnol, D. et al., *Cellular localization and distribution of the cloned mu and kappa opioid receptors in rat gastrointestinal tract*, Neuroscience, 81(2):579-91 [1997]). They suggested that opioid receptors can directly influence neuronal activity in the gastrointestinal tract.

Kreek et al. taught the use of opioid receptor antagonists, such as naloxone, naltrexone, and nalmefene, for the relief of gastrointestinal dysmotility. (Kreek et al., Method for controlling gastrointestinal dysmotility, U.S. Pat. No. 4,987,136). Riviere et al. taught the use of the opioid receptor antagonist fedotozine in the treatment of intestinal obstructions (Riviere, P. J. M. et al., U.S. Pat. No. 5,362,756). Opioid-related constipation, the most common chronic adverse effect of opioid pain medications in patients who require long-term opioid administration, such as patients with advanced cancer or participants in methadone maintenance, has been treated with orally administered methylnaltrexone and naloxone. (Yuan, C. S. et al., *Methylnaltrexone for reversal of constipation due to chronic methadone use: arandomized controlled trial*, JAMA 283(3):367-72 [2000]; Meissner, W. et al., *Oral naloxone reverses opioid-associated constipation*, Pain 84(1):105-9 [2000]; Culpepper-Morgan, J. A., et al., Treatment of opioid-induced constipation with oral naloxone: a pilot study, Clin. Pharmacol. Ther. 52(1):90-95 [1992]; Yuan, C. S. et. al., *The safety and efficacy of oral methylnaltrexone in preventing morphine-induced delay in oral-cecal transit time*, Clin. Pharmacol. Ther. 61(4):467-75 [1997]; Santos, F. A. et. al, *Quinine-induced inhibition of gastrointestinal transit in mice: possible involvement of endogenous opioids*, Eur. J. Pharmacol., 364(2-3):193-97 [1999]. Naloxone was also reported to abolish the ileal brake in rats (Brown, N. J. et al., *The effect of an opiate receptor antagonist on the ileal brake mechanism in the rat*, Pharmacology, 47(4):230-36 [1993.]).

Receptors for 5-hydroxytryptamine (5-HT) have been localized on various cells of the gastrointestinal tract. (Gershon, M. D., *Review article: roles played by 5-hydroxytryptamine in the physiology of the bowel*, Aliment. Pharmacol. Ther., 13 Suppl 2:15-30 [1999]; Kirchgessner, A. L. et al., *Identification of cells that express 5-hydroxytryptamine 1A receptors in the nervous systems of the bowel and pancreas*, J. Comp. Neurol., 15:364(3):439-455 [1996]). Brown et al. reported that subcutaneous administration of 5-HT3 receptor antagonists, granisetron and ondansetron, in rats delayed intestinal transit of a baked bean meal but abolished the ileal brake induced by ileal infusion of lipid. They postulated the presence of 5-HT3 receptors on afferent nerves that initiate reflexes that both accelerate and delay intestinal transit. (Brown, N. J. et al., *Granisetron and ondansetron: effects on the ileal brake mechanism in the rat*, J. Pharm Pharmacol. 45(6):521-24 [1993]). Kuemmerle et al. reported neuroendocrine 5-HT-mediation of motilin-induced accelerated gastrointestinal motility. (Kuemmerle, J. F. et al., *Serotonin neural receptors mediate motilin-induced motility in isolated vascularly perfused canine jejunum*, J. Surg. Res., 45(4):357-62 [1988]).

Ninety-five percent of the human body's stores of 5-hydroxyltryptamine (5-HT), also known as serotonin, are found in the gastrointestinal tract. (Gershon, M. D., *The Second Brain*, New York: Harper Collins [1998]). In the intestines, the vast majority of 5-HT is located in the enterochromaffin (EC) cells of the mucosa (Gershon [1998]). 5-HT is also released by myenteric 5-HT neurons in the myenteric plexus. (Gershon, M. D., *The enteric nervous system*, Annu Rev Neurosci 4: 227-272 [1981]; Gershon, M. D. et al., *Serotonin: synthesis and release from the myenteric plexus of the mouse intestine*, Science 149: 197-199 [1965]; Holzer, P., and G. Skofitsch, *Release of endogenous 5-hydroxytryptamine from the myenteric plexus of the guinea-pig isolated small intestine*, Br J Pharmacol 81: 381-386 [1984]; Penttila, A., *Histochemical reactions of the enterochromaffin cells and the 5-hydroxytryptamine content of the mammalian duodenum*, Acta Physiol Scand Suppl 281: 1-77 [1966]). These intrinsic 5-HT neurons receive input from parasympathetic and sympathetic fibers (Gershon, M. D., and D. L Sherman, *Noradrenergic innervation of serotoninergic neurons in the myenteric plexus*, J Comp Neurol 259: 193-210 [1987]) and provide input to the motor neurons in their vicinity to suggest that they are interneurons. 5-HT3 receptors are widely expressed by these: myenteric 5-HT neurons as well as their neighboring neurons (Galligan, J. J., *Electrophysiological studies of 5-hydroxytryptamine receptors on enteric neurons*, Behav Brain Res 73: 199-201 [1996]; Zhou, X., and J: J. Galligan, *Synaptic activation and properties of 5-hydroxytryptamine*(3) *receptors in myenteric neurons of guinea pig intestine*, J Pharmacol Exp Ther 290: 803-10 [1999]). However, the physiologic function of these myenteric 5-HT neurons is not known. (E. G., Gershon, M. D. *Review article: roles played by 5-hydroxytryptamine in the physiology of the bowel*, Aliment Pharmacol Ther 13 Suppl 2: 15-30, 1999]; Grider, J. R. et al., *5-HT released by mucosal stimuli initiates peristalsis by activating 5-HT4/5-HT1p receptors on sensory CGRP neurons*, Am J Physiol 270: G778-G782 [1996]).

Regardless of the source of 5-HT (mucosal vs. neuronal or both), the signaling role of this molecule is facilitated by the availability of a 5FIT reuptake transporter called SERT that terminates the signal with its removal. (Wade, P. R. et al., *Localization and function of a 5-HT transporter in crypt epithelia of the gastrointestinal tract*, J Neurosci 16: 2352-64 [1996]). Since SERT is a part of the plasma membrane of serotonergic neurons (Blakely, R. D. et al., *Cloning and expression of a functional serotonin transporter from rat brain*, Nature 354: 66-70 [1991]), these transporters are ideally positioned to remove neuronal 5-HT after signaling is completed. Serotonergic nerves are, however, absent from the intestinal mucosa (Furness, J. B., aid M. Costas, *The enteric nervous system*, New York: Churchill Livingston [1987]). Instead, mucosal 5-HT from EC cells is removed by SERT expressed by neighboring epithelial cells. (Chen, J. X. et al., *Guinea pig 5-HT transporter: cloning, expression, distribution, and function in intestinal sensory reception*, Am J Physiol 275: G433-G448 [1998]).

The action of SERT is blocked by drugs that inhibit the reuptake transporter. These serotonin-selective reuptake inhibitors (SSRI) are widely used as antidepressants. The most commonly prescribed example is fluoxetine (Prozac). These agents significantly alter the peristaltic response. Wade et al. reported that fluoxetine initially accelerated the passage of a pellet through an isolated segment of guinea pig colon to suggest potentiation of the peristaltic effect of 5-HT when the removal of this molecule was inhibited (Wade et al. [1996]). However, as the dose of the SSRI was increased, the transit of the pellet became slower and slower. This observation with fluoxetine suggested to Gershon that 5-HT receptors became desensitized when an excess of 5-HT stayed around for a longer period of time and traversed further away from its mucosal source (Gershon [1998]). These are then the current concepts to explain the common gastrointestinal side effects of SSRIs including nausea (excess 5-HT acting on extrinsic sensory nerves) and diarrhea (excess 5-HT acting on intrinsic primary afferent neurons to initiate peristalsis; Gershon [1998]).

The current scientific foundation for understanding the role of serotonin in normal and abnormal motility of the small intestine has been based on the role of mucosal serotonin in two enteric functions. The first is as the neurotransmitter, via the activation of intrinsic primary afferent neurons (IPAN), for the peristaltic reflex, which mediates colonic evacuation, and for the mucosal secretory reflex. (E.g., Grider, J. R. et al., *5-Hydroxytryptamine*4 *receptor agonists initiate the peristaltic reflex in human, rat, and guinea pig intestine*, Gastroenterology, 115(2):370-80 [1998]; Jin, J. G. et al., *Propulsion in guinea pig colon induced by 5-hydroxytryptamine* (*HT*) *via 5-HT4 and 5-HT3 receptors*, J. Pharmacol. Exp. Ther., 288 (1):93-97 [1999]; Foxx-Orenstein, A. E. et al., *5-HT4 recep-*

*tor agonists and delta-opioid receptor antagonists act synergistically to stimulate colonic propulsion*, Am J. Physiol., 275(5 Pt. 1):G979-83 [1998]; Foxx-Orenstein, A. E., *Distinct 5-HT receptors mediate the peristaltic reflex induced by mucosal stimuli in human and guinea pig intestine*, Gastroenterology 111(5):1281-90 [1996]; Wade, P. R. et al., *Localization and function of a 5-HT transporter in crypt epithelia of the gastrointestinal tract*, J. Neurosci., 16(7):2352-64 [1996]; Grinder, J., *Gastrin-releasing peptide (GRP) neuron are excitatory neurons in the descending phase of the peristaltic reflex*, Gastroenterology 116: A1000 [1999]; Cooke, H., M. Sidhu, and Y. Wang, *5-HT activates neural reflexes regulating secretion in the guinea pig colon*, Neurogastroenterol Motil 9: 181-6 [1997]; Cooke, H. J., and H. V. Carey, *Pharmacological analysis of 5-hydroxytryptamine actions on guinea-pig ileal mucosa*, Eur J Pharmacol 111: 329-37, [1985]; Frieling, T., J. Wood, and H. Cooke, *Submucosal reflexes: distension-evoked ion transport in the guinea pig distal colon*, Am J. Physiol 263: G91-96 [1992]; Hardcastle, J., and P. Hardcastle, *Comparison of the intestinal secretory responses to 5-hydroxytryptamine in the rat jejunum and ileum in-vitro*, J Pharm Pharmcacol 49: 1126-31 [1997]; Kinsman, R. I., and N. W. Read, *Effect of naloxone on feedback regulation of small bowel transit by fat*, Gastroenterology 87: 335-337 [1984]).

The second enteric role for 5-HT is as the signal to the brain about lumenal conditions, linking mucosal stimuli with the brain via extrinsic primary sensory neurons. (Blackshaw, L. A., and D. Grundy, *Effects of 5-hydroxytryptamine on-discharge of vagal mucosal afferent fibres from the upper gastrointestinal tract of the ferret*, J Auton Nerv Syst 45: 41-50 [1993]). On the basis of this understanding, concepts have evolved to explain the irritable bowel syndrome as a condition of serotonin excess (leading to diarrhea from excessive peristalsis) (Gershon [1998]), even as the constipation typical of this syndrome remains puzzling. Similar explanations have also been used to explain the diarrhea reported by patients taking SSRI (e.g. Prozac).

The intestinal response to 5-HT has previously been described in terms of the peristaltic reflex in in vitro models. Bulbring and Crema first showed that lumenal 5-HT resulted in peristalsis. (Bulbring et al., J. Physiol. 140:381-407 [1959]; Bulbring et al., Brit. J. Pharm. 13:444-457 [1958]). Since the stimulation of peristalsis by 5-HT was unaffected by extrinsic denervation (Bulbring et al., QJ Exp. Physiol. 43:26-37 [1958]), the peristaltic reflex was considered to be intrinsic to the enteric nervous system. Using a modified Trendelenburg model that compartmentalized the peristaltic reflex into the sensory limb, the ascending contraction limb (orad to stimulus) and the descending relaxation limb (aborad to stimulus), Grider, et al. reported that (1) mucosal stimulation but not muscle stretch released 5-HT to activate a primary sensory neuron to release calcitonin gene-related peptide (CGRP) (Grider et al., Am. J. Physiol. 270:G778-G782 [1996]) via 5-HT4 receptors in humans and rats (also 5-HT1p in rats) and 5-HT3 receptors in guinea pigs; (2) cholinergic interneurons are then stimulated by CGRP to initiate both ascending contraction via an excitatory motor neuron that depends on substances P and K and acetylcholine (Grider et al., Am. J. Physiol. 257:G709-G714 [1989]) and descending relaxation (Grider, Am. J. Physiol. 266:G1139-G1145 [1994]; Grider et al. [1996], Jin et al., J. Pharmacol. Exp. Ther. 288:93-97 [1999]) via an inhibitory motor neuron that depends on pituitary adenylate cyclase-activating peptide (PACAP), nitric oxide and vasoactive inhibitory peptide (VIP) (Grider et al., Neuroscience 54:521-526 [1993]; Grider et al., J. Auton. Nerv. Syst. 50:151-159 [1994]); and (3) peristalsis is controlled by [a] an opioid pathway that inhibits descending relaxation by suppressing the release of VIP; [b] a somatostatin pathway that inhibits this opioid pathway (Grider, Am. J. Physiol. 275:G973-G978 [1998]); and [c] a GABA (Grider, Am. J. Physiol. 267:G696-G701 [1994]) and a gastrin releasing peptide (GRP) (Grider, Gastroenterol. 116:A1000 [1999]) pathway that stimulate VIP release. An opioid pathway that inhibits the excitatory motor neurons responsible for ascending contraction has also been described (Gintzler et al., Br. J. Pharmacol. 75:199-205 [1982]; Yau et al., Am. J. Physiol. 250:G60-G63 [1986]). These observations are consistent with neuroanatomic and electrophysiological observations.

In addition, mucosal stroking has been found to induce 5-HT release by intestinal mucosal cells, which in turn activates a 5-HT4 receptor on enteric sensory neurons, evoking a neuronal reflex that stimulates chloride secretin (Kellum, J. M. et al., *Stroking human jejunal mucosa induces 5-HT release and Cl$^-$ secretion via afferent neurons and 5-HT4 receptors*, Am. J. Physiol. 277(3 Pt 1):G515-20 [1999]).

Agonists of 5-HT4/5, 5-HT3 receptors, as well as opioid Δ receptor antagonists, were reported to facilitate peristaltic propulsive activity in the colon in response to mechanical stroking, which causes the endogenous release of 5-HT and calcitonin gene-related protein (CGRP) in the stroked mucosal area. (Steadman, C. J. et al., *Selective 5-hydroxytrypamine type 3 receptor antagonism with ondansetron as treatment for diarrhea-predominant irritable bowel syndrome: a pilot study*, Mayo Clin. Proc. 67(8):732-38 [1992]). Colonic distension also results in CGRP secretion, which is associated with triggering the peristaltic reflex, 5-*HT3 receptor antagonists have been used for the treatment of autism.* (E.g., Oakley et al., 5-HT3 receptor antagonists for the treatment of autism, U.S. Pat. No. 5,225,407).

Improved methods of detecting or diagnosing SIBO and SIBO-caused conditions are also a desideratum. Typically, detection of SIBO is done by detecting hydrogen and/or methane exhaled in the breath. (E.g., P. Kerlin and L. Wong, *Breath hydrogen testing in bacterial overgrowth of the small intestine*, Gastroenterol 95(4):982-88 [1988]; A. Strocchi et al., *Detection of malabsorption of low doses of carbohydrate: accuracy of various breath $H_2$ criteria*, Gastroenterol. 105 (5):1404-1410 [1993]; D. de Boissieu et al., [1996]; P. J. Lewindon et al., *Bowel dysfunction in cystic fibrosis: importance of breath testing*, J. Paedatr. Child Health 34(1):79-82 [1998]). Hydrogen is a metabolic product of the fermentation of carbohydrates and amino acids by bacteria normally found in the colon. While the hydrogen that is produced in the colonic lumen may be excreted via the lungs (exhaled breath) and the anus (flatus), these routes of excretion are responsible for the elimination of only a fraction of the total amount of hydrogen (10%) that is produced in the gut (Levitt, M. D. et al., *Hydrogen ($H_2$) catabolism in the colon of the rat*, J Lab clin Med 84:163-167 [1974]).

The major mechanism for the removal of hydrogen produced by bacterial fermentation is the utilization of this gas by colonic bacteria that competes to use hydrogen via one of three hydrogen disposal pathways that are mutually exclusive. These pathways depend on the metabolism of methanogenic bacteria (Levitt, M. D. et al., $H_2$ *excretion after ingestion of complex carbohydrates*, Gastroenterology 92:383-389 [1987]), acetogenic bacteria (Lajoie, R. et al., *Acetate production from hydrogen and [c13] carbon dioxide by the microflora of human feces*, Appl Environ Microbiol 54:2723-2727 [1988]) and sulfate-reducing bacteria. (Gibson, G. R. et al., *Occurrence of sulphate-reducing bacteria in human faeces and the relationship of dissimilatory sulphate reduc-* tion to metlanogenesis in the large gut, J Appl Bactereriol 65:103-111 [1988]). Methanogenic bacteria are more efficient than the other colonic bacteria in the elimination of lumenal hydrogen. (Strocchi, A. et al., *Methanogens outcompete sulphate reducing bacteria for $H_2$ in the human colon*, Gut 35-1098-1101 [1994]). Acetogenic bacteria are uncommon, being found in the intestinal populations of <5% of humans.

In the colon, sulfate-reducing bacteria reduces sulfate to hydrogen sulfide. (MacFarlane, G. T. et al., *Comparison of fermentation reactions in different regions of the human colon*, J Appl Bacteriol 72:57-64 [1992]). Hydrogen sulfide is more damaging to tissues than anionic sulfide or sulfhydryl compounds. Intestinal bicarbonate facilitates the conversion of hydrogen sulfide produced by sulfate-reducing bacteria in the gut to anionic sulfide. (Hamilton Wash.: *Biocorrosion: The action of sulphate-reducing bacteria, in Biochemistry of Microbial Degradation*, C. Ratlidge (ed.) Dordrecht, Kluwer Academic Publishers, pages 555-570 [1994]). Since sulfate-reducing bacteria are more-common in patients with the diagnosis of ulcerative colitis (Pitcher, M. C. L. et al., *Incidence and activities of sulphate-reducing bacteria in gut contents of healthy subjects and patients with ulcerative colitis*, FEMS Microbiol Ecol 86:103-11-2 [1991]), sulfate-reducing bacteria have been considered for a possible role in the pathogenesis of ulcerative colitis. (Florin, R. H. J. et al., *A role for sulfate reducing bacteria in ulcerative colitis?*, Gastroenterology 98:A170 [1990]). This link has been postulated to be related to the injurious effect of hydrogen sulfide in impairing the use of short chain fatty acids as fuel by colonic epithelial cells. (Roediger, W. E. W. et al., *Sulphide impairment of substrate oxidation in rat colonocytes: a biochemical basis for ulcerative colitis?*, Clin Sci 85:623-627 [1993]; Roediger, W. E. et al., *Reducing sulfur compounds of the colon impair colonocyte nutrition: implication of ulcerative colitis*, Gastroenterology 1993, 104:802-809).

Currently, clinical detection of sulfur-containing gases is limited to the detection of halitosis or bad breath. (Rosenberg, M. et. al., *Reproducibility and sensitivity of oral malodor measurements with a protable sulphide monitor*, J Dent Res. 1991 November; 70(11): 1436-40). After garlic ingestion, the presence of allyl methyl sulfide differentiates the intestine rather than the mouth as the source of the sulfur-containing volatile gas (Suarez, F. et al., *Differentiation of mouth versus gut as site of origin of odoriferous breath gases after garlic ingestion*, Am J Physiol 276(2 pt 1):G425-30 [1999]).

The role of sulfate-reducing bacteria in small intestinal bacterial overgrowth has not been studied, and the presence of sulfate-reducing bacteria are not detected using the standard breath testing method which typically detects only the presence of hydrogen, methane and carbon dioxide.

There remains a need for an underlying causal factor, to which diagnostic testing and treatment can be directed, for SIBO and SIBO-caused conditions, such as irritable bowel syndrome fibromyalgia; chronic pelvic pain syndrome; chronic fatigue syndrome; autism; depression; impaired, mentation and/or memory; sugar craving; ADHD; MS, SLE and other autoimmune diseases; and Crohn's disease. This and other benefits of the present invention are described herein.

SUMMARY OF THE INVENTION

The present invention relates to the diagnosis or treatment of small intestinal bacterial overgrowth (SIBO) and SIBO-caused conditions. SIBO-caused conditions, as described herein, include irritable bowel syndrome (IBS), Crohn's disease (CD), fibromyalgia (FM) chronic pelvic pain syndrome (CPPS), chronic fatigue syndrome (CFS), depression, impaired mentation, impaired memory, halitosis, tinnitus, sugar craving, autism, attention deficit/hyperactivity disorder (ADHD), drug sensitivity, and autoimmune diseases, for example, multiple sclerosis (MS), systemic lupus erythematosus (SLE).

In particular, the present invention relates to a method of treating small intestinal bacterial overgrowth (SIBO) or a SIBO-caused condition in a human subject. The method involves detecting in the subject by any suitable detection means, the presence or absence of SIBO in the subject. If SIBO is detected in the subject, the method further involves depriving the bacterial population, which constitutes the overgrowth in the small intestine, of nutrient(s), sufficiently to inhibit the further growth of the bacteria in the small intestine. With the growth of the bacteria constituting the SIBO condition thus inhibited, SIBO is at least partially eradicated, as the subject's phase III interdigestive motility is better able to clear the small intestine of the overgrowth and sweep the bacteria into the colon for eventual elimination from the body. In addition, the at least partial eradication of the SIBO condition also decreases the occurrence or magnitude of bacteria-related toxicity, sepsis (in more severe or advanced SIBO), and/or the subject's own immune responses, which are continually triggered by the presence of SIBO in non-immunocompromised subjects. The clinical symptoms of the subject associated with SIBO or the SIBO-caused condition are, consequently, ameliorated by the at least partial eradication of SIBO.

In an alternative aspect of the present invention, the method involves, inhibiting the growth of the bacteria in the subject's small intestine, which bacteria constitute a SIBO condition that has been detected, by introducing into the lumen of the small intestine, a pharmaceutically acceptable disinfectant or antibiotic composition in an amount sufficient to inhibit the growth of the bacteria, thereby at least partially eradicating SIBO in the human subject.

In still another alternative-aspect of the present invention, the method of treating small intestinal bacterial overgrowth (SIBO), or a SIBO-caused condition, in a human subject involves administering to the subject a pharmaceutically acceptable composition comprising a stabilizer of mast cell membranes in the lumenal wall, in an amount sufficient to inhibit a mast cell-mediated immune response to SIBO in the human subject.

The present invention also relates to a method of screening for the abnormally likely presence of SIBO in a human subject. The method involves obtaining a serum sample from the subject, and then quantitatively determining a concentration in the serum sample of serotonin, one or more unconjugated bile acid(s), and/or folate. An abnormally elevated serum concentration of one or more of these substances is indicative of a higher than normal probability that SIBO is present in the subject. Thus, if the method of screening for the presence of SIBO is employed as part, of a blood work-up, either as part of a routine physical or by way of investigating a particular clinical complaint of the subject's, the practitioner can be made aware that SIBO is more than normally likely to be present. The practitioner can then elect to pursue a less convenient, but more diagnostically powerful, detection means for SIBO.

The present invention also relates to such a diagnostically powerful SIBO detection means. In particular, this inventive method of detecting small intestinal bacterial overgrowth in a human subject involves detecting the relative amounts of methane, hydrogen, and at least one sulfur-containing gas in a gas mixture exhaled by the human subject, after the subject has ingested a controlled quantity of a substrate. The exhaled gas mixture is at least partially produced by the metabolic activity of the intestinal microflora of the subject.

The present invention is also directed to a method of determining the relative severity of SIBO or a SIBO-caused condition in a human subject in whom SIBO has been detected. The method involves detecting in the subject by suitable detection means, the presence or absence of SIBO, and, if the presence of SIBO is detected in the subject, the method further involves detecting in the subject by suitable detection means a relative level of intestinal permeability, abnormally high intestinal permeability indicating a relatively severe SIBO or SIBO-caused condition in the subject.

The present invention also relates to a kit for the diagnosis of SIBO or a SIBO-caused condition, comprising: at least one breath sampling container, a pre-measured amount of a substrate, and instructions for a user in detecting the presence or absence of SIBO by determining the relative amounts of methane, hydrogen, and at least one sulfur-containing gas in a gas mixture exhaled by the subject, after ingestion of a controlled quantity of the substrate. Thus, the kit is particularly useful in practicing the inventive method of detecting small intestinal bacterial overgrowth in a human subject.

These and other advantages and features of the present invention will be described more fully in a detailed description of the preferred embodiments which follows.

The present invention is further described by the disclosures of related U.S. applications: U.S. patent application Ser. No. 09/374,142, filed on Aug. 11, 1999 and issued as U.S. Pat. No. 6,562,629 on May 13, 2003; U.S. patent application Ser. No. 09/546,119, filed on Apr. 10, 2000 and issued as U.S. Pat. No. 6,558,708 on May 6, 2003; U.S. patent application Ser. No. 09/420,046, filed on Oct. 18, 1999, now abandoned; U.S. patent application Ser. No. 09/359,583, filed on Jul. 22, 1999, now abandoned; U.S. patent application Ser. No. 08/832,307, filed on Apr. 3, 1997 and issued as U.S. Pat. No. 5,977,175 on Nov. 2, 1999; and U.S. patent application Ser. No. 08/442,843, filed on May 17, 1995, now abandoned, which are all incorporated by reference.

DETAILED DESCRIPTION OF THE PREFERRED EMBODIMENTS

Figure 1:
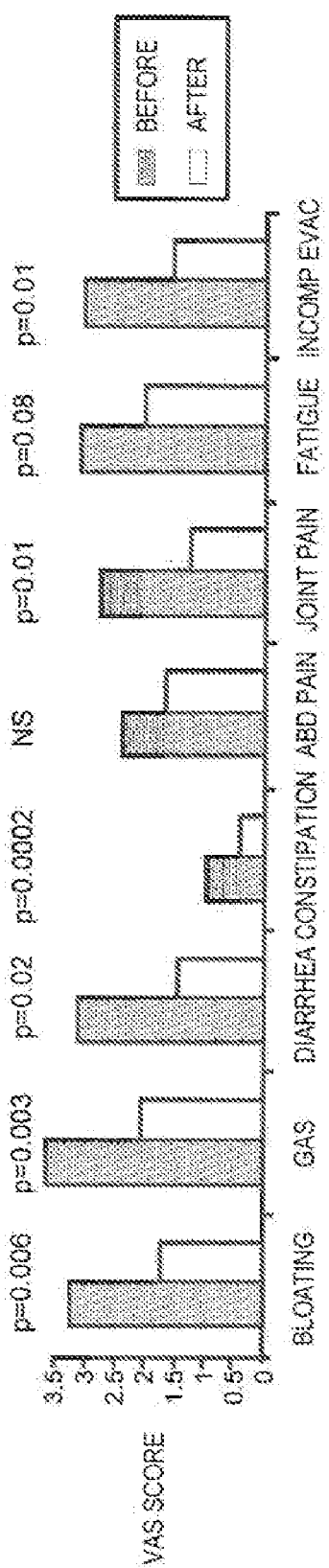
FIG. 1 shows visual analog scores reported by subjects with IBS and SIBO before and after antibiotic treatment.

The present invention is directed to a method of treating small intestinal bacterial overgrowth (SIBO) or a SIBO-caused condition in a human subject, including a juvenile or adult, of any age or sex.

The upper gastrointestinal tract of a human subject includes the entire alimentary canal, except the cecum, colon, rectum, and anus. While some digestive processes, such as starch hydrolysis, begin in the mouth and esophagus, of particular importance as sites of digestion are the stomach and small intestine (or "small bowel"). The small intestine includes the duodenum, jejunum, and the ileum. As the term is commonly used in the art, the proximal segment of the small bowel, or proximal gut, comprises approximately the first half of the small intestine from the pylorus to the mid-gut. The distal segment, or distal gut includes approximately the second half, from the mid-gut to the ileal-cecal valve.

As used herein, "digestion" encompasses the process of breaking down large biological molecules into their smaller component molecules, for example, proteins into amino acids. "Predigested" means that the process of digestion has already begun or has occurred prior to arrival in the upper gastrointestinal tract.

As used herein, "absorption" encompasses the transport of a substance from the intestinal lumen through the barrier of the mucosal epithelial cells into the blood and/or lymphatic systems.

Small intestinal bacterial overgrowth (SIBO), is an abnormal condition in which aerobic and anaerobic enteric bacteria from the colon proliferate in the small intestine, which is normally relatively free of bacterial contamination. SIBO is defined as greater than $10^6$ CFU/mL small intestinal effluent. (R. M. Donaldson, Jr., *Normal bacterial populations of the intestine and their relation to intestinal function*, N. Engl. J. Med. 270:938-45 [1964]).

Typically, the symptoms of SIBO include abdominal pain, bloating, gas and alteration in bowel habits, such as constipation and diarrhea. SIBO-caused conditions is used herein interchangeably with the term "SIBO-related conditions," and regardless of ultimate causation, is a condition associated with the presence of SIBO in the subject. SIBO-caused conditions include other common symptoms, such as halitosis ("bad breath"), tinnitus (the experience of noise in the ears, such as ringing, buzzing, roaring, or clicking, which may not be associated with externally produced sounds), sugar craving, i.e., an intense desire for sweet foods or flavors, which can result in abnormally large consumption of sweet foods and beverages and frequently leads to health-threatening obesity. Drug sensitivity is another common SIBO-caused condition, in which the subject is hypersensitive to medications, such as non-steroidal anti-inflammatory medications, anti-insomniacs, antibiotics, or analgesics, and can suffer an unpredictable allergic-type reaction to medications at doses that normally do not adversely affect the vast majority of patients. It is a benefit provided by the present invention that it provides a useful solution in the present tense, for many patients, to the problem of drug sensitivity, without requiring complex pharmacogenetic research and customized drug development.

Other SIBO-caused conditions, as described herein, can include those falling in the diagnostic categories of irritable bowel syndrome, Crohn's disease, fibromyalgia, chronic pelvic pain syndrome, chronic fatigue, syndrome, depression, impaired mentation (including impairment of the ability to concentrate, calculate, compose, reason, and/or use foresight or deliberate judgment), impaired memory, autism, attention deficit/hyperactivity disorder, and/or autoimmune diseases, such as systemic lupus erythematosus (SLE) or multiple sclerosis (MS).

In accordance with the invention, the SIBO-caused condition can be, but need not be, previously diagnosed or suspected. The skilled medical practitioner is aware of suitable up-to-date diagnostic criteria by which a suspected diagnosis is reached. These diagnostic criteria are based on a presentation of symptom(s) by a human subject. For example, these criteria include, but are not limited to, the Rome criteria for IBS (W. G. Thompson, *Irritable bowel syndrome: pathogenesis and management*, Lancet 341:1569-72 [1993]) and the criteria for CFS established by the Centers for Disease Control and Prevention (CDC). (K. Fukuda et al., *The chronic fatigue syndrome: a comprehensive approach to its definition and study*, Ann. Intern. Med. 121:953-59 [1994]). The diagnostic criteria for fibromyalgia of the American College of Rheumatology will also be familiar (F. Wolfe et al., *The American College of Rheumatology 1990 Criteria for the Classification of Fibromyalgia: Report of the Multicenter Criteria Committee*, Arthritis Rheum. 33:160-72 [1990]), as will be the criteria for depression or ADHD provided for example, by the Diagnostic and Statistical Manual (DSM)-IV or its current version. (E.g., G. Tripp et al, *DSM-IV and ICD-10: a comparison of the correlates of ADHD and hyperkinetic disorder*, J. Am. Acad. Child Adolesc. Psychiatry 38(2):156-64 [1999]). Symptoms of systemic lupus erythematosus include the 11 revised criteria of the American College of Rheumatology, such as a typical malar or discoid rash, photosensitivity, oral ulcers, arthritis, serositis, or disorders of blood, kidney or nervous system (E. M Tan et al., *The 1982 revised criteria for the classification of systemic lupus erythematosus [SLE]*, Arthritis Rheum. 25:1271-77 [1982]). Appropriate diagnostic criteria for multiple sclerosis are also familiar (e.g., L. A. Rolak, *The diagnosis of multiple sclerosis*, Neuronal Clin. 14(1):27-43 [1996]), as are symptoms of Crohn's disease useful in reaching a suspected diagnosis. (e.g., J. M. Bozdech ad R. G. Farmer, *Diagnosis of Crohn's disease*, Hepatogastroenterol. 37(1):8-17 [1990]; M. Tanaka and R. H. Riddell, *The pathological diagnosis and differential diagnosis of Crohn's disease*, Hepatogastroenterol. 37(1): 18-31 [1990]; A. B. Price and B. C. Morson, *Inflammatory bowel disease: the surgical pathology of Crohn's disease and ulcerative colitis*, Hum. Pathol. 6(1):7-29 [1975]). The practitioner is, of course not limited to these illustrative examples for diagnostic criteria, but should use criteria that are current in the art.

Detection of the presence of SIBO in the human subject also corroborates the suspected diagnosis of the SIBO-caused condition, held by a qualified medical practitioner who, prior to the detection of SIBO in the human subject, suspects from more limited clinical evidence that the human subject has, for example, irritable bowel syndrome, fibromyalgia, chronic fatigue syndrome, chronic pelvic pain syndrome, depression, autism, ADHD, an autoimmune disease, or Crohn's disease. By applying the inventive diagnostic method the suspected diagnosis is corroborated, i.e., confined, sustained, substantiated, supported, evidenced, strengthened, affirmed or made more firm.

The inventive method of treating SIBO, or a SIBO-caused condition, involves first detecting the presence or absence of SIBO in the subject by suitable detection means. Detecting the presence or absence of SIBO is accomplished by any suitable means or method known in the art. For example, one preferred method of detecting SIBO is breath hydrogen testing. (E.g., P. Kerlin and L. Wong, *Breath hydrogen testing in bacterial overgrowth of the small intestine*, Gastroenterol. 95(4):982-88 [1988]; A. Strocchi et al., *Detection of malabsorption of low doses of carbohydrate: accuracy of various breath $H_2$ criteria*, Gastroenterol. 105(5):1404-1410 [1993]; D. de Boissieu et al., [1996]; P. J. Lewindon et al., *Bowel dysfunction in cystic fibrosis: importance of breath testing*, J. Paedatr. Child Health. 34(1):79-82 [1998]). Breath hydrogen or breath methane tests are based on the fact that many obligately or facultatively fermentative bacteria found in the gastrointestinal tract produce detectable quantities of hydrogen or methane gas as fermentation products from a substrate consumed by the host, under certain circumstances. Substrates include sugars such as lactulose, xylose, lactose, sucrose, or glucose. The hydrogen or methane produced in the small intestine then enters the blood stream of the host and are gradually exhaled.

Typically, after an overnight fast, the patient swallows a controlled quantity, of a sugar, such as lactulose, xylose, lactose, or glucose, and breath samples are taken at frequent time intervals, typically every 10 to 15 minutes for a two- to four-hour period. Samples are analyzed by gas chromatography or by other suitable techniques, singly or in combination.

Plots of breath hydrogen in patients with SIBO typically show a double peak, i.e., a smaller early hydrogen peak followed by a larger hydrogen peak, but a single hydrogen peak is also a useful indicator of SIBO, if peak breath hydrogen exceeds the normal range of hydrogen for a particular testing protocol. (See, G. Mastropaolo and W. D. Rees, *Evaluation of the hydrogen breath test in man: definition and elimination of the early hydrogen peak*, Gut 28(6):721-25 [1987]).

A variable fraction of the population fails to exhale appreciable hydrogen gas during intestinal fermentation of lactulose; the intestinal microflora of these individuals instead produce more methane. (G. Corazza et al., *Prevalence and consistency of low breath $H_2$ excretion following lactulose ingestion. Possible implications for the clinical use of the $H_2$ breath test*, Dig. Dis. Sci. 38(11):2010-16 [1993]; S. M. Riordan et al., *The lactulose breath hydrogen test and small intestinal bacterial overgrowth*, Am. J. Gastroentrol. 91(9); 1795-1803 [1996]). Consequently, in the event of an initial negative result for breath hydrogen, or as a precaution, methane and/or carbon dioxide contents in each breath sample are optionally measured, as well as hydrogen, or a substrate other than lactulose is optionally used. Also, acting as a check, the presence of SIBO is demonstrated by a relative decrease in peak hydrogen exhalation values for an individual subject after antimicrobial treatment, in accordance with the present invention, compared to pretreatment values.

Another preferred method of detecting bacterial overgrowth is by gas chromatography with mass spectrometry and/or radiation detection to measure breath emissions of isotope-labeled carbon dioxide, methane, or hydrogen, after administering an isotope-labeled substrate that is metabolizable by gastrointestinal bacteria but poorly digestible by the human host, such as lactulose, xylose, mannitol, or urea. (E.g., G. R. Swart and J. W. van den Berg, $^{13}C$ *breath test in gastrointestinal practice*, Scand. J. Gastroenterol. [Suppl.] 225.13-18 [1998]; S. F. Dellert et al., *The 13C-xylose breath test for the diagnosis of small bowel bacterial overgrowth in children*, J. Pediatr. Gastroenterol. Nutr. 25(2): 153-58 [1997]; C. E. King and P. P. Toskes, *Breath tests in the diagnosis of small intestinal bacterial overgrowth*, Cit. Rev. Lab. Sci. 21(3):269-81 [1984]). A poorly digestible substrate is one for which there is a relative or absolute lack of capacity in a human for absorption thereof or for enzymatic degradation or catabolism thereof.

Suitable isotopic labels include $^{13}C$ or $^{14}C$. For measuring methane or carbon dioxide, suitable isotopic labels can also include $^{2}H$ and $^{3}H$ or $^{17}O$ and $^{18}O$, as long as the substrate is synthesized with the isotopic label placed in a metabolically suitable location in the structure of the substrate, i.e., a location where enzymatic biodegradation by intestinal microflora results in the isotopic label being sequestered in the gaseous product. If the isotopic label selected is a radioisotope, such as $^{14}C$, $^{3}H$, or $^{15}O$, breath samples can be analyzed by gas chromatography with suitable radiation detection means. (E.g., C. S. Chang et al., *Increased accuracy of the carbon-14 D-xylose breath test in detecting small-intestinal bacterial overgrowth by correction with the gastric emptying rate*, Eur. J. Nucl. Med. 22(10): 1118-22 [1995]; C. E. King and P. P. Toskes, *Comparison of the 1-gram [$^{14}C$]xylose, 10-gram lactulose-$H_2$, and 80-gram glucose-$H_2$ breath tests in patients with small intestine bacterial overgrowth*, Gastroenterol. 91(6):1447-51 [1986]; A. Schneider et al., *Value of the $^{14}C$-D-xylose breath test in patients with intestinal bacterial overgrowth*, Digestion 32(2):86-91 [1985]).

Another preferred method of detecting small intestinal bacterial overgrowth is direct intestinal sampling from the human subject. Direct sampling is done by intubation followed by scrape, biopsy, or aspiration of the contents of the intestinal lumen, including the lumen of the duodenum, jejunum, or ileum. The sampling is of any of the contents of the intestinal lumen including material of a cellular, fluids fecal, or gaseous nature, or sampling is of the lumenal wall itself. Analysis of the sample to detect bacterial overgrowth is by conventional microbiological techniques including microscopy, culturing, and/or cell numeration techniques.

Another preferred method of detecting small intestinal bacterial overgrowth is by endoscopic visual inspection of the wall of the duodenum, jejunum, and/or ileum.

The preceding are merely illustrative and non-exhaustive examples of methods for detecting small intestinal bacterial overgrowth.

Another suitable, and most preferred, means for detecting the presence or absence of SIBO is the present inventive method of detecting small intestinal bacterial overgrowth in a human subject, which involves detecting the relative amounts of methane, hydrogen, and at least one sulfur-containing gas in a gas mixture exhaled by said human subject, after the subject has ingested a controlled quantity of a substrate. The inventive method of detecting small intestinal bacterial overgrowth is more likely than conventional breath tests described above to detect the presence of SIBO, because in some subjects a pattern exists that is termed "non-hydrogen, non-methane: excretion" (see, e.g., Example 9c hereinbelow). This pattern is the result of the subject having a bacterial population constituting the SIBO condition, in which a sulfate-reducing metabolic pathway predominates as the primary means for the disposition of dihydrogen. In that condition, the removal of the hydrogen can be so complete that there is little residual hydrogen or methane gas to be detected in the exhaled breath, compared to the amount of sulfur-containing gas, such as hydrogen sulfide or a volatile sulfhydryl compound detectable by the inventive method of detecting small intestinal bacterial overgrowth.

In accordance with the inventive method, of detecting small intestinal bacterial overgrowth, the substrate is preferably a sugar; as described hereinabove, and more preferably a poorly digestible sugar or an isotope-labeled sugar. The at least one sulfur-containing gas is methanethiol, dimethylsulfide, dimethyl disulfide, an allyl methyl sulfide, an allyl methyl sulfide, an allyl methyl disulfide, an allyl disulfide, an allyl mercaptan, or a methylmercaptan. Most preferably, the sulfur-containing gas is hydrogen sulfide or a sulfhydryl compound.

The detection or determination of the relative amounts of methane, hydrogen, and at least one sulfur-containing gas in the exhaled gas mixture is accomplished by means or systems known in the art, preferably by means of gas chromatography (e.g., Brunette, D. M. et al., *The effects of dentrifrice systems on oral malodor*, J Clin Dent. 9:76-82 [1998]; Tangerman, A. et al., *A new sensitive assay for measuring volatile sulphur compounds in human breath by Tenax trapping and gas chromatography and its application in liver cirrhosis*, Clin Chim Acta 1983; May 9; 130(1):103-110 [1983]) and/or a radiation detection system, if appropriate. Most preferably, mass spectrometry is employed to detect the relative amounts of methane, hydrogen, and at least one sulfur-containing gas in the exhaled gas mixture. (E.g., Spanel P, Smith D., *Quantification of hydrogen sulphide in humid air by selected ion flow tube mass spectrometry*, Rapid Commun Mass Spectrom 14(13): 1136-1140 [2000]). Combined gas chromatography and mass spectrometry (GC/MS) is also useful. (E.g., Chinivasagam; H. N. et al., *Volatile components associated with bacterial spoilage of tropical prawns*, Int J Food Microbiol 1998 Jun. 30; 42(1-2):45-55). Most preferably, but not necessarily, the detection system employed requires only a single sample of exhaled gas mixture for the detection of methane, hydrogen, and at least one sulfur-containing gas. Detection methods that separately detect methane, hydrogen, and/or at least one sulfur containing gas are also useful.

Thus, thin-layer chromatography or high pressure liquid chromatography can be useful for detection of volatile sulfur-containing compounds. (E.g., Tsiagbe, V. K. et al., *Identification of volatile sulfur derivatives released from feathers of chicks fed diets with various levels of sulfur-containing amino acids*, J Nutr 1987 117(11): 18859-65 [1987]).

Direct-reading monitors for sulfides based on the use of an electrochemical voltammetric sensor or polarographic cell can also be employed. Typically, gas is drawn into a sensor equipped with an electrocatalytic sensing electrode. An electrical current is generated by an electrochemical reaction proportional to the concentration of the gas. The quantity of the gas is typically determined by comparing to a known standard.

In some embodiments of the inventive method of detecting SIBO in a human subject, before detection, volatile sulfur-containing gases are trapped in Tenax absorbent (e.g., Tangerman, A. et al., Clin Chim Acta May 9; 130(1):103-110 [1983]; Heida, H. et al., *Occupational exposure and indoor air quality monitoring in a composting facility*, Am Ind Hyg Assoc J 56(1):39-43 [1995]) or other solvent/absorbent system such as dinitrophenyl thioethers (Tsiagbe, V. K. et al. [1987]).

It generally takes about 2 to 3 hours of the subjects's time and a pre-test fast to accomplish breath testing for SIBO, thus, a quicker and more convenient screening method to determine those subjects most likely to have SIBO is desirable. Such a screening test allows the clinician to make a more informed decision as to which patients would likely benefit from more definitive. SIBO testing, as described above. This pre-screening reduces unnecessary inconvenience and expense for subjects who are unlikely to have SIBO.

Hence, the present invention provides a method of screening for the abnormally likely presence of SIBO in a human subject. By abnormally likely is meant a likelihood of SIBO greater than expected in the general population. The inventive-screening method involves obtaining a serum sample from the subject, which conventionally involves a blood draw, followed by separation of the serum from the whole blood. Conventional immunochemical techniques, such as ELISA, employing commercially available reagents, are used to quantitatively determine a concentration in the serum sample of serotonin (5-HT), one or more unconjugated bile acids (e.g., total bile acids or individual bile acids, e.g., deoxycholic acid), and/or folate, an abnormally elevated serum concentration of one or more of these being indicative of a higher than normal probability that SIBO is present in the subject. Such quantitative immunochemical determinations of serum values are also made commercially (e.g., Quest Diagnostics-Nichols Institute, 33608 Ortega Highway, San Juan Capistrano, Calif. 92690).

For example, a normal range for serum 5-HT is up to about 0.5 nanograms per milliliter. The normal range for total bile-acids in serum is about 4.0 to about 19.0 micromole per liter, and for deoxycholic acid the normal range is about 0.7 to about 7.7 micromoles per liter. Normal ranges for other unconjugated bile acids are also known. The normal range for serum folate is about 2.6 to about 20.0 nanograms per milliliter. In accordance with the inventive method, of screening; subjects with at least one serum value beyond the normal range are thus more than normally likely to have SIBO present and are candidates for further diagnostic SIBO detection procedures.

The present invention also relates to a method of determining the relative severity of SIBO or a SIBO-caused condition in a human subject in whom SIBO has been detected by a suitable detection means, as described herein above. If the presence of SIBO is detected in the subject, then suitable detection means are employed to detect in the subject a relative level of intestinal permeability, compared to normal. Abnormally high intestinal permeability indicates a relatively severe SIBO or SIBO-caused condition in the subject which alerts the clinician that a more aggressive SIBO treatment regimen is desirable.

Techniques for detecting intestinal permeability and normal intestinal permeability ranges are known. (E.g., Haase, A. M. et al., *Dual sugar permeability testing in diarrheal disease*, J. Pediatr. 136(2):232-37 [2000]; Spiller, R. C. et al., *Increased rectal mucosal endocrine cells, T lymphocytes, and increased gut permeability following acute Campylobacter enteritis and in post dysenteric irritable bowel syndrome*, Gut 47(6):804-11 [2000]; Smecuol, E. et al., *Sugar tests detect celiac disease among first-degree relatives*, Am J. Gastroenterol. 94(12):3547-52 [1999]; Cox; M. A. et al., *Measurement of small intestinal permeability markers, lactulose and mannitol in serum: results in celiac disease*, Dig. Dis. Sci. 44(2): 402-06 [1999]; Cox, M. A. et al., *Analytical method for the quantitation of mannitol and disaccharides in serum: a potentially useful technique in measuring small intestinal permeability in vivo*, Clin. Chim. Acta 263(2):197-205 [199.7]; Fleming, S. C. et al., *Measurement of sugar probes in serum: an alternative to urine measurement in intestinal permeability testing*, Clin. Chem. 42(3):445-48 [1996]).

Briefly, intestinal permeability is typically accomplished by measuring the relative serum or urine levels of two sugars, after ingestion of controlled amounts by the subject. One of the sugars, for example mannitol, is chosen because it is more typically more easily absorbed through the intestinal mucosa than the other sugar, for example, lactulose. Then about two hours after ingestion, a serum or urine sample is taken, and the ratio of the two sugars is determined. The closer the ratio of the two sugars in the sample approaches the ratio originally ingested, the more permeable is the subject's intestine.

After the presence of SIBO has been detected in the subject, in accordance with the inventive method of treating small intestinal bacterial overgrowth (SIBO) or a SIBO-caused condition in a human subject, the proliferating bacterial population constituting the SIBO is deprived of nutrient(s) sufficiently to inhibit the growth of the bacteria in the small intestine, which results in at least partially eradicating SIBO in the human subject.

Depriving the bacterial population of nutrient(s) is accomplished by any of a number of means.

For example, in some embodiments of the method of treating SIBO or a SIBO-caused condition, the subject consumes for a sustained period, a diet consisting essentially of nutrients that upon arrival in the upper gastrointestinal tract of the subject, are at least partially predigested. The sustained period being sufficient to at least partially eradicate SIBO in the human subject is at least about three days, preferably about 7 to about 18 days, and more preferably about 10 to about 14 days.

In some embodiments of the method, the at least partially predigested nutrient(s) are contained in a commestible total enteral nutrition (TEN) formulation, which is also called an "elemental diet." Such formulations are commercially available, for example, Vivonex® T.E.N. (SandozNutrition, Minneapolis, Minn.) and its variants, or the like. (See; e.g., Example 11 hereinbelow). A useful total enteral nutrition formulation satisfies all the subject's nutritional requirements, containing free amino acids, carbohydrates, lipids, and all essential vitamins and minerals, but in a form that is readily absorbable in the upper gastrointestinal tract, thus depriving or "starving" the bacterial population constituting the SIBO of nutrients of at least some of the nutrients they previously used for proliferating. Thus, bacterial growth in the small intestine is inhibited.

In another embodiment of the inventive method, a pancreatic enzyme supplement is administered to the subject before or substantially simultaneously with a meal, such that nutrients contained in the meal are at least partially predigested upon arrival in the upper gastrointestinal tract of the subject by the activity of the pancreatic enzyme supplement. Useful pancreatic enzyme supplements are commercially available, commonly called "Pancreatin"; such supplements contain amylase, lipase, and/or protease. Representative methods of administering the pancreatic enzyme supplement include giving, providing, feeding or force-feeding, dispensing, inserting, injecting, infusing, prescribing, furnishing, treating with, taking, swallowing, ingesting, eating or applying.

In a preferred embodiment, depending on the formulation, the pancreatic enzyme supplement is administered up to a period of 24 hours prior to ingestion of the food or nutrient comprising the meal, but most preferably between about 60 to 0 minutes before ingestion, which is substantially simultaneously with the meal. The period of time prior to ingestion is determined on the precise formulation of the composition. For example, a controlled release formulation can be administered, longer before the meal. Other quick release formulations can be taken substantially simultaneously with the meal.

In other embodiments of the method of treating small intestinal bacterial overgrowth or a SIBO-caused condition, depriving the bacterial population of nutrient(s) involves enhancing the digestion and/or absorption of the nutrient(s) in the upper gastrointestinal tract of the human subject by slowing transit of the nutrient(s) across the upper gastrointestinal tract of the human subject, thereby at least partially depriving the bacterial population of the nutrient(s). These embodiments of the inventive take advantage of a novel understanding of the peripheral neural connections that exist between the enteric nervous system of the upper gastrointestinal tract, including an intrinsic serotonergic neural pathway, and the vertebral ganglia, and thence to the central nervous system. The present invention provides a means to enhance region-to region (e.g., intestino-intestinal reflex) communications by way of replicating 5-HT as a signal (or releasing 5-HT at a distance as a surrogate signal). Thus, the present invention provides a way to increase 5-HT in locations in the central nervous by transmitting a neural signal from the gut, or to transmit a 5-HT-mediated neural signal originating in one location in the gut via an intrinsic cholinergic afferent neural pathway to a second distant location in the gut where a serotonergic signal of the same or greater intensity is replicated.

The present technology, therefore, allows neurally mediated modulation of the rate of upper gastrointestinal transit in the human subject. The present invention allows the artificially directed transmission and/or amplification of nervous signals from one location in the enteric nervous system to another via a prevertebral ganglion, bypassing the central nervous system. The invention takes advantage of an intrinsic serotonergic neural pathway involving an intrinsic cholinergic afferent neural pathway that projects from peptide YY-sensitive primary sensory neurons in the intestinal wall to the prevertebral celiac ganglion. The prevertebral celiac ganglion is in turn linked by multiple prevertebral ganglionic pathways to the central nervous system, to the superior mesenteric ganglion, to the inferior mesenteric ganglion, and also back to the enteric nervous system via an adrenergic efferent neural pathway that projects from the prevertebral celiac ganglion to one or more enterochromaffincells in the intestinal mucosa and to serotonergic interneurons that are, in turn, linked in the myenteric plexus or submucous plexus to opioid interneurons. The opioid interneurons are in turn linked to excitatory and inhibitory motoneurons. The opioid interneurons are also linked by an intestino-fugal opioid pathway that projects to the prevertebral celiac ganglion, with one or more neural connections therefrom to the central nervous system, including the spinal cord, brain, hypothalamus, and pituitary, and projecting back from the central nervous system to the enteric nervous system.

In particular, the present invention employs, a method of manipulating the rate of upper gastrointestinal transit of food or nutrient substance(s). The method involves administering by an oral or enteral delivery route a pharmaceutically acceptable composition comprising an active agent to the upper gastrointestinal tract. To slow the rate of upper gastrointestinal transit, the active agent is an active lipid; a serotonin, serotonin agonist, or serotonin re-uptake inhibitor; peptide YY or a peptide YY functional analog; calcitonin gene-related peptide (CGRP) or a CGRP functional analog; an adrenergic agonist; an opioid agonist; or a combination of any of any of these, which is delivered in an amount and under conditions such that the cholinergic intestino-fugal pathway, at least one prevertebral ganglionic pathway, the adrenergic efferent neural pathway, the serotonergic interneuron and/or the opioid interneuron are activated thereby. This results in the rate of upper gastrointestinal transit in the subject being slowed, which is the basis for prolonging the residence time of orally or enterally administered food or nutrient substances, thus promoting or enhancing their dissolution and/or absorption in the upper gastrointestinal tract.

The inventive pharmaceutically acceptable compositions limit the presentation of a food or nutrient substance to the proximal region of the small intestine for absorption.

Depending on the desired results, useful active agents include, active-lipids; serotonin, serotonin agonists, or serotonin re-uptake inhibitors; peptide YY or peptide YY functional analogs; CGRP or CGRP functional analogs; adrenergic agonists; opioid agonists; or a combination of any of any of these; antagonists of serotonin receptors, peptide YY receptors, adrenoceptors, opioid receptors, CGRP receptors, or a combination of any of these. Also useful are antagonists of serotonin receptors, peptide YY receptors, CGRP receptors; adrenoceptors and/or opioid receptors.

Serotonin, or 5-hydroxytryptamine (5-HT) is preferably used at a dose of about 0.03 to about 0.1 mg/kg of body mass. 5-HT3 and 5-HT4 serotonin receptor agonists are known and include HTF-919 and R-093877 (Foxx-Orenstein, A. E. et al., Am. J. Physiol. 275(5 Pt 1):G979-83 [1998]); prucalopride; 2-[1-(4-Piperonyl)piperazinyl]benzothiazole; 1-(4-Amino-5-chloro-2-methoxyphenyl)-3-[1-butyl-4-piperidinyl]-1-propanone; and 1-(4-Amino-5-chloro-2-methoxyphenyl)-3-[1-2-methylsulphonylamino)ethyl-4-piperidinyl]-1-propanone. Serotonin re-uptake inhibitors include Prozac or Zoloft.

Useful serotonin receptor antagonists include known antagonists of 5-HT3, 5-HT1P, 5-HT1A, 5-HT2, and/or 5-HT4 receptors. Examples include ondansetron or granisetron, 5HT3 receptor antagonists (preferred dose range of about 0.04 to 5 mg/kg), deramciclane (Varga, G et al., *Effect of deramciclane, a new 5-HT receptor antagonist, on cholecystokinin-induced changes in rat gastroiniestinal function*, Eur. J. Pharmacol. 367(2-3):315-23 [1999]), or alosetron. 5-HT4 receptor antagonists are preferably used at a dose of about 0.05 to 500 picomoles/kg. 5-HT4 receptor antagonists include 1-Piperidinylethyl 1H-indole-3-carboxylate (SB203186); 1-[4-Amino-5-chloro-2-(3,5-dimethoxyphenyl)methyloxy]-3-[1-[2-methylsulphonylamino]ethyl]piperidin-4-yl]propan-1-one (RS 39604); 3-(Piperidin-1-yl)propyl 4-amino-5-chloro-2-methoxybenzoate.

Peptide YY (PYY) and its functional analogs are preferably delivered at a dose of about 0.5 to about 500 picomoles/kg. PYY functional analogs include PYY (22-36), BIM-43004 (Liu, C D. et al., J. Surg. Res. 59(1):80-84 [1995]), BIM-43073D, BIM-43004C (Litvak, D. A. et al., Dig. Dig. Sci. 44(3):643-48 [1999]). Other examples are also known in the art (e.g., Balasubramaniam, U.S. Pat. No. 5,604, 203).

PYY receptor antagonists preferably include antagonists of Y4/PP1, Y5 or Y5/PP2/Y2, and most preferably Y1 or Y2. (E.g., Croom et al., U.S. Pat. No. 5,912,227) Other examples include BIBP3226, CGP71683A (King, P. J. et al., J. Neurochem. 73(2):641-46 [1999]).

CGRP receptor antagonists include human CGRP(8-37) (e.g., Foxx-Orenstein et al., Gastroenterol. 1 (5):1281-90 [1996]).

Useful adrenergic agonists include norepinephrine.

Adrenergic or adrenoceptor antagonists include β-adrenoceptor antagonists, including propranolol and atenolol. They are preferably used at a dose of 0:05-2 mg/kg.

Opioid agonists include delta-acting opioid agonists (preferred dose range is 0.05-50 mg/kg, most preferred is 0.05-25 mg/kg); kappa-acting opioid agonists (preferred dose range is 0.005-100 microgram/kg); mu-acting opioid agonists (preferred dose range is 0.05-25 microgram/kg); and epsilon-acting agonists. Examples of useful opioid agonists include deltorphins (e.g., deltorphin II and analogues), enkephalins (e.g., [d-Ala(2), Gly-ol(5)]-enkephalin [DAMGO]; [D-Pen (2,5)]-enkephalin [DPDPE]), dinorphins, trans-3,4-dichloro-N-methyl-N-[2-(1-pyrrolidinyl)cyclohexyl-]benzeneacetamide methane sulfonate (U-50, 488H), morphine, codeine, endorphin, or β-endorphin.

Opioid receptor antagonists include mu-acting opioid antagonists (preferably used at a dose range of 0.05-5 microgram/kg); kappa opioid receptor antagonists (preferably used at a dose of 0.05-30 mg/kg); delta opioid receptor antagonists (preferably used at a dose of 0.05-200 microgram/kg); and epsilon opioid receptor antagonists. Examples of useful opioid receptor antagonists include naloxone, naltrexone, methylnaltrexone, nalmefene, H2186, H3116, or fedotozine, i.e., (+)-1-1[3,4,5-trimethoxy)benzyloxymethyl]-1-phenyl-N,N=dimethylpropylamine. Other useful opioid receptor antagonists are known (e.g., Kreek et al., U.S. Pat. No. 4,987, 136).

The active agents listed above are not exhaustive but rather illustrative examples, and one skilled in the art is aware of other useful examples.

As used herein, "active lipid" encompasses a digested or substantially digested molecule having a structure and function substantially similar to a hydrolyzed end-product of fat digestion. Examples of hydrolyzed end products are molecules such as diglyceride, monoglyceride, glycerol, and most preferably free fatty acids or salts thereof.

In a preferred embodiment, the active agent is an active lipid comprising a saturated or unsaturated fatty acid. Fatty acids contemplated by the invention include fatty acids having between 4 and 24 carbon atoms (C4-C24).

Examples of fatty acids contemplated for use in the practice of the present invention include caprolic acid, caprulic acid, capric acid, lauric acid, myristic acid, oleic acid, palmitic acid, stearic acid, palmitoleic acid, linoleic acid, linolenic acid, trans-hexadecanoic acid, elaidic acid, columbinic acid, arachidic acid, behenic acid eicosenoic acid, erucic acid, bressidic acid, cetoleic acid, nervonic acid, Mead acid, arachidonic acid, timnodonic acid, clupanodonic acid, docosahexaenoic acid, and the like. In a preferred embodiment, the active lipid comprises oleic acid.

Also preferred are active lipids in the form of pharmaceutically acceptable salts of hydrolyzed fats, including salts of fatty acids. Sodium or potassium salts are preferred, but salts formed with other pharmaceutically acceptable cations are also useful. Useful examples include sodium- or potassium salts of caprolate, caprulate, caprate, laurate, myristate, oleate, palmitate, stearate, palmitolate, linolate, linolenate, trans-hexadecanoate, elaidate, columbinate, arachidate, behenate, eicosenoate, erucate, bressidat, cetoleate, nervoniate, arachidonate, timnodonate, clupanodonate, docosahexaenoate, and the like. In a preferred embodiment, the active lipid comprises an oleate salt.

The active agents suitable for use with this invention are employed in well dispersed form in a pharmaceutically acceptable carrier. As used herein, "pharmaceutically acceptable carrier" encompasses any of the standard pharmaceutical carriers known to those of skill in the art. For example, one useful carrier is a commercially available emulsion, Ensure®, but active lipids, such as oleate or oleic acid are also dispersible in gravies, dressings, sauces or other comestible carriers. Dispersion can be accomplished in various ways. The first is that of a solution.

Lipids can be held in solution if the solution has the properties of bile (i.e., solution of mixed micelles with bile salt added), or the solution has the properties of a detergent (e.g., pH 9.6 carbonate buffer) or a solvent (e.g., solution of Tween). The second is an emulsion which is a 2-phase system in which one liquid is dispersed in the form of small globules throughout another liquid that is immiscible with the first liquid (Swinyard and Lowenthal, "Pharmaceutical Necessities" *REMINGTON'S PHARMACEUTICAL SCIENCES,* 17th ed., AR Gennaro (Ed), Philadelphia College of Pharmacy and Science, 1985 p. 1296). The third is a suspension with dispersed solids (e.g., microcrystalline suspension). Additionally, any emulsifying and suspending agent that is acceptable for human consumption can be used as a vehicle for dispersion of the composition. For example, gum acacia, agar, sodium alginate, bentonite, carbomer, carboxymethylcellulose, carrageenan, powdered cellulose, cholesterol, gelatin, hydroxyethyl cellulose, hydroxypropyl cellulose, hydroxypropyl methylcellulose, methylcellulose, octoxynol 9, oleyl alcohol, polyvinyl alcohol, povidone, propylene glycol monostearate, sodium lauryl sulfate, sorbitan esters, stearyl alcohol, tragacanth, xantham gum, chondrus, glycerin, trolamine, coconut oil, propylene glycol, thyl alcohol malt, and malt extract.

Any of these formulations, whether it is a solution, emulsion or suspension containing the active agent, can be incorporated into capsules, or a microsphere or particle, (coated or not) contained in a capsule.

The pharmaceutically acceptable compositions containing the active agent, in accordance with the invention, is in a form suitable for oral or enteral use, for example, as tablets, troches, lozenges, aqueous or oily suspensions, dispersible powders or granules, emulsions, hard or soft capsules, syrups, elixirs or enteral formulas. Compositions intended for oral use are prepared according to any method known to the art for the manufacture of pharmaceutical compositions. Compositions can also be coated by the techniques described in the U.S. Pat. Nos. 4,256,108; 4,160,452; and 4,265,874, to form osmotic therapeutic tablets for controlled release. Other techniques for controlled release compositions, such as those described in the U.S. Pat. Nos. 4,193,985; and 4,690,822; 4,572,833 can be used in the formulation of the inventive pharmaceutically acceptable compositions.

An effective amount of active lipid is any amount that is effective to slow gastrointestinal transit and control presentation of a food or nutrient substance to a desired region of the small intestine. For example, an effective amount of active lipid, as contemplated by the instant invention, is any amount of active lipid that can trigger any or all of the following reflexes: intestino-lower esophageal sphincter (relaxation of LES); intestino-gastric feedback (inhibition of gastric emptying); intestino-intestinal feedback (ileo-jejunal feedback/ileal brake, jejuno-jejunal feedback/jejunal brake, intestino-CNS feedback (for example, intensifying intestinal signalling of satiety); intestino-pancreatic feedback (control of exocrine enzyme output); intestino-biliary feedback (control of bile flow); intestino-mesenteric blood flow feedback (for the control of mucosal hyperemia); intestino-colonic feedback (so called gastro-colonic reflex whereby the colon contracts in response to nutrients in the proximal small intestine):

Methods of administering are well known to those of skill in the art and include most preferably oral administration and/or enteral administration. Representative methods of administering include giving, providing, feeding or force-feeding, dispensing, inserting, injecting infusing, perfusing, prescribing, furnishing, treating with, taking, swallowing, eating or applying. Preferably the pharmaceutically acceptable composition comprising the active agent is administered in the setting of a meal, i.e., along with or substantially simultaneously with the meal, most preferably an hour or less before the meal. It is also useful to administer the active agent in the fasted state, particularly if the pharmaceutical composition containing the active agent is formulated for long acting or extended release. In some embodiments, such as the inventive method for manipulating post-prandial blood flow, the pharmaceutical composition is also usefully administered up to an hour after a meal, and most preferably within one hour before or after the meal.

In order to stretch biologic activity so that one has a convenient, daily dosage regimen, the present invention contemplates that the inventive compositions can be administered prior to ingestion of the food, nutrient and/or drug.

In a preferred embodiment, the inventive compositions (depending on the formulation) are administered up to a period of 24 hours prior to ingestion of the food, nutrient and/or drug, but most preferably between about 60 to 5 minutes before ingestion. The period of time prior to ingestion is determined on the precise formulation of the composition. For example, if the formulation incorporates a controlled release system, the duration of release and activation of the active lipid will determine the time for administration of the composition. Sustained release formulation of the composition is useful to ensure that the feedback effect is sustained.

In a preferred embodiment, the pharmaceutically acceptable composition of the invention contains an active lipid and is administered in a load-dependent manner which ensures that the dispersion of active lipid is presented to the entire length of the small intestine. Administration is in one or more doses such that the desired effect is produced. In some preferred embodiments, the load of active lipid per dose is from about 0.5 grams to about 2.0 grams, but can range up to about 25 grams per dose as needed. Generally, patients respond well to the most preferred amount of active lipid, which is in the range of about 1.6 to 3.2 grams. For patients who fail to respond to this dose range, a dose between 6 and 8 grams is typically effective.

Sequential dosing is especially useful for patients with short bowel syndrome or others with abnormally rapid intestinal transit times. In these patients, the first preprandial administration of the active lipid occurs in a condition of uncontrolled intestinal transit that can fail to permit optimal effectiveness of the active lipid. A second (or more) preprandial administration(s) timed about fifteen minutes after the first or previous administration and about fifteen minutes before the meal enhances the patient's control of intestinal lumenal contents and the effectiveness of the active lipid in accordance with the inventive methods. Normalization of nutrient absorption and bowel control throughout the day, including during the patient's extended sleeping hours, is best achieved by a dietary regimen of three major meals with about five snacks interspersed between them, including importantly, a pre-bedtime snack; administration of a dose of the inventive composition should occur before each meal or shack as described above.

Treatment with the inventive compositions in accordance with the inventive methods can be of singular occurrence or can be continued indefinitely as needed. For example, patients deprived of food for an extended period (e.g., due to a surgical intervention or prolonged starvation), upon the reintroduction of ingestible food, can benefit from administration of the inventive compositions before meals on a temporary basis to facilitate a nutrient adaptive response to normal feeding. On the other hand some patients, for example those with surgically altered intestinal tracts (e.g., ileal resection), can benefit from continued pre-prandial treatment in accordance with the inventive methods for an indefinite period. However, clinical experience with such patients for over six years has demonstrated that after prolonged treatment there is at least a potential for an adaptive sensory feedback response that can allow them to discontinue treatment for a number of days without a recurrence of postprandial diarrhea or intestinal dumping.

The use of pharmaceutically acceptable compositions of the present invention in enteral feeding contemplates adding the composition directly to the feeding formula. The composition can either be compounded as needed into the enteral formula when the rate of formula delivery is known (i.e., add just enough composition to deliver the load of active lipids). Alternatively, the composition of the invention can be compounded at the factory so that the enteral formulas are produced having different concentrations of the composition and can be used according to the rate of formula delivery (i.e., higher concentration of composition for lower rate of delivery).

If the inventive composition were to be added to an enteral formula and the formula is continuously delivered into the small intestine, the composition that is initially presented with the nutrient formula allows slowing the transit of nutrients that are delivered later. Except for the start of feeding when transit can be too rapid because the inhibitory feedback from the composition has yet to be fully activated, once equilibrium is established, it is no longer logistically an issue of delivering the composition as a premeal although the physiologic principle is still the same.

Before dietary fats can be absorbed, the motor activities of the small intestine in the postprandial period must first move the output from the stomach to the appropriate absorptive sites of the small intestine. To achieve the goal of optimizing the movement of a substance, through the small intestine, the temporal and spatial patterns of intestinal motility are specifically controlled by the nutrients of the lumenal content:

Without wishing to be bound by any theory, it is presently believed that early in gastic emptying, before inhibitory feedback is activated, the load of fat entering the small intestine can be variable and dependent on the load of fat in the meal. Thus, while exposure to fat can be limited to the proximal small bowel after a small load, a larger load, by overwhelming more proximal absorptive sites, can spill further along the small bowel to expose the distal small bowel to fat. Thus, the response of the duodenum to fat limits the spread of fat so that more absorption can be completed in the proximal small intestine and less in the distal small intestine. Furthermore, since the speed of movement of lumenal fat must decrease when more fat enters the duodenum, in order to avoid steatorrhea, intestinal transit is inhibited in a load-dependent fashion by fat. This precise regulation of intestinal transit occurs whether the region of exposure to fat is confined to the proximal gut or extended to the distal gut.

In accordance with the present invention it has been observed that inhibition of intestinal transit by fat depends on the load of fat entering the small intestine. More specifically, that intestinal transit is inhibited by fat in a load-dependent fashion whether the nutrient is confined to the proximal segment of the small bowel or allowed access to the whole gut.

As described above, the inventive technology can also operate by transmitting to and replicating at a second location in the upper gastrointestinal tract a serotonergic neural signal originating at a first location in the proximal or distal gut of a mammal. For example, the first location can be in the proximal gut and the second location can be elsewhere in the proximal gut or in the distal gut. Or conversely, the first location can be in the distal gut and the second location can be elsewhere in the distal gut or in the proximal gut.

Employing this inventive technology to slow the rate of upper gastrointestinal transit, during and after a meal, nutrient absorption in the upper gastrointestinal tract is enhanced, depriving bacterial populations in the lower small intestine of nutrients. In response to luminal fat in the proximal or distal gut, a serotonin (5-HT)-mediated anti-peristaltic slowing response is normally present. Therefore, some embodiments of the method involve increasing 5-HT in the gut wall by administering to the mammal and delivering to the proximal and/or distal gut, an active lipid, or serotonin, a serotonin agonist, or a serotonin re-uptake inhibitor.

Alternatively, the active agent is PYY, or a PYY functional analog. PYY or the PYY analog, activates the PYY-sensitive primary sensory neurons in response to fat or 5-HT. Since the predominant neurotransmitter of the PYY-sensitive primary sensory neurons is calcitonin gene-related peptide (CGRP), in another embodiment, CGRP or a CGRP functional analog is the active agent.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) agonist to activate neural signal transmission to the efferent limb of the anti-peristaltic reflex response to luminal fat.

Since adrenergic efferent neural pathway(s) from the prevertebral ganglia to the enteric nervous system stimulate serotonergic interneurons, which in turn stimulate enteric opioid interneurons, in other embodiments of the method, the active agent is 5-HT, 5-HT receptor agonist, or a 5-HT re-uptake inhibitor to activate or enhance neural signal transmission at the level of the serotoneregic interneurons.

Alternatively, the active agent is an opioid receptor agonist to activate or enhance neural signal transmission via the opioid interneurons.

In accordance with the invention, pharmaceutically acceptable compositions containing the active agent can be in a form suitable for oral use, for example, as tablets, troches, lozenges, aqueous or oily suspensions, dispersible powders or granules, emulsions, hard or soft capsules, syrups, elixirs or enteral formulas. Compositions intended for oral use can be prepared according to any method known to the art for the manufacture of pharmaceutical compositions and such compositions can contain one or more other agents selected from the group consisting of a sweetening agent such as sucrose, lactose, or saccharin, flavoring agents, such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients can also be manufactured by known methods. The excipients used can be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the techniques described in the U.S. Pat. Nos. 4,256,108; 4,160,452; and 4,265,874, to form osmotic therapeutic tablets for controlled release. Other techniques for controlled release compositions; such as those described in the U.S. Pat. Nos. 4,193,985; and 4,690,822; 4,572,833 can be used in the formulation of the inventive pharmaceutically acceptable compositions.

In some cases, formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, for example, peanut oil, liquid paraffin, or olive oil.

In one embodiment of the present invention, the pharmaceutically acceptable composition is an enterically coated or a sustained release form that permits intestinal transit to be slowed for a prolonged period of time.

In an alternative aspect of the method of treating small intestinal bacterial overgrowth (SIBO) or a SIBO-caused condition in a human subject; after the presence of SIBO is detected in the human subject by suitable detection means, as described above, a pharmaceutically acceptable disinfectant composition is introduced into the lumen of the small intestine so as to contact the bacteria constituting the SIBO condition. The disinfectant composition is introduced in an amount sufficient to inhibit the growth of the bacteria in the small intestine, thereby at least partially eradicating SIBO in the human subject.

Preferably, the pharmaceutically acceptable disinfectant composition consists essentially of hydrogen peroxide; a bismuth-containing compound or salt; or an iodine-containing compound or salt. The pharmaceutically acceptable disinfectant (i.e., bacteriocidal) composition can also contain other non-bacteriocidal ingredients, such as any suitable pharmaceutically acceptable carrier, excipient, emulsant, solvent, colorant, flavorant, and/or buffer, as described hereinabove. Formulations for oral or enteral delivery are useful, as described hereinabove with respect to known delivery modalities for active agents, e.g., tablets, troches, lozenges, aqueous or oily suspensions, dispersible powders or granules, emulsions, hard or soft capsules, syrups, elixirs or enteral formulas.

Embodiments of disinfectant or bacteriocidal compositions containing hydrogen peroxide are known for internal use in vertebrates (e.g., Ultradyne, Ultra Bio-Logics Inc., Montreal, Canada). Preferably, an aqueous solution of about 1% to about 3% (v/v) hydrogen peroxide is introduced orally or otherwise enterally to the lumen, most conveniently by ingestion.

Embodiments of disinfectant or bacteriocidal compositions containing bismuth compounds or salts are also known, for example, bismuth-2-3-dimercaptopropanol (BisBAL), bismuth thiols (e.g., bismuth-ethanedithiol); or bismuth-3,4-dimercaptotoluene (BisTOL), and in over the counter preparations, such as PeptoBizmol. (See, e.g., Domenico, P. et al., Activity of Bismuth Thiols against Staphylococci and Staphylococcal biofilms, Antimicrob. Agents Chemother. 45(5): 1417-21 [2001]).

Embodiments of disinfectant or bacteriocidal compositions containing iodine compounds or salts are also known, for example, povidone-iodine solutions.

In still another alternative aspect of the method of treating small intestinal bacterial overgrowth (SIBO) or a SIBO-caused condition in a human subject, after the presence of SIBO is detected in the human subject by suitable detection means, as described above, a pharmaceutically acceptable composition is administered to the subject. The pharmaceutically acceptable composition contains a stabilizer of mast cell membranes in the lumenal wall of the small intestine, in an amount sufficient to inhibit a mast cell-mediated immune response in the human subject. This embodiment is a relatively aggressive treatment and is most useful in more severe or advanced SIBO, for example, as confirmed by high intestinal permeability in the subject (see hereinabove); Suitable mast cell stabilizers include oxatamide or Chromoglycate (potassium or sodium salts preferred). (e.g., Pacor, M. L. et al., *Controlled study of oxatomide vs disodium chromoglycate for treating adverse reactions to food*, Drugs Exp Clin Res 18(3):119-23 [1992]; Stefanini, G. F. et al., *Oral cromolyn sodium in comparison with elimination diet in the irritable bowel syndrome, diarrheic type*, Multicenter Study of 428 patients, Scand. J. Gastroenterol. 30(6):535-41 [1995]; Andre, F. et al., *Digestive permeability to different-sized molecules and to sodium cromoglycate in food allergy*, Allergy Proc. 12(5); 293-98 [1991]; Lunardi, C. et al., *Double-blind cross-over trial of oral sodium cromoglycate in patients with irritable bowel syndrome due to food intolerance*, Clin Exp Allergy 21(5):569-72. [1991]; Burks, A. W. et al., *Double-blind placebo-controlled trial of oral cromolyn in children with atopic dermatitis and documented food hypersensitivity*, J. Allergy Clin. Immunol. 81(2):417-23 [1988]).

After the SIBO condition is at least partially eradicated, typically within a couple of weeks, there is an improvement in the symptom(s) of irritable bowel syndrome, fibromyalgia, chronic fatigue syndrome, chronic pelvic pain syndrome, autism, impaired mentation, impaired memory, depression, ADHD, an autoimmune disease, or Crohn's disease. It is a benefit of the inventive treatment method that after treatment, subjects routinely report feeling better than they have felt in years.

The inventive method of treating small intestinal bacterial overgrowth (SIBO) or a SIBO-caused condition in a human subject, as described above, can be optionally combined, simultaneously or in sequence, with other suitable methods of it least partially eradicating small intestinal bacterial overgrowth, such as the following.

For example, at least partially eradicating the bacterial overgrowth is accomplished by administering an antimicrobial agent, including but not limited to a natural, synthetic; or semi-synthetic antibiotic agent. For example, a course of antibiotics such as, but not limited to, neomnycin, metronidazole, teicoplanin, doxycycline, tetracycline, ciprofloxacin, augmentin, cephalexin (e.g., Keflex), penicillin, ampicillin, kanamycin, rifamycin, rifaximin, or vancomycin, which may be administered orally, intravenously, or rectally. (R. K. Cleary [1998]; C. P. Kelly and J. T. LaMont, *Clostridium difcile infection*, Annu. Rev. Med. 49:375-90 [1998]; C. M. Reinke and C. R. Messick, *Update on Clostridium difficile-induced colitis*, Part 2, Am. J. Hosp. Pharm. 51(15):1892-1901 [1994]).

Alternatively, an antimicrobial chemotherapeutic agent, such as a 4- or 5-aminosalicylate compound is used to at least partially eradicate the SIBO condition. These can be formulated for ingestive, colonic, or topical non-systemic delivery systems or for any systemic-delivery systems. Commercially available preparations include 4-(p)-aminosalicylic acid (i.e., 4-ASA or para-aminosalicylic acid) or 4-(p)-aminosalicylate sodium salt (e.g., Nemasol-Sodium® or Tubasal®). 5-Aminosalicylates have antimicrobial, as well as anti-inflammatory properties (H. Lin and M. Pimentel, Abstract G3452 at Digestive Disease Week, 100$^{th}$ Annual Meeting of the AGA, Orlando, Fla. [1999]), in useful preparations including 5-aminosalicylic acid (i.e., 5-ASA, mesalamine, or mesalazine) and conjugated derivatives thereof, available in various pharmaceutical preparations such as Asacol®, Rowasa®, Clayersal®, Pentasa®, Salofalk®, Dipentum® (olsalazine), Azulfidine® (SAZ; sulphasalazine), ipsalazine, salicylazobenzoic acid, balsalazide, or conjugated bile acids, such as ursodeoxycholic acid-5-aminosalicylic acid, and others.

Another preferred method of at least partially eradicating: small intestinal bacterial: overgrowth, particularly useful when a subject does not respond well to oral or intravenous antibiotics or other antimicrobial agents alone, is administering an intestinal lavage or enema, for example, small bowel irrigation with a balanced hypertonic electrolyte solution, such as Go-lytely or fleet phosphosoda preparations. The lavage or enema solution is optionally combined with one or more antibiotic(s) or other antimicrobial agent(s). (E.g., J. A. Vanderhoof et al., *Treatment strategies for small bowel bacterial overgrowth in short bowel syndrome*, J. Pediatr. Gastroenterol. Nutr. 27(2):155-60 [1998])

Another preferred method of at least partially eradicating small intestinal bacterial overgrowth employs a probiotic agent, for example, an inoculum of a lactic acid bacterium or bifidobacterium. (A. S. Naidu et al., *Probiotic spectra of lactic acid bacteria*, Crit. Rev. Food Sci. Nutr. 39(1):13-126 [1999]; J. A. Vanderhoof et al. [1998]; G. W. Tannock, *Probiotic properties of lactic acid bacteria: plenty of scope for R & D*, Trends Biotechnol. 15(7):270-74 [1997]; S. Salminen et al., *Clinical uses of probiotics for stabilizing the gut mucosal barrier: successful strains and future challenges*, Antonie Van Leeuwenhoek 70(2-4):347-58 [1997]). The inoculum is delivered in a pharmaceutically acceptable ingestible formulation, such as in a capsule, or for some subjects, consuming a food supplemented with the inoculum is effective, for example a milk, yoghurt, cheese, meat or other fermentable food preparation. Useful probiotic agents include *Bifidobacterium* sp. or *Lactobacillus* species or strains, e.g., *L. acidophilus, L rhamnosus, L. plantarum, L. reuteri, L. paracasei* subsp. *paracasei*, or *L. casei* Shirota, (P. Kontula et al., *The effect of lactose derivatives on intestinal lactic acid bacteria*, J. Dairy Sci. 82(2):249-56 [1999]; M. Alander et al., *The effect of probiotic strains on the microbiota of the Simulator of the*

*Human Intestinal Microbial Ecosystem (SHIME)*, Int. J. Food Microbiol. 46(1):71-79 [1999]; S. Spanhaak et al., *The effect of consumption of milk fermented by Lactobacillus casei strain Shirota on the intestinal microflora and immune parameters in humans*, Eur. J. Clin. Nutr. 52(12):899-907 [1998]; W. P. Charteris et al., *Antibiotic susceptibility of potentially probiotic Lactobacillus species*, J. Food Prot. 61(12):1636-43 [1998]; B. W. Wolf et al., Safety and tolerance of *Lactobacillus reuteri* supplementation to a population infected with, the human immunodeficiency virus, Food Chem. Toxicol. 36(12): 1085-94 [1998]; G. Gardiner et al., *Development of a probiotic cheddar cheese containing human-derived Lactobacillus paracasei strains*, Appl. Environ. Microbiol. 64(6):2192-99 [1998]; T. Sameshima et al., *Effect of intestinal Lactobacillus starter cultures on the behaviour of Staphylococcus aureus in fermented sausage*, Int. J. Food Microbiol. 41(1):1-7 [1998]).

Optionally, after at least partial eradication of small intestinal bacterial overgrowth, use of antimicrobial agents or probiotic agents can be continued to prevent further development or relapse of SIBO.

Another preferred method of at least partially eradicating small intestinal bacterial overgrowth is by normalizing or increasing phase III interdigestive intestinal motility between meals with any of several modalities to at least partially eradicate the bacterial overgrowth, for example, by suitably modifying the subject's diet to increase small intestinal motility to a normal level (e.g., by increasing dietary fiber), or by administration of a chemical prokinetic agent to the subject, including bile acid replacement therapy when this is indicated by low or otherwise deficient bile acid production in the subject:

For purposes of the present invention, a prokinetic agent is any chemical that causes an increase in phase III interdigestive motility of a human subjects intestinal tract. Increasing, intestinal motility, for example, by administration of a chemical prokinetic agent, prevents relapse of the SIBO condition, which otherwise typically recurs within about two months, due to continuing intestinal dysmotility. The prokinetic agent causes an in increase in phase III interdigestive motility of the human subject's intestinal tract, thus preventing a recurrence of the bacterial overgrowth. Continued administration of a prokinetic agent to enhance a subject's phase II interdigestive motility can extend for an indefinite period as needed to prevent relapse of the SIBO condition.

Preferably, the prokinetic agent is a known prokinetic peptide, such as motilin, or functional analog thereof such as a macrolide compound, for example, erythromycin (50 mg/day to 2000 mg/day in divided doses orally or I.V. in divided doses), or azithromycin (250-1000 mg/day orally).

However, a bile acid, or a bile salt derived therefrom, is another preferred prokinetic agent for inducing or increasing phase III interdigestive motility. (E. P. DiMagno, *Regulation of interdigestive gastrointestinal motility and secretion*, Digestion 58 Suppl. 1:53-55 [1997]; V. B. Nieuwenhuijs et al., *Disrupted bile flow affects interdigestive small bowel motility in rats*, Surgery 122(3):600-08 [1997]; P. M. Hellstrom et al., *Role of bile in regulation of gut motility*, J. Intern. Med. 237(4):395-402 [1995]; V. Plourde et al., *Interdigestive intestinal motility in dogs with chronic exclusion of bile from the digestive tract*, Can. J. Physiol. Pharmacol. 65(12):2493-96 [1987]). Useful bile acids include ursodeoxycholic acid and chenodeoxycholic acid; useful bile salts include sodium or potassium salts of ursodeoxycholate or chenodeoxycholate, or derivatives thereof.

A compound with cholinergic activity, such as cisapride. (i.e., Propulsid®; 1 to 20 mg, one to four times per day orally or I.V.), is also preferred as a prokinetic agent for inducing or increasing phase III interdigestive motility. Cisapride is particularly effective in alleviating or improving hyperalgesia related to SIBO or associated with disorders caused by SIBO, such as IBS, fibromyalgia, or Crohn's disease.

A dopamine antagonist, such as metoclopramide (1-10 mg four to six times per day orally or I.V.), domperidone (10 mg, one to four times per day orally), or bethanechol (5 mg/day to 50 mg every 3-4 hours orally; 5-10 mg four times daily subcutaneously), is another preferred prokinetic agent for inducing or increasing phase III interdigestive motility. Dopamine antagonists, such as domperidone, are particularly effective in alleviating or improving hyperalgesia related to SIBO or associated with disorders caused by SIBO, such as IBS, fibromyalgia, or Crohn's disease.

Also preferred is a nitric oxide altering agent, such as nitroglycerin, nomega-nitro-L-arginine methylester (L-NAME), N-monomethyl-L-arginine (L-NMMA), or a 5-hydroxytryptamine (HT or serotonin) receptor antagonist, such as ondansetron (2-4 mg up to every 4-8 hours I.V.; pediatric 0.1 mg/kg/day) or alosetron. The 5-HT receptor antagonists, such as ondansetron and alosetron, are particularly effective in improving hyperalgesia related to SIBO, or associated with disorders caused by SIBO, such as IBS, fibromyalgia, or Crohn's disease.

An antihistamine, such as promethazine (oral or I.V. 12.5 mg/day to 25 mg every four hours orally or I.V.), meclizine (oral 50 mg/day to 100 mg four times per day), or other antihistamines, except ranitidine (Zantac), famotidine, and nizatidine, are also preferred as prokinetic agents for inducing or increasing phase III interdigestive motility.

Also preferred are neuroleptic agents, including prochlorperazine (2.5 mg/day to 10 mg every three hours orally, 25 mg twice daily rectally; 5 mg/day to 10 mg every three hours, not to exceed 240 mg/day intramuscularly; 2.5 mg/day to 10 mg every four hours I.V.), chlorpromazine (0.25 mg/lb. up to every four hours [5-400 mg/day] orally; 0.5 mg/lb. up to every 6 hours rectally; intramuscular 0.25/lb. every six hours, not to exceed 75/mg/day), or haloperidol (oral 5-10 mg/day orally; 0.05-10 mg/day I.V.). Also useful as a prokinetic agent, for purposes of the present invention, is a kappa agonist, such as fedotozine (1-30 mg/day), but not excluding other opiate agonists. The opiate (opioid) agonists, such as fedotozine, are particularly effective in alleviating or improving hyperalgesia related to SIBO or associated with disorders caused by SIBO, such as IBS, fibromyalgia, or Crohn's disease.

The preceding are merely illustrative of the suitable means by which small intestinal bacterial overgrowth is at least partially eradicated by treatment in accordance or in combination with the inventive methods. These means can be used separately, or in combination, by the practitioner as suits the needs of an individual human subject.

Optionally, treating further includes administering to the human subject an anti-inflammatory cytokine or an agonist thereof substantially simultaneously with or after at least partially eradicating the bacterial overgrowth of the small intestine, to accelerate or further improve the symptom(s) of irritable bowel syndrome, fibromyalgia, chronic fatigue syndrome, depression, ADHD, or an autoimmune disease, or Crohn's disease. Useful anti-inflammatory cytokines include human IL-4, IL-10, IL-11, or TGF-$\beta$, derived from a human source or a transgenic non-human source expressing a human gene. The anti-inflammatory cytokine is preferably injected or infused intravenously or subcutaneously.

Optionally, when the suspected diagnosis is irritable bowel syndrome, fibromyalgia, chronic fatigue syndrome, depression, ADHD, or an autoimmune disease, such as multiple sclerosis or systemic lupus erythematosus, symptoms are improved by administering an antagonist of a pro-inflammatory cytokine or an antibody that specifically binds a pro-inflammatory cytokine. The antagonist or antibody is administered to the human subject substantially simultaneously with or after treatment to at least partially eradicate the bacterial overgrowth. The antagonist or antibody is one that binds to a pro-inflammatory cytokine or antogonizes the activity or receptor binding of a pro-inflammatory cytokine. Pro-inflammatory cytokines include TNF-α, IL-1α, IL-1β, IL-6, IL-8, IL-12, or LIF. The cytokine antagonist or antibody is preferably derived from a human source or is a chimeric protein having a human protein constituent. The cytokine antagonist or antibody is preferably delivered to the human subject by intravenous infusion.

Optionally, the method of treating irritable bowel syndrome, fibromyalgia, chronic fatigue syndrome, depression, attention deficit/hyperactivity disorder, an autoimmune disease, or Crohn's disease, further comprises administering an agent that modifies afferent neural feedback or sensory perception. This is particularly useful when, after at least partial eradication of SIBO, the subject experiences residual symptoms of hyperalgesia related to SIBO or associated with a disorder caused by SIBO, such as IBS, fibromyalgia, or Crohn's disease. Agents that modify afferent neural feedback, or sensory perception include 5-HT receptor antagonists, such as ondansetron and alosetron; opiate agonists, such as fedotozine; peppermint oil; cisapride; a dopamine antagonist, such as domperidone; an antidepressant agent; an anxiolytic agent; or a combination of any of these. Useful antidepressant agents include tricyclic antidepressants, such as amitriptyline (Elavil); tetracyclic antidepressants, such as maprotiline; serotonin re-uptake inhibitors, such as fluoxetine (Prozac) or sertraline (Zoloft); monoamine oxidase inhibitors, such as phenelzine; and miscellaneous antidepressants, such as trazodone, venlafaxine, mirtazapine, nefazodone, or bupropion (Wellbutrin). Typically, useful antidepressant agents are available in hydrochloride, sulfated, or other conjugated forms, and all of these conjugated forms are included among the useful antidepressant agents. Useful anxiolytic (anti-anxiety) agents include benzodiazepine compounds, such as Librium, Atavin, Xanax, Valium, Tranxene, and Serax, or other anxiolytic agents such as Paxil.

Eradication of the bacterial overgrowth is determined by detection methods described above, particularly in comparison with recorded results from pre-treatment detection. After at least partially eradicating the bacterial overgrowth, in accordance with the present method, the symptom(s) of irritable bowel syndrome, fibromyalgia, chronic fatigue syndrome, depression, ADHD, an autoimmune disease, or Crohn's disease are improved. Improvement in a symptom(s) is typically determined by self-reporting by the human subject, for example by VAS scoring or other questionnaire. Improvement in academic, professional, or social functioning, e.g., in cases of ADHD or depression can also be reported by others or can be observed by the clinician. Improvement (increase) in pain threshold, e.g., in subjects diagnosed with fibromyalgia, can be measured digitally, for example, by tender point count, or mechanically, for example, by dolorimetry. (F. Wolfe et al., *Aspects of Fibromyalgia in the General Population: Sex, Pain Threshold, and Fibromyalgia Symptoms*, J. Rheumatol. 22:151-56 [1995]). Improvement in visceral hypersensitivity or hyperalgesia can be measured by balloon distension of the gut, for example, by using an electronic barostat. (B. D. Nabiloff et al., *Evidence for two distinct perceptual alterations in irritable bowel syndrome*, Gut 41:505-12 {1997]). Some improvement(s) in symptoms, for example systemic lupus erythematosus symptoms, such as rashes, photosensitivity, oral ulcers, arthritis, serositis, or improvements in the condition of blood, kidney or nervous system, can be determined by clinical observation and measurement.

The present invention also relates to a kit for the diagnosis of SIBO or a SIBO-caused condition. The kit comprises at least one breath sampling container, a pre-measured amount of a substrate, and instructions for a user in detecting the presence or absence of SIBO by determining the relative amounts of methane, hydrogen, and at least one sulfur-containing gas in a gas mixture exhaled by the human subject, after the human subject has ingested a controlled quantity of the substrate. The present kit is useful for practicing the inventive method of detecting SIBO in a human subject, as described hereinabove.

The kit is a ready assemblage of materials or components for facilitating the detection of small intestinal bacterial overgrowth, in accordance with the present invention. The kit includes suitable storage means for containing the other components of the kit. The kit includes at least one, and most preferably multiple, air-tight breath sampling container(s), such as a bag, cylinder, or bottle, and at least one pre-measured amount of a substrate, which is preferably an isotope-labeled substrate or substrate that is poorly digestible by a human. Preferably the substrate is a sugar, such as lactulose (e.g., 10-20 g units) or xylose, or a sugar, such as glucose (e.g., 75-80 g units), lactose, or sucrose, for measuring breath hydrogen, methane, and at least one sulfur-containing gas, such as hydrogen sulfide, a sulfhydryl compound, methanethiol, dimethylsulfide, dimethyl disulfide, an allyl methyl sulfide, an allyl methyl sulfide, an allyl methyl disulfide, an allyl disulfide, an allyl mercaptan, or a methylmercaptan.

The present kit also contains instructions for a user in how to use the kit to detect small intestinal bacterial overgrowth (SIBO) or to corroborate a suspected diagnosis of irritable bowel syndrome, fibromyalgia, chronic fatigue syndrome, chronic pelvic pain syndrome, autism, impaired mentation, impaired memory, depression, ADHD, an autoimmune disease, or Crohn's disease, in accordance with the present methods.

Optionally, the kit also contains compositions useful for at least partially eradicating SIBO, as described above.

The components assembled in the kits of the present invention are provided to the practitioner stored in any convenient and suitable way that preserves their operability and utility. For example the components can be in dissolved, dehydrated, or lyophilized form; they can be provided at room, refrigerated or frozen temperatures.

The foregoing descriptions for the methods and kits of the present invention are illustrative and by no means exhaustive. The invention will now be described in greater detail by reference to the following non-limiting examples.

EXAMPLES

Example 1

Composition of the Database

Data were assembled from 202 human subjects from, the Cedars-Sinai Medical Center GI Motility Program who completed an extensive questionnaire of health history. These patients were all referred for lactulose breath hydrogen testing (LBHT) by more than 30 private gastroenterologists. These patients were selected by, their gastroenterologists to undergo breath testing, because they had symptoms compatible with SIBO. However, the questionnaire focused on general risk factors, associated conditions, and symptoms found in these patients and not specifically the incidence of SIBO. After antibiotic therapy, 59 subjects actually returned for a follow up LBHT and a follow-up questionnaire. This likely resulted in an underestimate of responsiveness to treatment, since only those who failed to respond adequately were likely to return to assess eradication of SIBO.

Example 2

Breath Hydrogen Testing

Subjects were tested after an overnight fast. At time zero, each subject swallowed 15 ml of Chronulac formula, delivering 10 g of lactulose; every 5-20 min thereafter, for 2-4 hours, a 50 cm$^3$ end-expiratory breath sample was taken with an airtight sampling bag. Each breath sample was then analyzed for hydrogen content with a gas chromatograph (Quintron Model DP, Quintron Instrument Co., Division of E.F. Brewer Co, Menomonee Falls, Wis. 53051), standardized using a QuinGas standard as instructed by the manufacturer. Hydrogen peaks were plotted before and after an antimicrobial treatment regimen for comparison. The normal range for the second hydrogen peak was 0 to 20 ppm.

Example 3

Diagnosis and Antibiotic Treatment of Irritable Bowel Syndrome

The two hundred-two (202) human subjects were assessed for SIBO with LBHT. Of the 202 subjects in the database, 95 claimed to have been given a diagnosis of IBS. In addition, a symptom questionnaire was used to determine whether these subjects fulfilled Rome criteria for IBS, and four of the subjects failed to meet the Rome criteria. Crohn's disease was present in 14 of the subjects and four had a history of ulcerative colitis. After these 22 subjects were excluded, 73 subjects remained.

Among the 107 subjects who stated that they had not previously been given a diagnosis of IBS, 78 met Rome criteria. After the 21 who had Crohn's disease, five who had ulcerative colitis and one with short bowel transit were excluded, 51 subjects-remained. Data gathered from these subjects were pooled with, data from the previous 73 subjects with suspected IBS, yielding a total of 124 of the original 202 (61%) subjects with a suspected diagnosis of IBS.

Of the 124, 92 (74%) were positive for SIBO. However, of the 32 subjects meeting the Rome criteria, who were negative for SIBO, 14 had been treated with antibiotics within 3 months prior to LBHT. Therefore, the incidence of SIBO among the 110 untreated subjects was 92 (84%), showing a strong association between a suspected diagnosis of IBS and the presence of SIBO. After neomycin treatment (500 mg twice daily for ten days), 23 of these 92 returned for follow-up testing. On a visual analog scores (VAS), subjects were asked to rate their degree of post-treatment improvement. These 23 subjects reported a 60±31% improvement, although 17 had only partial eradication of SIBO, based on their LBHT results. (FIG. 1).

Figure 2:
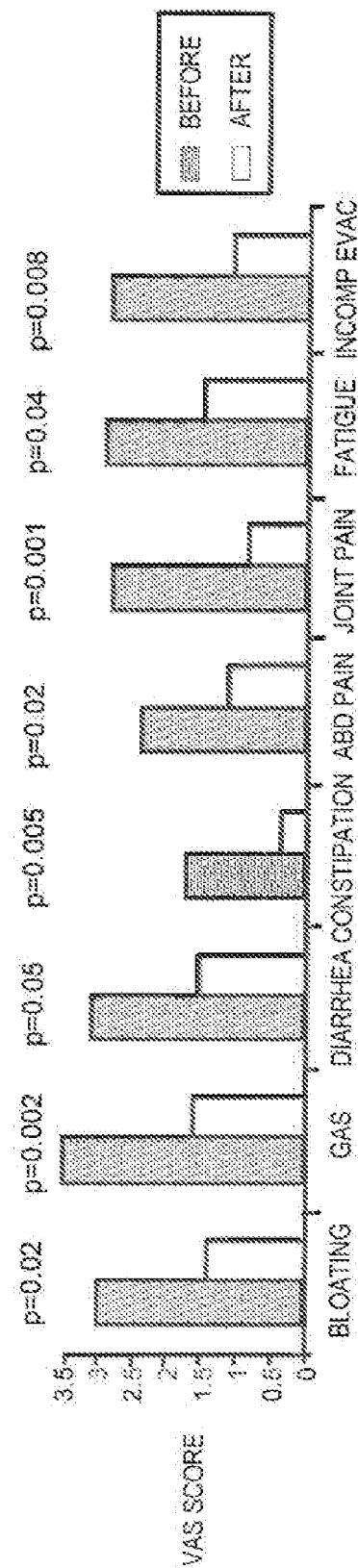
FIG. 2 shows visual analog scores from subjects with IBS and SIBO in a pilot study, before and after antibiotic treatment.

There was a likely selection bias in the database due to the fact that subjects were referred for LBHT, because their physicians suspected they had SIBO. To correct for this bias, a pilot study was also conducted looking at the incidence of bacterial overgrowth in patients with IBS. All patients between the ages of 18 and 65 referred to the Cedars-Sinai GI Motility Program who met Rome criteria for IBS, and who had had a previous upper GI (small bowel) with follow-through (i.e., barium or Gastrograffin imaging analysis) ruling out Crohn's disease and ulcerative colitis, were asked to present to the GI motility laboratory for LBHT. Eight human subjects with a suspected diagnosis of IBS, based on the Rome criteria, were tested for SIBO, using LBHT as described in Example 2. Seven of these patients (87.5%) were found to have SIBO based on hydrogen peaks in a range of 80-250 ppm of hydrogen. Six of the 7 subjects testing positive for SIBO returned approximately 10 days after completion of a 10 day course of neomycin as described above. Neomycin treatment completely eradicated the SIBO in each of the six subjects, based on post-treatment breath hydrogen peaks in the normal range of 0-20 ppm. The six subjects reported an average improvement in their IBS symptoms of 65±28% (Range: 20-100%) on VAS scoring. FIG. 2 shows, VAS for the six subjects, based on a scale of 0-5, with 0 implying no pain and 5 the most pain of life-time. It is clear from these results that at least partial eradication of bacterial overgrowth results in an improvement in gastrointestinal symptoms including bloating, gas, diarrhea, abdominal pain, sensation of incomplete evacuation and even constipation, associated with IBS. Additionally, significant extraintestinal symptoms of IBS, such as joint pain and fatigue, were also substantially improved, and the degree of improvement was greater in subjects-who had complete eradication of SIBO.

Comparison of Efficacies of Various Antibiotic Regimes for Treating SIBO.

Subjects referred to the Cedars-Sinai GI Motility Program for a lactulose breath hydrogen test (LBHT) to assess SIBO were entered into a database. Those that tested positive for SIBO were given antibiotic treatment by their referring physician and in some cases, returned for a follow-up LBHT to assess eradication of SIBO. During the follow-up LBHT, subjects were asked which antibiotic they were given to treat their SIBO. The eradication rate of each antibiotic was evaluated.

Of the 771 subjects in the database, 561 (73%) tested positive for SIBO. Of the 170 subjects who returned for a follow-up LBHT, 65 subjects were excluded because they did not specify or could not remember which antibiotic they took. Based on the remaining 105 subjects, neomycin, augmentin, and ciprofloxacin were the most commonly prescribed, with neomycin being most successful. (See Table 1 below). Flagyl was a relatively poor choice by itself. None of the commonly used antibiotics was universally successful in eradicating overgrowth. Thus, Table 1 shows that, while a number of antibiotics are able to eradicate SIBO, neomycin was most effective.

TABLE 1

Comparison of efficacies of various antibiotic regimes for treating SIBO

|  | Number of Patients SIBO Eradicated | Total Number | % Patients with SIBO Eradicated |
|---|---|---|---|
| Neomycin | 42 | 76 | 55 |
| Flagyl | 2 | 8 | 25 |
| Ciprofloxacin | 3 | 6 | 50 |
| Augmentin | 2 | 4 | 50 |
| Flagyl + Ciprofloxacin | 1 | 2 | —* |
| Tetracycline | 2 | 2 | —* |
| Doxycycline | 1 | 1 | —* |
| Trovan | 0 | 1 | —* |
| Neomycin/Biaxin + Amoxicillin | 1 | 1 | —* |

TABLE 1-continued

Comparison of efficacies of various antibiotic regimes for treating SIBO

|  | Number of Patients SIBO Eradicated | Total Number | % Patients with SIBO Eradicated |
|---|---|---|---|
| Neomycin + Ciprofloxacin | 1 | 1 | —* |
| Tetracycline + Flagyl | 1 | 1 | —* |
| Neomycin + Flagyl | 0 | 1 | —* |
| Biaxin | 0 | 1 | —* |

*Too few subjects to determine percent success.

Prevalence of SIBO in Normal Controls.

The prevalence of SIBO in IBS compared to normal controls was determined as defined by the lactulose hydrogen breath test. Fifty-seven IBS subjects enrolled in a double blind placebo controlled trial and 9 normal controls underwent a lactulose breath hydrogen test (LBHT) to diagnose SIBO. IBS subjects had to meet Rome I criteria. Control subjects had to have none of the Rome I criteria, based on telephone or in-person interviews. SIBO was defined as a greater than 20 ppm rise in $H_2$ concentration during the first 90 minutes of lactulose breath hydrogen testing. The prevalence of SIBO in IBS subjects and controls was compared using Chi-square.

Of the 57 IBS-subjects, 41 (72%) had SIBO. Of the 9 normal controls, only 1 subject (11%) had SIBO ($\chi^2$=9.9, OR=20.5, CI:2.2-481.8, p<0.01). These results confirm the association between IBS and SIBO as there is a much higher prevalence of SIBO in IBS compared to normal controls.

Example 4

Diagnosis and Treatment of Fibromyalgia and Chronic Fatigue Syndrome

Fibromyalgia:

Of the 202 patients in the database, 37 (18%) had a suspected diagnosis of fibromyalgia. Of these 37, 28 tested positive for SIBO. However, of the nine who tested negative for SIBO, six had taken antibiotics within the preceding 3 months, and were excluded. Therefore, 28 out of 30 (93%) of subjects with suspected fibromyalgia had SIBO, demonstrating a strong association between a suspected diagnosis of fibromyalgia and the presence of SIBO.

Figure 3:
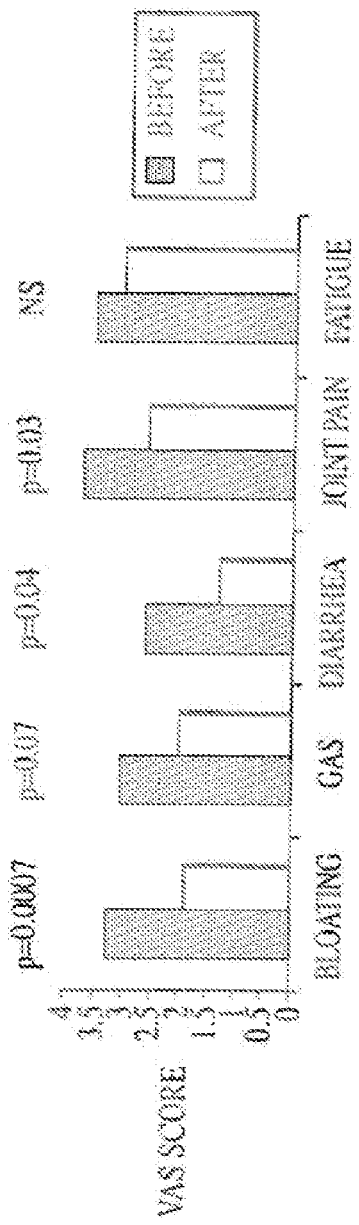
FIG. 3 shows visual analog scores reported by subjects with fibromyalgia and SIBO before and after antibiotic treatment.
Figure 4:
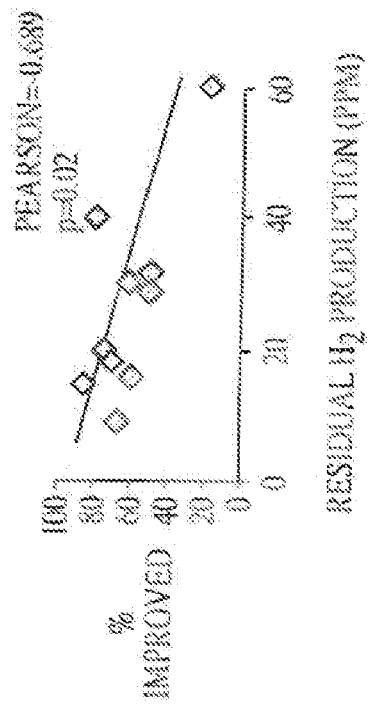
FIG. 4 shows the correlation between the degree of improvement in symptoms and residual breath hydrogen production after antibiotic treatment in subjects with fibromyalgia and SIBO.

After neomycin treatment (500 mg twice daily, 10-day course), ten of these 28 subjects returned, and post-treatment LBHT confirmed that SIBO had been at least partially eradicated. These ten subjects reported a 63±19% overall improvement in their symptoms by VAS scoring. FIG. 3 compares the VAS scores for various, symptoms reported by the subjects with a suspected diagnosis of fibromyalgia before and after neomycin treatment. Symptoms included bloating, gas, diarrhea, joint pain and fatigue to treatment. Subjects were asked to identify the symptom most improved. Five subjects reported that pain was the most improved; three subjects reported that the level of fatigue was most improved, and two others reported that their abdominal complaints improved the most. There was a negative correlation between the degree of improvement in the VAS scoring and the amount of residual hydrogen peak seen in LBHT. (Pearson=−0.689, p=0.02; FIG. 4).

Subsequently, forty-six human subjects with FM (ACR criteria) entered a double blind randomized placebo controlled trial. Each subject underwent LBHT, a tender point examination and completed a questionnaire at the initial (baseline) and at every subsequent visit. Subjects were randomized to receive neomycin (500 mg twice daily in liquid form) or a matched placebo, for 10 days. After completion of this treatment, subjects with persistent SIBO received antibiotics (open label) until at least partially eradication was confirmed by LBHT. T-test was used to compare the symptom scores of patients whose SIBO condition was at least partially eradicated with those whose SIBO was not at least partially eradicated.

Forty-two of the 46 FM patients (91.3%) were found to have SIBO. Six out of 20 patients (30%) in the neomycin group achieved complete at least partially eradication in the blinded arm. Only 6 subjects showed no difference in the symptom-score before and after the 10 d treatment. Twenty-eight subjects went on to open label treatment with 17 (60.7%) achieving complete at least partially eradication of SIBO. When symptom scores after at least partially eradication of SIBO on double blind or open treatment were compared to baseline, there was significant improvement in Tender Points, Tender Point Score, Hamilton Depression Scale, Fibromyalgia Impact Questionnaire (FIQ), Beck Depression Scale, Health Assessment Questionnaire (HAQ), VAS-Pain, VAS-Memory/Concentration and IBS-Quality of Life (QOL). (Initial data in Table 1a). These results confirm that SIBO is associated with fibromyalgia, and that at least partially eradication of SIBO improves symptoms in fibromyalgia.

TABLE 1a

Selected Symptom Scores Double Blind Randomized Placebo Controlled Trial with Subjects Diagnosed with Fibromyalgia.

| Observation | Baseline | SIBO eradicated (n = 25) eradicated | P-value | Baseline | SIBO not eradicated (p = 15) eradicated | P-value | eradicated vs. not eradicated P-value |
|---|---|---|---|---|---|---|---|
| Tender Points (TP) | 13.3 ± 2.9 | 10.3 ± 4.2 | 0.01 | 13.6 ± 2.0 | 12.1 ± 4.1 | NS | NS |
| TP Score | 20.3 ± 7.0 | 15.0 ± 9.1 | 0.01 | 23.7 ± 8.0 | 19.9 ± 9.7 | NS | NS |
| FIQ | 66.8 ± 18.2 | 49.5 ± 17.7 | 0.0001 | 72.7 ± 19.9 | 64.1 ± 20.9 | 0.04 | 0.02 |
| VAS-pain (mm) | 80.7 ± 22.7 | 52.4 ± 28.5 | 0.00005 | 87.5 ± 19.6 | 76.2 ± 25.2 | NS | 0.01 |
| HAQ | 42.4 ± 10.5 | 37.7 ± 10.1 | 0.005 | 45.1 ± 11.2 | 43.9 ± 12.1 | NS | NS |

Chronic Fatigue Syndrome:

Thirty of 202 subjects in the database (15.9%) had received a diagnosis of chronic fatigue syndrome. Of these 30 subjects, 21 (70%) had SIBO as indicated by LBHT, but four out of the nine without SIBO had recently taken antibiotics. Therefore, the prevalence of SIBO was 21 out of 26 (81%) subjects with a diagnosis of CFS. After treatment with neomycin (500 mg twice daily, 10-day course), nine of the 21 subjects diagnosed with CFS, returned for follow-up LBHT and questionnaire.

LBHT showed that all nine subjects experienced at least partially eradication of SIBO, and important symptoms of CFS were substantially improved after-treatment. (Table 2).

TABLE 2

VAS scores by CFS patients reporting before and after anti-biotic treatment.

| Symptom | Before Antibiotic | After Antibiotic | P-value |
| --- | --- | --- | --- |
| Bloating | 4.3 ± 1.0 | 2.3 ± 1.7 | 0.002 |
| Fatigue | 4.6 ± 1.0 | 3.5 ± 1.4 | 0.02 |

Example 5

Autoimmune Diseases, Depression, ADHD, Autism Mentation and Memory

SLE.

Fifteen of the 202 (7.4%) subjects in the database had been diagnosed with SLE. Of these 15 subjects, 13 (87%) had bacterial overgrowth, as indicated by LBHT. Four of the 15 subjects with SLE returned for follow-up LBHT and questionnaire after treatment with neomycin (500 mg twice daily for 10 days). LBHT results for these four were negative for SIBO, and other significant symptoms were significantly improved after treatment. (Table 3).

TABLE 3

VAS scores by SLE patients reporting before and after anti-biotic treatment.

| Symptom | Before Antibiotic | After Antibiotic | P-value |
| --- | --- | --- | --- |
| Bloating | 3.0 ± 2.0 | 1.3 ± 1.3 | 0.1 |
| Joint Pains | 2.5 ± 1.5 | 0.5 ± 0.6 | 0.04 |
| Gas | 3.3 ± 1.7 | 1.9 ± 1.7 | 0.3 |
| Fatigue | 4.6 ± 1.0 | 3.5 ± 1.4 | 0.3 |

Multiple Sclerosis:

A 22-year-old female who presented with a history of multiple sclerosis symptoms and with plaques demonstrated on MRI imaging. A suspected diagnosis of multiple sclerosis had been made by a neurologist was based on various neuropathies of the peripheral nervous system, including numbness, tingling and weakness in the lower extremities, but this subject also had associated bloating, gas, distension and alteration in bowel habits. The subject also complained of a significant fatigue and nausea. The subject underwent LBHT, which detected SIBO. She was subsequently treated with neomycin (500 mg twice daily for 10 days), which at least partially eradicated the bacterial overgrowth. This was followed by complete resolution of her nausea, fatigue, bloating, gas distension and alteration in bowel habits. In addition, the subject showed dramatic improvement and resolution of her neuropathies. She no longer had numbness or tingling in the hands or feet and was functioning quite well. Approximately 6-8 weeks after this initial response, the patient had a relapse of her symptoms, including bloating, gas, distension and neuropathy. She had a repeat LBHT that confirmed a recurrence of SIBO. Upon re-treatment with neomycin (500 mg twice daily for 10 days), she once again experienced complete resolution of her symptoms.

Depression:

A 73-year-old female presented with bloating, gas, abdominal distension, and cramping for a period of 3 years prior to LBHT. Symptoms of depression first appeared concurrently with the first appearance of bowel symptoms, and were serious enough that psychiatric hospitalization had been considered by her attending psychiatrist. The subject reported feeling very depressed and was convinced that life was: not worth living. The subject's LBHT indicated the presence of a SIBO condition. After treatment with neomycin (500 mg twice daily for 10 days), the subject stated that she felt "100% better." She reported that her depression was completely resolved and that her energy was back to normal. In addition, her bowel symptoms were also completely improved. The subject had been prescribed eight different anti-depressant medications, all of which were discontinued as a result of her improvement.

ADHD:

A 13 year-old female was, brought in by her mother with a suspected diagnosis of attention deficit/hyperactivity disorder (AD type), made by a pediatrician. Concurrently, she also had significant bloating, gas and some alteration in bowel habits. She had initially been referred for diagnosis by her teachers and school counselors, because she had been having difficulty performing in school for the previous two to three years, after having previously been a very good student. Prior to the detection of SIBO, the subject had been treated with multiple pharmacologic agents for depression, including amitryptyline, with no noticeable improvement in her symptoms.

The subject underwent LBHT that demonstrated the presence of SIBO. The subject was treated with neomycin. (500 mg twice daily for 10 days) and after complete at least partially eradication of the bacterial overgrowth, she had resolution of her bowel symptoms. Additionally, she started to get "A" averages in school again after being in the "C" range. She was able to concentrate better, and her teachers noticed a difference in her focus and attitude. Approximately two months later the subject had a relapse in her attention problem which was concurrent with a recurrence of the bacterial overgrowth, as detected by LBHT. After repeat treatment with neomycin (500 mg twice daily for 10 days), the subject again responded with improved concentration and resolution of bowel symptoms.

Autism:

The patient was a 6-year-old female with a history of autism after having failed development after the age of one year. Before treatment, the patient was categorized as having a developmental age of 15 months. She also complained of abdominal distension, gas, bloating and altered bowel habits. The patient was treated with Augmentin (500 mg twice a day for ten days), which resulted in a substantial improvement in bowel habits altogether. The bloating, gas, distension and diarrhea resolved. In addition, there were some positive concentration and behavioral changes. The patient was more responsive and cognitively appreciative of her parents' wishes, and there was some advancement in intellectual behavior. For example, after treatment she was able to tolerate clothing and had improved concentration.

Memory/Mentation/Concentration:

The patient was a 72-year-old female with a history of chronic intestinal complaints over several years. She experienced altered bowel habits with alternating diarrhea and constipation with bloating, gas, distension and abdominal pain. Also, she had been diagnosed by several psychiatrists as having psychiatric problems due to decreased mentation from mild senility, and she contemplated psychiatric hospitalization.

SIBO was detected in this patient by LBHT. A subsequent course of antibiotics completely eradicated the SIBO condition, and she returned to report joyfully that she no longer needed the psychotropic medications that, she had been prescribed, because she feels completely normal, including her bowels. She is now able to drive a car again, which was previously prevented from doing due to her impaired memory and difficulty in concentrating on the road. Treatment of her SIBO condition (neomycin, 500 mg twice a day for ten days) has produced a dramatic improvement in her quality of life.

Example 6

Diagnosis and Treatment of Crohn's Disease

Of the 202 subjects in the database, 39 (19%) had a suspected diagnosis of Crohn's disease. Of these 39, eight demonstrated short bowel transit and one subject produced neither hydrogen nor methane in LBHT; these nine were excluded. Of the 30 remaining subjects, 22 had SIBO. However, of the eight subjects who had a negative LBHT result, five had been treated with antibiotics within the preceding 3 months. If these subjects are excluded, 22 out of 25 (88%) subjects with a suspected diagnosis of Crohn's disease had SIBO, which shows a strong association between a suspected diagnosis of Crohn's disease and the presence of SIBO.

Figure 5:
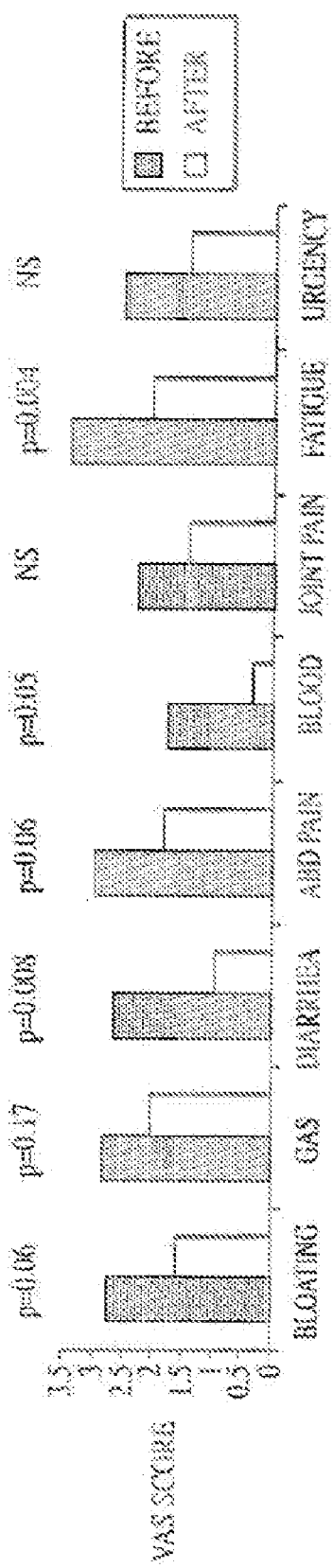
FIG. 5 shows visual analog scores reported by subjects with Crohn's disease and SIBO before and after antibiotic treatment.

Of the 22 patients testing positive for the presence of SIBO, nine returned after neomycin treatment (10-day course of 500 mg twice/daily) for LBHT, which showed at least partially eradication of SIBO. These nine patients reported a 57±32% (n=8 because one patient failed to report percent improvement) overall improvement in their symptoms by VAS. If these subjects remained positive after antibiotic treatment with neomycin, metronidazole (Flagyl®), or ciprofloxacin, their improvement was only 20±0% as opposed to 69±27% if the breath test was negative (p<0.05). FIG. 5 shows a dramatic improvement in the patients symptoms after treatment. There was an especially notable reduction in bloody stools, diarrhea and fatigue.

Figure 6:
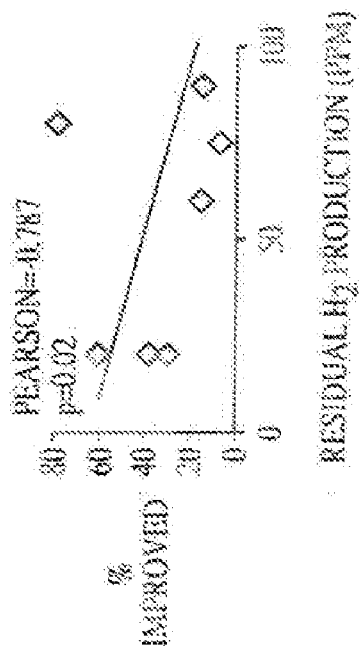
FIG. 6 shows the correlation between degree of improvement in symptoms and residual breath hydrogen production after antibiotic treatment in subjects with Crohn's disease.

As with the subjects with fibromyalgia, there was a negative correlation between the degree of improvement in the VAS scoring and the amount of residual hydrogen production (Pearson=−0.787, p=0.02; FIG. 6).

To correct for selection bias, a pilot study was conducted to determine the incidence of SIBO in subjects who had received a suspected diagnosis of Crohn's disease at Cedars-Sinai Medical Center's IBD Center within the preceding three months. Six of these subjects underwent LBHT, of whom five (83%) were positive for SIBO.

Two of the six subjects returned for follow-up after antibiotic therapy (10-day course of neomycin). Post-treatment LBHTs showed that SIBO had been completely at least partially eradicated in both subjects. They reported, respectively, a 60% and 80% overall improvement in their symptoms. This improvement was stated to include substantial reduction in diarrhea, gas and bloating.

Example 7

Response Stratification

There is a stratification in the degree of overgrowth and production of hydrogen among the various diagnostic categories. For example, during the double blind study in the treatment of SIBO in fibromyalgia (Example 4), it was noted that the level of hydrogen production during the LBHT was much higher in this group of subjects as compared to those in subjects in the IBS incidence study described in Example 3. Given that the bacterial, load is related to the level of hydrogen production, this implies that the degree of overgrowth is higher in patients with fibromyalgia compared to subjects with IBS.

The stratification of breath hydrogen levels with respect to diagnostic categories is as follows: IBS/Crohn's Disease (40-70 ppm of hydrogen); CFS (50-100 ppm of hydrogen); and FM (100-250 ppm of hydrogen).

Example 8

Intestinal Dysmotility Associated with IBS and FM

Clinical experience showed that SIBO tends to recur after anti-biotic treatment within about 2 months. To demonstrate that a lack of phase UI interdigestive motility is responsible for SIBO in subjects with IBS or fibromyalgia, antreduodenal manometry was conducted in human subjects diagnosed with IBS or FM.

Antreduodenal Manometry.

Phase interdigestive (fasting) motility was assessed in 15 human subjects. An antreduodenal manometry was performed by placing an 8-channel small bowel manometry catheter (each channel spaced 5 cm apart) into the small bowel using fluoroscopic guidance. After placement of the catheter, manometric recordings were made with an, Arndorffer perfusion system with signals collected using Medtronics/Synectics Polygraf and associated Polygram software. Data were assessed for the characteristics of interdigestive motility.

IBS.

Phase III interdigestive motility was assessed for a six-hour period in 15 human subjects having a suspected diagnosis of IBS, as defined by Rome Criteria, corroborated by concomitant SIBO. Of these 15 subjects, 13 (86%) had no detectable phase III interdigestive motility during the period of study. One subject (7%) had phase III interdigestive motility of short duration (<3 minutes), and one subject (7%) had normal phase III interdigestive motility.

Fibromyalgia.

Phase III interdigestive motility was assessed in seven human subjects having a suspected diagnosis of fibromyalgia corroborated by the presence of SIBO. Of these seven subjects, six (86%) lacked detectable phase III interdigestive motility, and one subject (14%) had motility of less than normal peristaltic amplitude. The duration of study in the patients with fibromyalgia averaged 216±45 minutes in the fasting state.

Example 9a

Treatment of SIBO-Related IBS with a Prokinetic Agent

Erythromycin, as a motilin agonist, can induce phase III of interdigestive motility. (E.g., M. J. Clark et al., *Erythromycin derivatives ABT229 and GM 611 act on motilin receptors in the rabbit duodenum*, Clin. Exp. Pharmacol. Physiol. 26(3): 242-45 [1999]). Therefore, two subjects with recurrent IBS symptoms received prokinetic treatment with erythromycin.

The two subjects were a 55-year-old female and a 43-year-old female, both diagnosed with IBS. SIBO was detected in these subjects by LBHT. Antibiotic treatment of the SIBO resulted in greater than 90% improvement in symptoms. However, IBS symptoms recurred three to four weeks later, concurrent with a return of the SIBO condition. Subsequent courses of antibiotic treatment resulted in a similar pattern of improvement followed by a rapid recurrence of IBS symptoms in both subjects. Antreduodenal manometry was performed, demonstrating a lack of phase III of interdigestive motility, and erythromycin (50 mg daily) was prescribed to the subjects. The two subjects subsequently remained free of IBS symptoms and SIBO for at least 18 months and six months, respectively.

These results demonstrate the effectiveness of prokinetic treatment with erythromycin in preventing the recurrence of SIBO and IBS symptoms in subjects diagnosed with IBS.

Example 9b

Treatment of SIBO-Related IBS with a Supplemental Pancreatic Enzyme

Supplementing food with pancreatic enzymes facilitates more efficient absorption and digestion of food nutrients, thus allowing ingested food nutrients to be absorbed higher up in the small intestine than otherwise. This leads to a relative deprivation of nutrients to the bacteria involved in the SIBO condition. An example of this treatment modality occurred in the case of a 19-year-old male who had longstanding history of altered bowel habits, bloating, gas, distension and significant urge to evacuate. All of these symptoms were consistent with irritable bowel syndrome (IBS). The patient was diagnosed as having SIBO based on the results of LBHT. Subsequent to treatment with antibiotics, the patient had significant improvement in his symptoms. However, his SIBO condition became difficult to manage due to antibiotic resistance. An alternative treatment regimen was prescribed, which involved the addition of a pancreatic enzyme to the patient's food (10,000 Units human pancrease in capsules ingested immediately before each meal). With this therapy, the patient reported that his gastrointestinal complaints have improved by approximately 30-40%, corresponding to partial eradication of his SIBO condition. Treatment was continued for at least eight months with a continuation of the improvement in symptoms during that period.

Example 9c

Excessive Methane Production in Subjects with Small Intestinal Bacterial Overgrowth is Associated with Less Diarrhea Bacterial metabolism is the major mechanism for the removal of hydrogen that is produced during fermentation reactions of intestinal bacteria. Specifically, hydrogen is consumed in the production of methane and in the reduction of sulfates to sulfides, with the 2 pathways being mutually exclusive. Since intestinal sulfides are known to be damaging to intestinal epithelium, it was hypothesized that diarrhea may be a less prevalent symptom among patients with small intestinal bacterial overgrowth (SIBO) who test positive for methane (no damaging sulfides produced).

Subjects referred to the Cedars-Sinai GI Motility Program for LBHT were entered into a database. Subjects were asked to rate symptoms of bloating, diarrhea, constipation, abdominal pain, mucous in stool, incomplete evacuation, straining and urgency, on visual analogue scales (0-5, with 0 representing no symptoms). An ANOVA was used to compare symptom scores between subjects producing no measured gases (only sulfide producing bacteria), $H_2$ only, $H_2$ and $CH_4$, and $CH_4$ only, on the LBHT.

Figure 7:
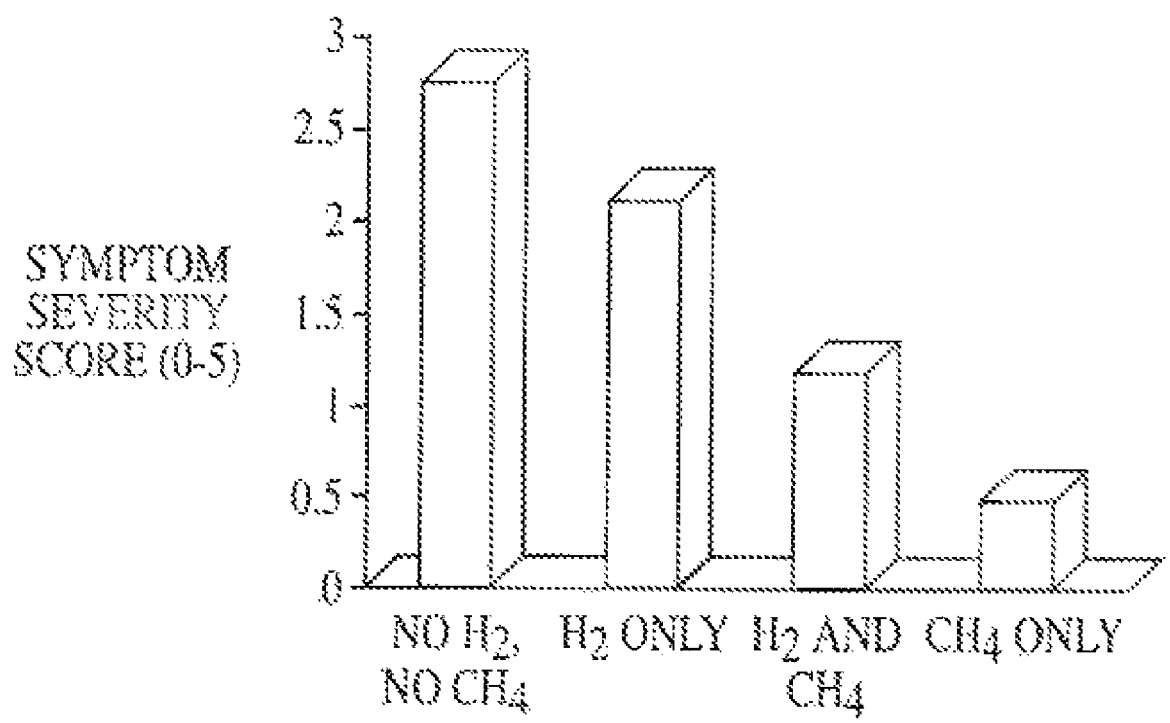
FIG. 7 shows that the severity of diarrheal symptoms is comparatively less in SIBO patients who excrete methane.

Of the 771 subjects in the database, 48 were excluded because they demonstrated rapid transit on the LBHT. Of the 723 subjects remaining, 514 were positive for SIBO and 43 were considered non-methane, non-hydrogen producers. Among the 514 who had SIBO, 435 (85%) produced $H_2$ only, 68 (13%) produced both $H_2$ and $CH_4$, and 11 (2%) produced $CH_4$ only. The severity of diarrhea was highest in the non-$H_2$, non $CH_4$ and $H_2$ only group with less in the $H_2$ and $CH_4$ group, and $CH_4$ only group. There was a significant difference between the three groups for diarrhea (p<0.00001 after Boneferroni correction). Urgency demonstrated the same trend, but was not significantly different. All other symptoms were no different. The severity of diarrheal symptoms is less in SIBO patients who excrete methane (FIG. 7). In the non-methane-producers, greater severity of diarrheal symptoms likely reflects the reduction of sulfates to sulfides as the alternate pathway for the removal of hydrogen.

Example 10

Treatment of SIBO-Related Hyperalgesia

An adult male subject with a suspected diagnosis of IBS was found to have SIBO, as detected by LBHT Anorectal manometry revealed rectal hypersensitivity in this subject. After eradication of his SIBO condition with antibiotic treatment, a repeat anorectal manometry showed that his rectal hyperalgesia had resolved.

Two adult female subjects with IBS required additional pharmacologic manipulations to treat their SIBO-related hyperalgesia. In the first case, SIBO was eradicated by antibiotic treatment. However, the subject complained of persistent feelings of rectal distension, consistent with residual hyperalgesia related to SIBO. The subjected was then administered Colpermin (peppermint oil) capsules and Elavil (5 mg taken at night) that alleviated her SIBO-related hyperalgesic symptoms, presumably by reducing intestinal wall tension and decreasing mechanoreceptor activation.

The second female subject with a diagnosis of IBS was also found to have SIBO, as detected by LBHT. Her SIBO was eradicated by a combined treatment with antibiotic, intestinal lavage with Go-Lytely, and cisapride (10 mg tid) to increase her abnormally low phase III interdigestive motility. After eradication of SIBO, this subject similarly complained of persistent SIBO-related hyperalgesic symptoms of the bowel. Administration of Colpermin (peppermint oil) then successfully alleviated the hyperalgesia, presumably by reducing the mechanoreceptor feedback for rectal distension.

Example 11

Treatment of SIBO Using Predigested Nutritional Formula

Based on the hypothesis that SIBO is promoted by nutritional components in food arriving at the distal gut, where they are used for carbon and energy by bacterial populations responsible for the SIBO condition, ten patients (8 female; 2 male; age range 17-64 years old, none having had a bowel resection) each diagnosed with IBS in accordance with the Rome Criteria, and each having SIBO as determined by LBHT, were treated with a total enteral nutrition (TEN) formula, which is absorbed in the proximal gut (Vivonex® T.E.N.; Sandoz Nutrition, Minneapolis, Minn.). Vivonex is a glutamine-enriched total enteral nutrition product, containing protein as free amino acids in a 56:44 essential to nonessential amino acid ratio, and inter alia, carbohydrate as maltodextrin and modified starch, safflower oil, and all essential vitamins and minerals. Vivonex is available as a powder for aqueous reconstitution (2.84 oz. packet; 1 packet mixed with 250 mL H$_2$O delivers 300 mL of formula). Each patient was administered an amount of reconstituted Vivonex to meet daily caloric needs according to the manufacturer's instructions, based on the each patient's weight, height and other relevant factors. The patient's were allowed no other nutritional intake, but water was allowed freely. After 14 days of the TEN regimen, each patient resumed his or her normal diet.

Figure 8A:
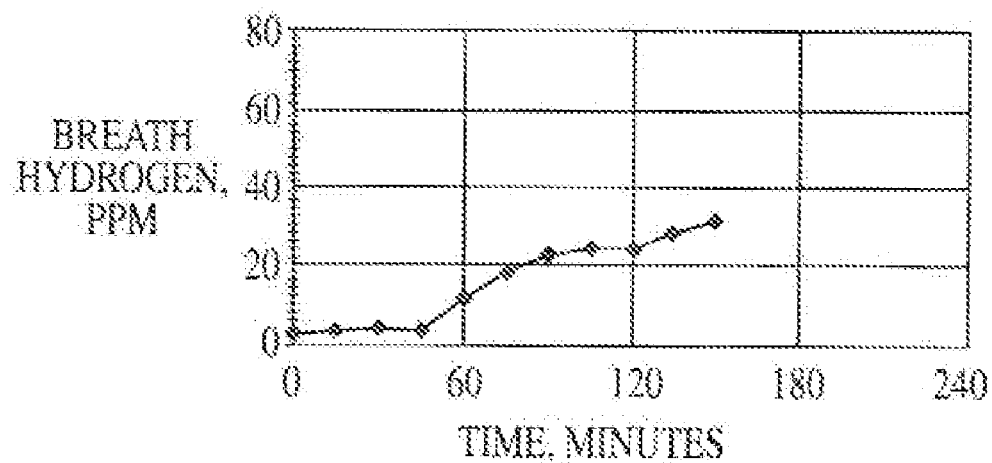
In FIG. 8A (pre-treatment), SIBO was initially detected. After 14 days of the TEN regimen, follow-up LBHT shows that SIBO had been at least partially eradicated (FIG. 8B).
Figure 8B:
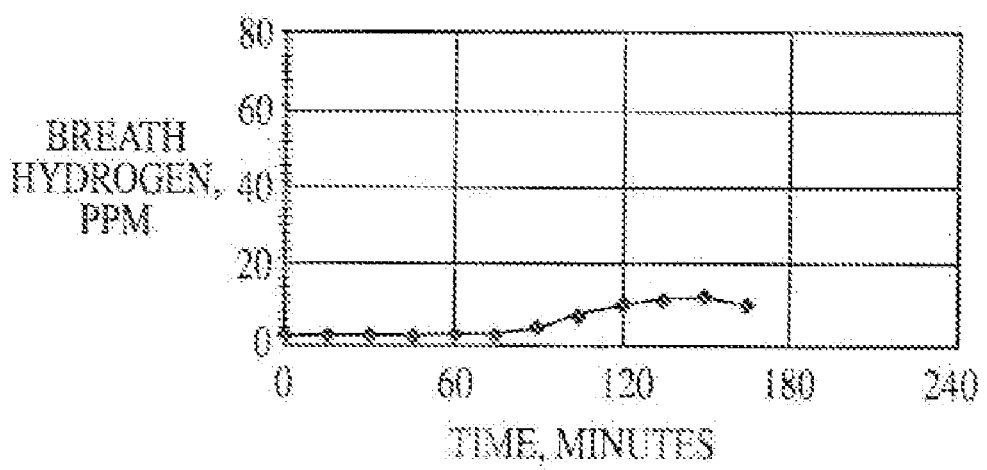
FIG. 8 shows a typical effect of total enteral nutrition (TEN) regimen in the eradication of SIBO as detected by LBHT.
Figure 9:
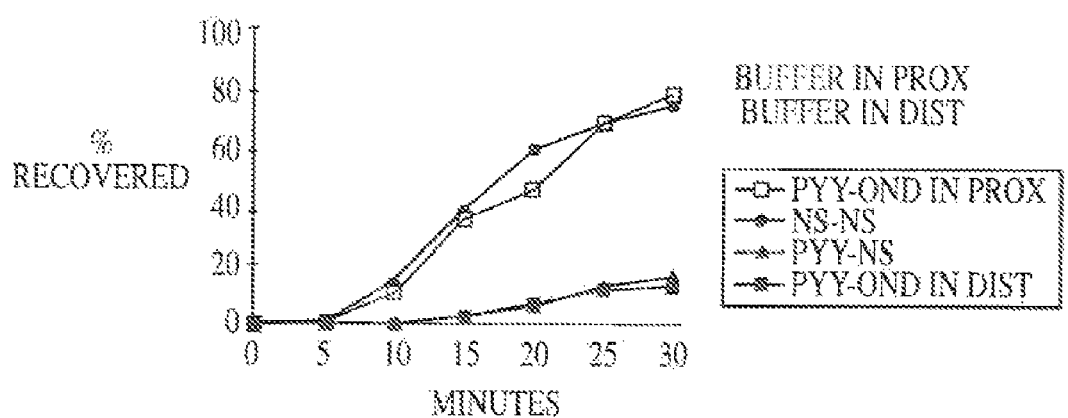
FIG. 9 demonstrates that slowing of the rate of intestinal transit by fat depends on peptide YY (PYY), which is a physiological fat signal molecule.

FIG. 8 shows a representative result. In FIG. 8A (pre-treatment), SIBO was initially detected by LBHT. After 14 days of the TEN regimen, follow-up LBHT shows that SIBO had been at least partially eradicated (FIG. 8B). Eradication was complete in eight of the patients with a greater than 80% improvement in IBS symptoms. Two of the patients had only partial eradication of SIBO with <20% improvement in IBS symptoms. The eradication of SIBO was maintained for up to two months after the TEN regimen was discontinued and normal nutrition had been resumed.

Example 12

Use of Active Lipids to Treat SIBO-Related Conditions

Oleate and Oleic Acid Slow Upper Gut Transit and Reduce Diarrhea in Patients with Rapid Upper Gut Transit and Diarrhea Rapid transit through the upper gut can result in diarrhea, maldigestion and absorption, and weight loss; and pharmacologic treatment with opiates or anticholinergics often is required. It was tested whether fatty acids could be used to slow upper gut transit and reduce diarrhea in patients with rapid transit and diarrhea.

In a preliminary study, five patients with persistent diarrhea for 3 to 22 months, (one each due to vagal denervation, ileal resection for Crohn's disease, and vagotomy and antrectomy, and two due to idiopathic causes) were studied. Each patient demonstrated rapid upper gut transit on routine lactulose breath hydrogen testing (or variations thereof measuring labelled carbon dioxide) (Cammack et al. *Gut* 23:957-961 [1982]). This test relies on the metabolism of certain carbohydrate materials (e.g. lactulose) by the microbial flora within the caecum. By generating gas which can be detected in the expired air, it is possible to make some estimation about the initial arrival of the administered material within the colon.

Each patient received orally in random order, 0, 1.6 or 3.2 g of sodium oleate in 25 mL Ensure (Ross), followed by 100 mL water. Thirty minutes after each dose of oleate, patients received 10 g lactulose orally, followed by 25 mL water. Breath samples were collected in commercially available breath testing bags (Quintron, Menomonee Falls, Wis.) every 10-15 minutes, and the hydrogen content of the samples was measured using a breath analyzer (Microlyzer Model 12, Quintron Instruments, Menomonee Falls, Wis.), calibrated against gas samples of known hydrogen concentration. With a syringe, a 40-mL sample of the expired breath was withdrawn from the collection bag and analyzed immediately for hydrogen concentration (ppm). The hydrogen concentration value from each sample was plotted against time. Upper gut transit time was defined as the time in minutes from ingestion of lactulose ($t_0$) until a rise of H$_2$ of >10 ppm. Data were further analyzed using 1-way repeated measures analysis of variance (ANOVA) (See Table 4).

TABLE 4

Effect of oleate on upper gut transit time (mean ± SE).

| | Oleate (g) | | |
|---|---|---|---|
| | 0 | 1.6 | 3.2 |
| Transit time (min) | 46 ± 8.6 | 116 ± 11.1 | 140 ± 11.5 |

Upper gut transit was significantly prolonged by oleate in a dose-dependent fashion (p<0.005, significant trend). During prolonged ingestion of oleate 15-30 minutes prior to meals, all patients reported reduced diarrhea. The patient with Crohn's disease reported complete resolution of chronic abdominal pain as well as post prandial bloating and nausea, and gained 22 lbs. In addition, the patient with vagotomy and antrectomy reported resolution of postprandial dumping syndrome (flushing, nausea, light-headedness).

The effect of an active lipid on transit time was determined in 8 normal human subjects (1 male and 7 females with a mean age of 35±2.6 years [SE]) and 45 patients (20 males and 25 females with a mean age of 49.1±2.5 [SE], age range from 18 to 90 years) with chronic diarrhea (i.e., continuous diarrhea for more than two months) associated with a wide variety of diagnoses and conditions (e.g., Crohn's disease; irritable bowel syndrome; short bowel syndrome; Indiana pouch; AIDS; ulcerative colitis; vagotomy; antrectomy; ileostomy; partial and complete colectomy; colon cancer; diabetes mellitus type 1; pancreatic insufficiency; radiation enteropathy; esophagectomy/gastric pull-up; total and subtotal gastrectomy; gastrojejunostomy), made by referring gastroenterologists. The method was the same as described above, except oleic acid (Penta Manufacturing, Livingston, N.J.) replaced sodium oleate in 50 mL of Ensure emulsion. All subjects refrained from taking antibiotics for at least two weeks before each testing date and during stool measurement periods. Patients were also instructed to refrain from anti-diarrheal drugs, laxatives, somatostatin analogues or anticholinergics for at least 48 hours before each test. In both the normal and patient groups, there was a significant slowing of upper gut transit time in response to oleic acid, as summarized in Table 5 below (p<0.001).

TABLE 5

Effect of Oleic Acid on upper gut transit time.

| | Transit time (min) (mean ± SE) | | |
|---|---|---|---|
| | Oleic Acid (g) | | |
| | 0 | 1.6 | 3.2 |
| Normal | 105.2 ± 12.1 | 116 ± 11.1 | 140 ± 11.5 |
| Patients | 29.3 ± 2.8 | 57.2 ± 4.5 | 83.3 ± 5.2 |

Continuing oleic acid treatment at home was offered to "responders" (i.e., patients who experienced a greater than 100% increase in baseline transit time with 3.2 g oleic acid). Of the 36 responders out of the original 45 patients, 18 provided records of stool volume and frequency on- and off-treatment for comparison. The inconvenient and unappealing nature of stool collection and measurement were the primary reasons reported by responders who chose not to participate in stool collection. After completing a set of three preliminary breath hydrogen tests, each participating responder was asked to refrain from taking oleic acid for two days in order to measure off-treatment stool output for a 24-hour period. Patients were issued a stool pattern record form and a stool collection container with graduated volume markings to record the frequency and volume of bowel movements. After two days without oleic acid, each patient took 3.2 g of oleic acid mixed with 25 mL of Ensure emulsion three times a day, 30 minutes before breakfast, lunch and dinner. After taking oleic acid for two days, patients recorded stool output for another 24-hour period. With this oleic acid emulsion treatment, stool frequency decreased from 6.9±0.8 to 5.4±0.9 bowel movements per 24-hour period (p<0.05), and stool volume decreased from 1829.0±368.6 to 1322.5±256.9 per 24-hour period (p<0.05). A slight and transient burning sensation in the mouth or throat was the only adverse effect reported by any patient taking the oleic acid treatment.

These experiments demonstrate that active lipids, such as oleate and oleic acid, are effective in slowing upper gut transit in a dose-dependent manner, thus enabling longer residence time for food in the upper gut and a concomitant greater nutrient absorption there.

Fat in Distal Gut Inhibits Intestinal Transit More Potently than Fat in Proximal Gut.

In 4 dogs equipped with duodenal (10 cm from pylorus) and mid-gut (160 cm from pylorus) fistulas, as described hereinbelow (Example 14), intestinal transit was compared across, an isolated 150 cm test segment (between fistulas) while 0, 15, 30 or 60 mM oleate was delivered into either the proximal or distal segment of the gut as a solution of mixed micelles in pH 7.0 phosphate buffer at 2 mL/min for 90 minutes. The segment of gut not receiving oleate was perfused with phosphate buffer, pH 7.0, at 2 mL/min. 60 minutes after the start of the perfusion, −20 µCi of $^{99m}$Tc-DTPA (diethylenetriaminepentaacetic acid) was delivered as a bolus into the test segment. Intestinal transit was then measured by counting the radioactivity of 1 ml samples collected every 5 minutes from the diverted output of the mid-gut fistula.

Intestinal transit was calculated by determining the area under the curve (AUC) of the cumulative percent recovery of the radioactive marker. The square root values of the AUC (Sqrt AUC), where 0=no recovery by 30 minutes and 47.4=theoretical, instantaneous complete recovery by time 0, were compared across region of fat exposure and oleate dose using 2-way repeated measures ANOVA (see Table 6 below).

TABLE 6

Effect of Oleate and oleic acid on intestinal transit.

| Region of fat exposure | Oleate dose (mM) (mean ± SE) | | |
|---|---|---|---|
| | 15 | 30 | 60 |
| Proximal ½ of gut | 41.6 ± 1.4 | 40.6 ± 10.2 | 34.4 ± 3.0 |
| Distal ½ of gut | 25.6 ± 1.4 | 18.9 ± 1.5 | 7.0 ± 3.8 |

Control: buffer into both proximal and distal ½ of gut = 41.4 ± 4.6.

These experiments demonstrate that intestinal transit is slower when fat is exposed in the distal 1/2 of gut (region effect p<0.01). These experiments also demonstrate that oleate is effective to inhibit intestinal transit in a dose-dependent fashion (dose effect, p<0.05); and that dose dependent inhibition of intestinal transit by oleate depends on the region of exposure (interaction between region and dose, p<0.01).

Case Study Showing Successful Treatment of Diarrhea-Predominant Irritable Bowel Syndrome with Oleic Acid.

The patient was a 39-year old male with a history of adolescent-onset, persistent diarrhea. After a routine gastrointestinal work-up failed to provide an explanation for his symptoms, he was given the diagnosis of diarrhea-predominant irritable bowel syndrome. He presented with complaints of excessive gas, postprandial bloating, diarrhea and urgency, and 3 to 7 liquid bowel movements per day. His upper gut transit-times were (min) 30 (0 g oleic acid), 117 (1.6 g oleic acid) and 101 (3.2 g oleic acid). With continuing oleic acid treatment as described above, he reported his bowel frequency reduced to a single, solid bowel movement per day. He also reported complete relief from the symptoms of gaseousness, bloating and rectal urgency.

Relatively Rapid Basal Upper Gut Transit in Patients with Inflammatory Bowel Disease (IBD).

The mean upper gut transit time for IBD patients (n=18) at 0 grams of oleic acid was 79.1±11.0 min., compared to 118.7±9.8 min for normal subjects (n=5)(p=0.04, t-test).

Active Lipid Increases Upper Gut Transit Time.

The mean transit time for normal subjects (n=5) at 0 grams of oleic acid was 118.7±9.8 min, at 4 grams of Oleic acid was 136.0±15.4 min. (P<0.05, t-test). The mean AUC for normal subjects at 0 grams of oleic acid was 1438.9±208.5; at 4 grams, of oleic acid it was 1873.3±330.5 (p<0.05, t-test). The mean transit time for IBD patients (n=18) at 0 grams of oleic acid was 79.1±11.0 min; at 4 grams of oleic acid it was 114.6±16.0 min. (p<0.05, t-test). The mean AUC for IBD patients at 0 grams of oleic acid was 687.3±98.2; at 4 grams of oleic acid it was 1244.9±250.4. (p<0.05, t-test).

These data show that oleic acid slowed gut transit time and thus substantially increased the opportunity for absorption of food nutrients in the upper gut region in both normal and IBD groups. Thus, the in individuals having SIBO a condition, treatment in accordance with the method of deprives the bacteria of much of the nutrient supply required for growth.

Example 13

Eradication of SIBO in Subjects with Irritable Bowel Syndrome Lowers their Serum Levels of 5-HT Previous studies have shown that patients with irritable bowel syndrome (IBS) have elevated plasma 5-hydroxytryptamine (5-HT) levels. Since it was shown hereinabove that IBS is associated with small intestinal bacterial overgrowth (SIBO) and symptoms of IBS are reduced by antibiotic eradication of SIBO, the hypothesis was tested that eradication of SIBO will reduce plasma 5-HT levels in IBS patients to provide further evidence of the relationship between IBS and SIBO.

The plasma 5-HT levels of 7 human subjects diagnosed with IBS were compared before and after successful eradication of SIBO, as part of a double blind placebo controlled trial. A lactulose breath hydrogen test (LBHT) was performed to diagnose SIBO at baseline and when eradication was achieved. Fasting blood samples were taken at baseline and on the day that eradication of SIBO was confirmed. The plasma 5-HT level (ng/mL) was determined in each sample by ELISA (Kit-Research Diagnostics Inc., Flanders, N.J.). A paired t-test was performed to compare 5HT levels (mean±SE) before and after eradication of SIBO.

The results indicated that the amount of plasma 5-HT was reduced from 0.7±0.4 ng/mL before eradication to 0.5±0.5 ng/mL after eradication of SIBO in the subjects (p<0.05). Thus, eradication of SIBO in IBS subjects decreases fasting plasma 5-HT levels, which provides further evidence for the relationship between IBS and SIBO.

Example 14

Neural Regulation of the Rate of Upper Gastrointestinal Transit

The experiments described below are based on a previously described chronic multi-fistulated dog model, employing surgically fistulated male or female mongrel dogs weighing about 25 kg each. (Lin, H. C. et al., *Inhibition of gastric emptying by glucose depends on length of intestine exposed to nutrient*, Am. J. Physiol. 256:G404-G411 [1989]). The small intestines of the dogs were each about 300 cm long from the pylorus to the ileal-cecal valve. The duodenal fistula was situated 15 cm from the pylorus; the mid-gut fistula was situated 160 cm from the pylorus. Occluding Foley catheters (balloon catheters that are inflated to produce a water-tight seal with the lumenal surface) were plated into the distal limb of a duodenal fistula and a mid-gut fistula, fat or other test agents were administered lumenally to the thus compartmentalized "proximal" section of the gut, i.e., between the fistulas, or to the compartmentalized "distal"-section of the gut, i.e., beyond the mid-gut fistula. Perfusate was pumped into a test section through the catheter at a rate of 2 mL/minute. Test agents were administered along with buffer perfusate, but some test agents were administered intravenously, where specifically noted.

Intestinal transit measurements were made by tracking the movement of a liquid marker across the approximately 150 cm intestinal test segment by delivering about 20 µCi $^{99m}$Tc chelated to diethyltriamine pentaacetic acid (DTPA) (Cunningham, K. M. et al., *Use of technicium-99m (V)thiocyanate to measure gastric emptying of fat*, J. Nucl. Med. 32:878-881 [1991]) as a bolus into the test segment after 60 minutes of a 90-minute perfusion. The output from the mid-gut fistula was collected every 5 min thereafter for 30 minutes, which period is illustrated in FIGS. 9-23. Using a matched dose of $^{99m}$Tc to represent the original radioactivity (Johansson, C., *Studies of gastrointestinal interactions*, Scand. J. Gastroenterol. 9(Suppl 28): 1-60 [1974]; Zierler, K., *A simplified explanation of the theory of indicator dilution for measurement of fluid flow and volume and other distributive phenomena*, Bull. John Hopkins 103:199-217 [1958]), the radioactivity delivered into the animal as well as the radioactivity of the recovered fistula output were all measured using a gamma well counter. After correcting all counts to time zero, intestinal transit was calculated as the cumulative percent recovery of the delivered $^{99m}$Tc-DTPA. This method has been well validated over the years and appreciated for its advantage of minimal inadvertent marker loss. To demonstrate this point, we perfused phosphate buffer, pH7.0; through the proximal gut and followed the cumulative recovery of this marker (% recovery) over time (n=1). There was a very high level of marker recovery, with 90% of the marker recovered by 30 minutes and 98% of the marker recovered by 45 minutes.

(1) Slowing of Intestinal Transit by PYY Depends on Ondansetron-Sensitive 5-HT-Mediated Pathway.

Peptide YY (PYY) slows transit and is a signal for lumenal fat (Lin, H. C. et al., *Fat-induced ileal brake in the dog depends on peptide YY*, Gastroenterol. 110(5):1491-95 [1996b]; Lin, H. C. et al., *Slowing of intestinal transit by fat in proximal gut depends on peptide YY*, Neurogastroenterol. Motility 10:82 [1998]). Since serotonin (5-HT) can also be a signal for fat (Brown, N. J. et al., *The effect of a 5HT3 antagonist on the ileal brake mechanism in the rat*, J. Pharmacol. 43:517-19 [1991]; Brown, N. J. et al. [1993]), the hypothesis was tested that the slowing of transit by PYY can depend on a 5-HT-mediated pathway by comparing the rate of marker transit during the administration of PYY in the presence or absence of ondansetron (Ond; a 5-HT receptor antagonist) in the proximal versus distal gut (n=2 for each treatment).

Normal saline (0.15 M NaCl) or PYY (0.8 µg/kg/h) was administered intravenously over a 90 minute period, while phosphate buffer, pH 7.0, was perfused into the lumen of the proximal gut through the duodenal fistula at a rate of 2 mL/min for the 90 minutes and was recovered from the output of the mid-gut fistula. The results are summarized in FIG. 9. Transit was slowed by intravenous PYY, with recovery of the marker decreased from 75.1±3.6% (control: IV normal saline [NS]+lumenal normal saline, i.e., NS-NS in FIG. 9) to 17.1±11.0% (IV PYY+lumenal normal saline, i.e., PYY-NS in FIG. 9). This effect was abolished by adding the specific 5-HT3 receptor antagonist ondansetron (0.7 mg/kg/h) to the buffer introduced into the proximal gut so that recovery increased to 78.3±4.8% (IV PYY+lumenal Ond proximal, i.e., PYY-Ond in prox in FIG. 9) but not by ondansetron in the distal gut, which decreased recovery to 12.9±12.9% (IV PYY+Ond in Distal, i.e., PYY-Ond in Dist). These results imply that slowing of transit by PYY depended on a 5-HT-mediated pathway located in the segment of the small intestine where transit was measured.

(2) The Fat Induced Jejunal Brake Depends on an Ondansetron-Sensitive Serotonin (5-HT)-Mediated Pathway.

The hypothesis was tested that slowing of transit by fat depends on a serotonergic pathway by comparing intestinal transit during perfusion with buffer or oleate in the presence or absence of ondansetron, a 5-HT3 receptor antagonist, in the proximal gut (n=3 each treatment). Buffer or 60 mM oleate was perfused through the duodenal fistula into the lumen of the proximal gut for a 90-minute period, in the manner described in Example 14(1), along with a bolus of normal saline±ondansetron (0.7 mg/kg) at the start of transit measurement. The rate of intestinal transit was slowed by the presence of oleate (p<0.05) in an ondansetron-sensitive manner. (p<0.05). The results are summarized in FIG. 10.

Figure 10:
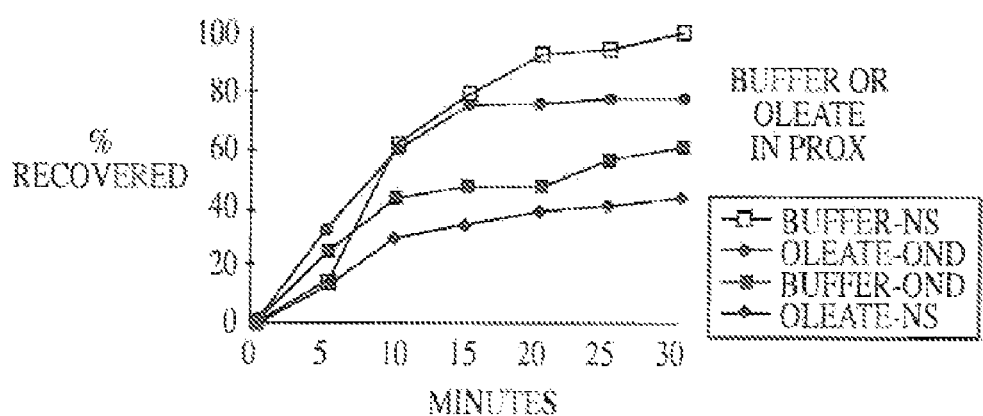
FIG. 10 demonstrates that demonstrates that slowing of the rate of intestinal transit by fat depends on a serotonergic pathway.

Specifically, ondansetron increased recovery of marker in the perfusate from 41.6±4.6% (mean±SE) (lumenal oleate+lumenal normal saline, i.e., Oleate-NS in FIG. 10) to 73.7±10.6% (lumenal oleate+lumenal ondansetron, i.e., Oleate-Ond in FIG. 10) during oleate perfusion but decreased recovery from 96.0±4.0% (lumenal phosphate buffer+lumenal normal saline, i.e., Buffer-NS in FIG. 10) to 57.9±15.9% (lumenal buffer+lumenal ondansetron, i.e., Buffer-Ond in FIG. 10) during buffer perfusion. These results imply that slowing of intestinal transit by the fat-induced jejunal brake and the acceleration of intestinal transit by buffer distension both depended on an ondansetron-sensitive 5-HT3-mediated pathway.

(3) The Fat-Induced Ileal Brake Depends on an Ondansetron-Sensitive, Efferent Serotonin (5-HT)-Mediated Pathway.

The fistulated dog model allows for the ileal brake (oleate in distal gut, buffer in proximal gut) to be separated into the afferent (distal) vs. efferent (proximal) limb of the response. Since 5-HT3 receptors are found on extrinsic primary sensory neurons (afferent limb) and on intrinsic 5-HT neurons of the myenteric plexus (5-HT interneuron) (efferent limb), the identification of the location of the 5-HT3 pathway (afferent vs. efferent limb) can localize the serotonergic pathway responsible for the slowing of transit by fat in the distal gut (ileal brake). Using occluding Foley catheters, the small intestine was compartmentalized into the proximal gut and the distal gut as described hereinabove. Intestinal transit was measured across the proximal gut (between fistulas) as described hereinabove. By perfusing buffer through the proximal gut while fat was perfused through the distal gut to trigger the fat-induced ileal brake, the distal gut represented the afferent limb of the response and the proximal gut represented the efferent limb of the response. To test for the location of the serotonergic pathway, 5-HT3 receptor antagonist ondansetron was then mixed with the appropriate-perfusate and adminstered into either the proximal or distal gut. Control=buffer in proximal and distal gut. Four dogs were tested.

Figure 11:
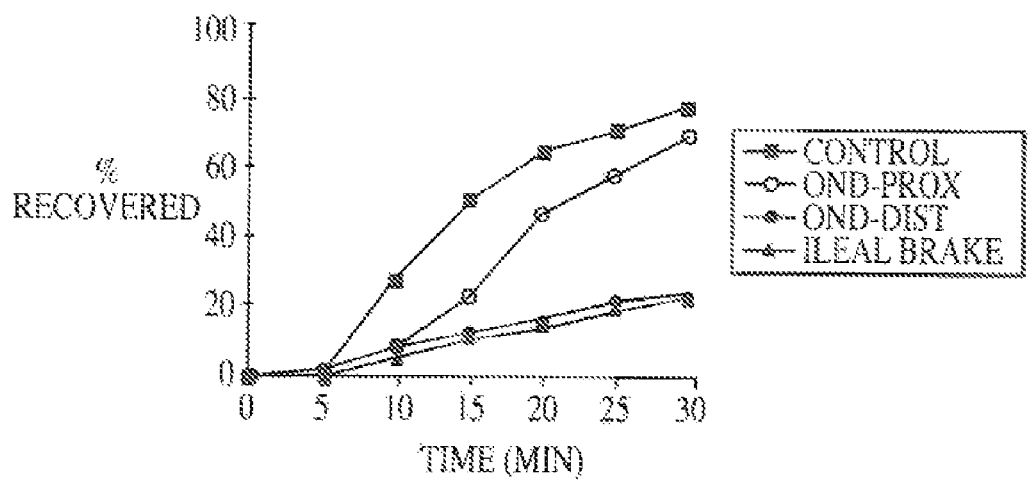
FIG. 11 illustrates that the fat induced ileal brake depends on an ondansetron-sensitive, efferent serotonergic 5-HT3-mediated pathway.

Delivering ondansetron lumenally into either the proximal or distal gut, intestinal transit was slowed by the ileal brake (76.3±3.1% [Control in FIG. 11] vs. 22.9±3.8% [Ileal Brake in FIG. 11]; p<0.005). But the ileal brake was abolished by ondansetron delivered to the proximal gut (68.5±2.7%; Ond in Prox in FIG. 11; n=4) but not distal gut (22.8±2.6%; Ond in Dist in FIG. 11; n=4).

Since ondansetron delivered with the fat in the distal gut had no effect, but ondansetron delivered with the buffer in the proximal gut abolished the ileal brake, the slowing of intestinal transit by fat in the distal gut depended on an ondansetron-sensitive, serotonergic pathway located on the efferent rather than afferent limb of the response. And since ondansetron abolished the jejunal brake in Example 14(2) when delivered with fat and abolished the ileal brake in Example 14(3) when delivered with buffer, this region-specific result cannot be explained by inactivation of drug by fat, differences in permeability or absorption.

(4) Ondansetron Abolishes the Fat-Induced Ileal Brake in a Dose-Dependent Manner.

The fat-induced ileal brake was abolished by the 5-HT receptor antagonist ondansetron in a dose-dependent manner. Perfusion of buffer was through both the duodenal and mid-gut fistulas (2 mL/min over 90 minutes); the buffer administered to the mid-gut fistula contained buffered normal saline (pH=7.0; Buffer Control in FIG. 12) or 60 mM oleate to induce the ileal brake response (Ileal Brake in FIG. 12). During the ileal brake response, ondansetron was added at to as a single bolus in the following doses (mg): 6.25; 12.5; and 25. Results are shown in FIG. 12.

Figure 12:
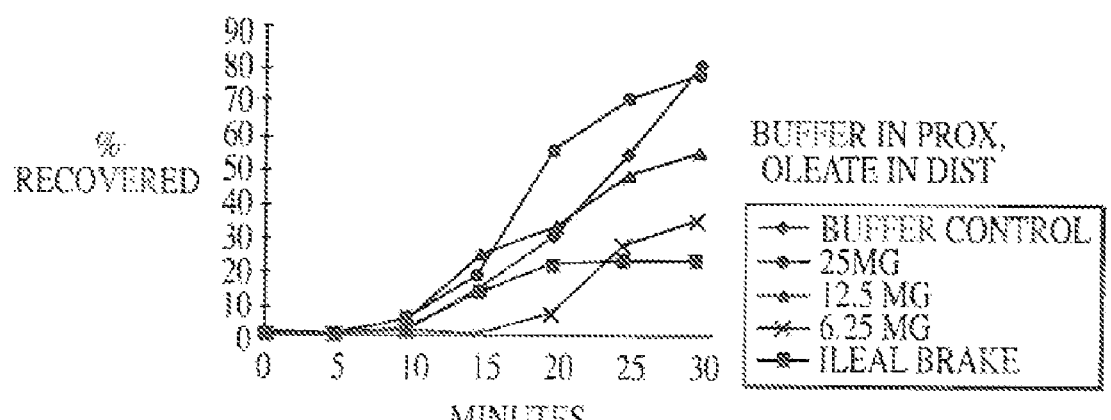
FIG. 12 shows that ondansetron abolishes the fat-induced ileal brake in a dose-dependent fashion.

Oleate induced the heal brake (24.1% marker recovery [Ileal brake in FIG. 12]vs. 81.2% marker recovery for the Buffer Control). The ileal brake was abolished by ondansetron delivered into the proximal gut in a dose-dependent manner (35.4% marker recovery at 6.25 mg ondansetron, 55.8% marker recovery at 12.5 mg-ondansetron, and 77.6% marker recovery at 25 mg ondansetron).

(5) Fat in the Distal Gut Causes the Release of 5-HT from the Proximal Gut.

To test the hypothesis that fat in the distal gut causes the release of 5-HT in the proximal gut, the amount of 5-HT collected from the output of the mid-gut fistula (proximal gut 5-HT) over a 90-minute period of buffer-perfusion through both the duodenal and mid-gut fistulas (2 mL/min); buffer (control) or oleate (60 mM) was administered to the distal gut (n=1). The amount of 5-HT was determined using an ELISA kit specific for 5-HT (Sigma, Graham-Smith, D. G., *The carcinoid syntome*, In: *Topics in Gastroenterology*, Truclove, S. C. and Lee, E. (eds.), Blackwells, London, p. 275 [1977]; Singh, S. M. et al., *Concentrations of serotonin in plasma—a test for appendicitis?*, Clin. Chem. 34:2572-2574 [1988]). The amount of 5-HT released by the proximal gut increased in response to fat in the distal gut from 100 μg in the control (buffer minus oleate) to 338 μg (buffer plus oleate to distal gut), showing that 5-HT is released in the proximal gut in response to fat in the distal gut. Thus, the release of 5-HT by the proximal gut can serve as a relayed signal for fat in the distal gut. The relayed release of 5-HT in the proximal gut in response to fat in the distal gut is consistent with Example 14(2), showing that slowing of intestinal transit by fat depends on an efferent 5-HT-mediated pathway to the proximal gut.

(6) Ondansetron Abolishes the Fat-Induced Ileal Brake when Administered Lumenally but not Intravenously.

To confirm that the reversal of the slowing of transit by ondansetron was peripheral, i.e., enteric, rather than systemic, the effect of ondansetron was compared when delivered luminally (through the duodenal fistula into the proximal gut) versus intravenously. Ondansetron was either delivered lumenally into the proximal gut (0.7 mg/kg/h; Ond in prox in FIG. 13) or administered intravenously (0.15 mg/kg/1.5 h; iv Ond in FIG. 13) during fat-induced ileal brake (60 mM oleate input through the mid-gut fistula into the distal gut as described above). Two dogs were tested (n=2).

Figure 13:
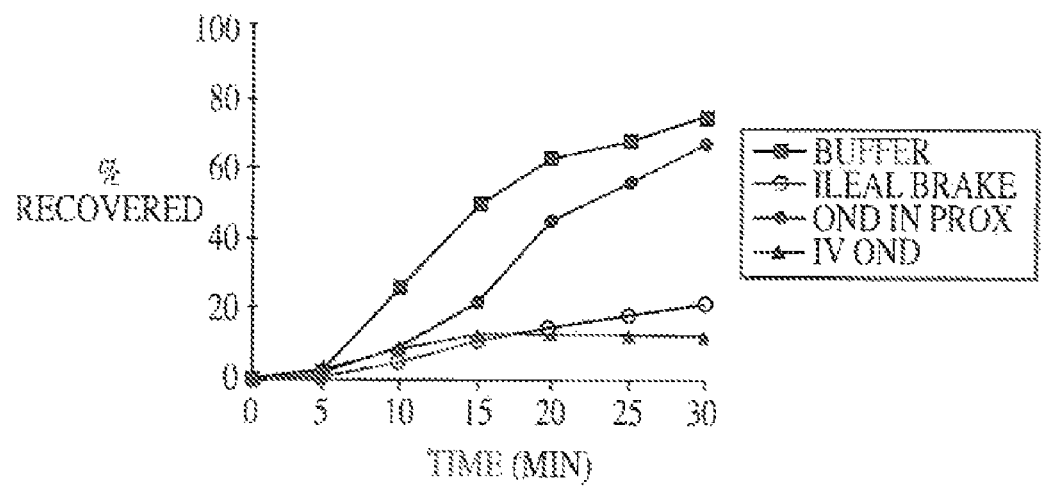
FIG. 13 shows that ondansetron abolishes the fat-induced ileal brake when administered luminally but not intravenously.

Results are shown in FIG. 13. Compared to the ileal brake (20±1.8% marker recovery), the marker recovery increased to 78±2.4% with lumenal ondansetron (p<0.005). Intravenous ondansetron had no substantial effect on the ileal brake (13±2.0% marker recovery). These results imply that the 5-HT3: receptor antagonist worked enterically rather than systemically.

(7) The Slowing of Intestinal Transit by Distal Gut 5-HT Depends on an Ondansetron-Sensitive 5-HT3-Mediated Pathway in the Proximal Gut (Efferent) and Distal Gut (Afferent).

To test the hypothesis that lumenal 5-HT may slow intestinal transit via 5-HT3 receptors similar to fat, 0.7 mg/kg ondansetron, a 5-HT3 receptor antagonist or buffered saline (pH 7.0) was delivered into either the proximal or distal gut as a bolus at the start of the transit measurement. Four dogs were tested.

Figure 14:
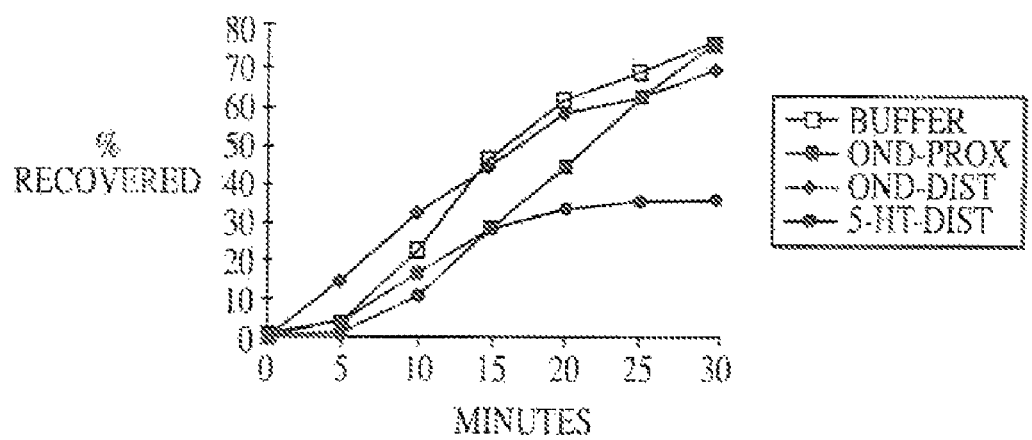
FIG. 14 illustrates that the slowing of intestinal transit by distal gut 5-HT depends on an ondansetron-sensitive 5-HT-mediated pathway in the proximal (efferent) and distal (afferent) gut.

Results are shown in FIG. 14. The slowing of intestinal transit by 5-HT (0.1 mg/kg/h) administered to the distal gut (35.2±2.2% marker recovery). (vs. 76.1±4.7% marker recovery for buffer control) was abolished by ondansetron added to the proximal or distal gut as shown by % marker recovery of 73.8±9.5% (Ond-Prox in FIG. 14) vs. 79.5±2.4% (Ond-Dist in FIG. 14), respectively (p<0.001).

This shows that in the conscious whole animal, the slowing of intestinal transit by luminal 5-HT depended on an ondansetron-sensitive serotonergic pathway located on both the afferent and efferent limb of the intestino-intestinal reflex. (See also, Brown, N. J. et al., *Granisetron and ondansetron: effects on the ileal brake mechanism, in the rat*, J. Pharm. Pharmacol. 45(6):521-24 [1993]). In contrast, the slowing of intestinal transit by distal gut fat (Example 14[3]) depended on a 5-HT3 pathway localized specifically on the efferent limb to suggest that 5-HT is not the stimulus for the afferent limb of the fat-induced ileal brake, but rather involves a signal other than 5-HT, such as PYY. However, 5-HT is the stimulus for the afferent limb of the slowing of intestinal transit by 5-HT in the distal gut.

(8a) 5-HT in the Distal Gut Slows Intestinal Transit in a Dose-Dependent Manner.

In a preliminary experiment, intestinal transit during buffer perfusion of both the proximal and distal guts (81.2% recovery) was slowed by 5-HT in distal gut so that marker recovery decreased to 73.8% at 2 mg 5-HT (0.033 mg 5-HT/kg/h), 53.1% at 3 mg (0.05 mg 5-HT/kg/h) and 11.6% at 4 mg (0.066 mg 5-HT/kg/h) dose over a 90 minute period (n=1).

The dose-dependent effect of 5-HT in slowing intestinal transit was confirmed in an additional experiment. The cumulative % recovery of the radioactive marker was reduced in a dose-dependent fashion as the 5-HT perfusion increased from 0 to 0.1 mg/kg/h to suggest that intestinal transit is slowed by lumenal 5-HT. However, the speed of transit was markedly accelerated when the 5-HT dose was increased to 0.3 mg/kg/h (Table 7).

TABLE 7

Effect of 5-HT delivered to distal gut on intestinal transit time (min) in multi-fistulated dogs (n = 2 dogs).

| 5-HT dose (mg/kg/h × 90 min) | | | | | |
|---|---|---|---|---|---|
| 0 | 0.033 | 0.05 | 0.066 | 0.1 | 0.3 |
| 68.5 ± 1.0 | 69.6 ± 4.2 | 33.5 ± 1.5 | 15.2 ± 0.5 | 16.1 ± 4.9 | 73.8 ± 0.6 |

(8b) Lumenal 5-HT, Delivered to the Proximal Gut Slows Intestinal Transit in a Dose-Dependent Fashion in the Conscious Whole Animal Model.

In in-vitro models, lumenal 5-HT applied to an isolated bowel loop accelerated transit by triggering the peristaltic reflex. In contrast, in the conscious whole animal model applied herein (with extrinsic nerves intact), 5-HT applied lumenally slowed intestinal transit (Example 14[8a] above). In further experiments, 5-HT was delivered at a rate of 0, 0.033, 0.066, 0.05 and 0.1 mg/kg/h into the proximal gut. Four dogs were tested.

Figure 15:
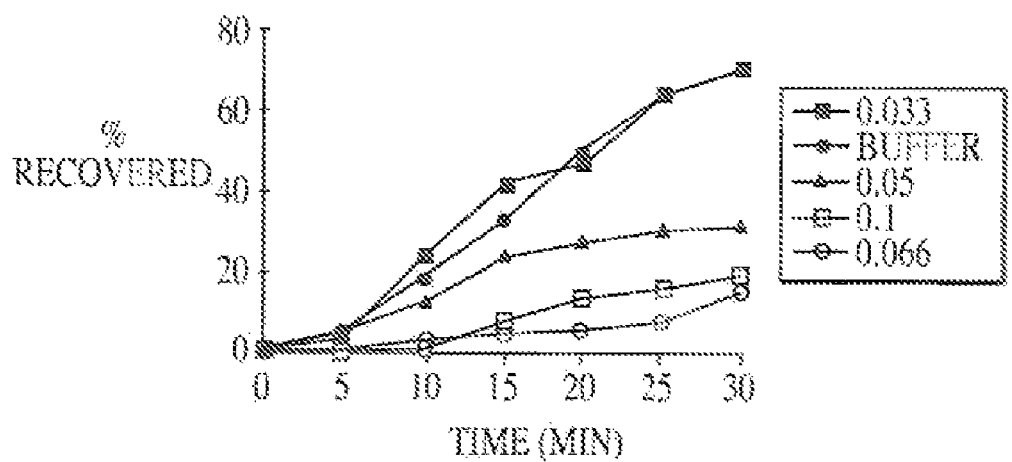
FIG. 15 shows that lumenal 5-HT, delivered to the proximal gut, slows intestinal transit in a dose-dependent fashion.

Results are shown in FIG. 15. Intestinal transit was significantly slowed by 5-HT in the proximal gut in a dose-dependent fashion ($p<0.00001$). Marker recovery during buffer perfusion was 75.0±4.4% while at the dose of 0.066 mg/kg/h marker recovery was reduced to 16.9±+3.7%, and was not significantly different from the dose of 0.1 mg/kg/h. At the intermediate dose of 0.05 mg/kg/h, marker recovery was 33.2±14.0%; buffer vs 0.05 mg/kg/h; $p<0.005$) and at the lowest dose of 0.033 mg/kg/h, marker recovery was not significantly different from the buffer control.

(8c) Slowing of Intestinal Transit by 5-HT is not Dependent on Volume of the Output of the Midgut Fistula.

5-HT stimulates small bowel and colonic secretion. We have observed a slowing effect of 5-HT on intestinal transit (Example 14[8a-b]). As a control, to determine whether intestinal transit correlates with volume of the output of the midgut fistula. Varying doses of 5-HT (0, 0.033, 0.1, 0.3 mg/kg/h) were perfused into the proximal gut, $^{99m}$Tc was delivered into the test segment as a bolus for transit measurement. The volume of the output of the midgut fistula was collected during the last 30 minutes of the 90 min perfusion experiment (n=21). Transit was plotted against output volume. There was no correlation between transit during 5-HT treatment and the volume of the output of the midgut fistula (data not shown).

Therefore, the observed transit effect of 5-HT cannot be explained solely on the basis of volume effect related to 5-HT induced intestinal secretion. The observed transit effect of 5-HT must depend on transit-specific regulation.

Together, the results in Example 14(8) and show that, contrary to the effect of 5-HT in an in-vitro model, lumenally administered 5-HT slows intestinal transit in a dose-dependent fashion in the conscious whole animal model, which implies that the slowing of intestinal transit depends on extrinsic nerves.

(9a) 5-HT in the Distal Gut Causes Release of 5-HT in the Proximal Gut.

To test the hypothesis that 5-HT in the distal gut causes the release of 5-HT in the proximal gut, the amount of 5-HT collected from the output at the mid-gut fistula (Proximal gut 5-HT) over a 90-minute period of buffer perfusion through both the duodenal and mid-gut fistulas (2 mL/min each) was compared in the presence or absence of 5-HT (0.05 mg/kg/h) administered to the distal gut (n=1). 5-HT concentration was determined using an ELISA kit specific for 5-HT (Sigma). The amount of 5-HT released by the proximal gut increased from 156 µg in the control (minus distal 5-HT) to 450 µg (plus 5-HT to distal gut), implying that 5-HT is released by the proximal gut in response to 5-HT in the distal gut. Thus, the release of 5-HT by the proximal gut can serve as a relayed signal for distal gut 5-HT. This relayed release of 5-HT in the proximal gut explains the results of Example 14(6) showing that the slowing of intestinal transit by distal gut 5-HT was abolished by ondansetron in the proximal gut (efferent limb of response) as well as in the distal gut (afferent limb of response).

(9b) Fat in Distal Gut Releases 5-HT from Proximal Gut.

To test the hypothesis that the proximal gut releases 5-HT in response to lipid in the distal gut, we compared the amount of 5-HT in the output of the midgut fistula (i.e., proximal gut 5-HT) with buffered saline (control) or oleate in the distal gut. The amount of 5-HT collected over 90 min was measured using a 5-HT-specific ELISA test kit, as described herein above. Four dogs were tested.

The amount of proximal gut 5-HT increased from 82.7±20.53 ng to 211.75±35.44 ng ($p<0.005$) when the distal gut perfusate was switched from buffer to oleate, implying that 5-HT is released from the proximal gut in response to fat in the distal gut, as a relayed signal for fat.

Fat is also a chemical trigger for the release of 5-HT, thus these results are consistent with the release of 5-HT via a long distance, intestino-intestinal communications, or reflex.

(9c) Luminal 5-HT Slows Intestinal Transit Via Activation of the Intestino-Intestinal Reflex.

To confirm that 5-HT, delivered lumenally, slowed intestinal transit via the activation of an intestino-intestinal reflex, we compared intestinal transit across the proximal one-half of gut while 0 (pH 7.0 buffered saline control) or 0.1 mg/kg/h of 5-HT was delivered into either the proximal or distal one-half of the gut. Four dogs were tested.

Figure 16:
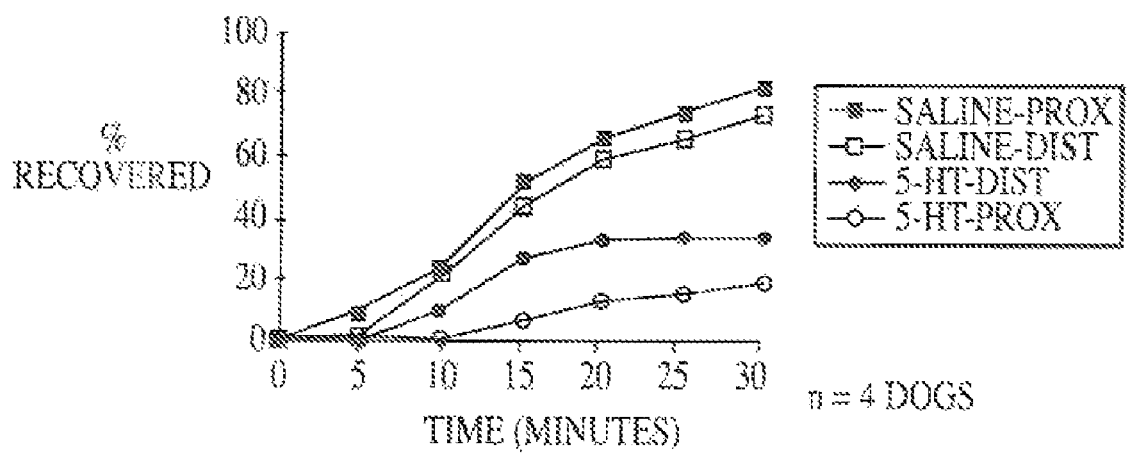
FIG. 16 illustrates that lumenal 5-HT slows intestinal transit via activation of an intestino-intestinal reflex.

Results are shown in FIG. 16. Intestinal transit across the proximal gut was slowed by 5-HT in either the proximal or distal gut, demonstrated by the marker recovery decreasing from 85.0±7.3% (Saline-Prox in FIG. 16) ($p<0:005$) to 20.1±4.5% for proximal gut 5-HT (5-HT-Prox in FIG. 16) and 76.1±1.3% (Saline-Dist in FIG. 16) to 35.2±2.3% (5-HT-Dist in FIG. 16) ($p<0.005$) for distal gut 5-HT.

These results imply that the slowing of intestinal transit by 5-HT depends on a long-distance, region-to-region reflex, since 5-HT administered into the distal gut slowed intestinal transit through the physically separate proximal gut.

(10) Intravenous PYY Causes Release of 5-HT in the Proximal Gut.

The amount of 5-HT released from the proximal gut in response to intravenous PYY or buffered saline (Control) during buffer perfusion (2 mL/min over 90 minutes) through both the duodenal and mid-gut fistulas was measured to test the hypothesis that intravenous PYY (0.8 mg/kg/h) causes the release of 5-HT in the proximal gut. 5-HT was measured as in Example 14(9) above. The amount of 5-HT released by the proximal gut increased from 140.1 µg (Control) to 463.1 µg in response to intravenous PYY.

This result was comparable with the response when 60 mM oleate was administered to the distal gut (buffer only to the proximal gut) during the perfusion without intravenous PYY (509.8 µg of 5-HT; n=1), which implies that the release of 5-HT in the proximal gut stimulated by fat in the distal gut can be mediated by PYY.

(11) Slowing of Intestinal Transit by Fat in the Distal Gut Depends on an Extrinsic Adrenergic Neural Pathway.

A distension-induced intestino-intestinal inhibitory neural reflex projects through the celiac prevertebral celiac ganglion via a cholinergic afferent and an adrenergic efferent (Szurszewski, J. H. and King, B. H., *Physiology of prevertebral ganglia in mammals with special reference to interior mesenteric* ganglion, In: *Handbook of Physiology: The Gastrointestinal System*, Schultz, S. G. et al. (eds.), American Physiological Society, distributed by Oxford University Press, pp. 519-592 [1989]). Intestinal transit was measured during fat perfusion of the distal small intestine in the presence or absence of intravenous propranolol (50 μg/kg/h; n=2 dogs), a 1-adrenoceptor antagonist, to test the hypothesis that the slowing of intestinal transit by fat in the distal gut also depends on an adrenergic pathway. Perfusion of buffer was through both the duodenal and mid-gut fistulas (2 mL/min over 90 minutes); the buffer administered to the mid-gut fistula contained 60 mM oleate. The results are illustrated in FIG. 17.

Figure 17:
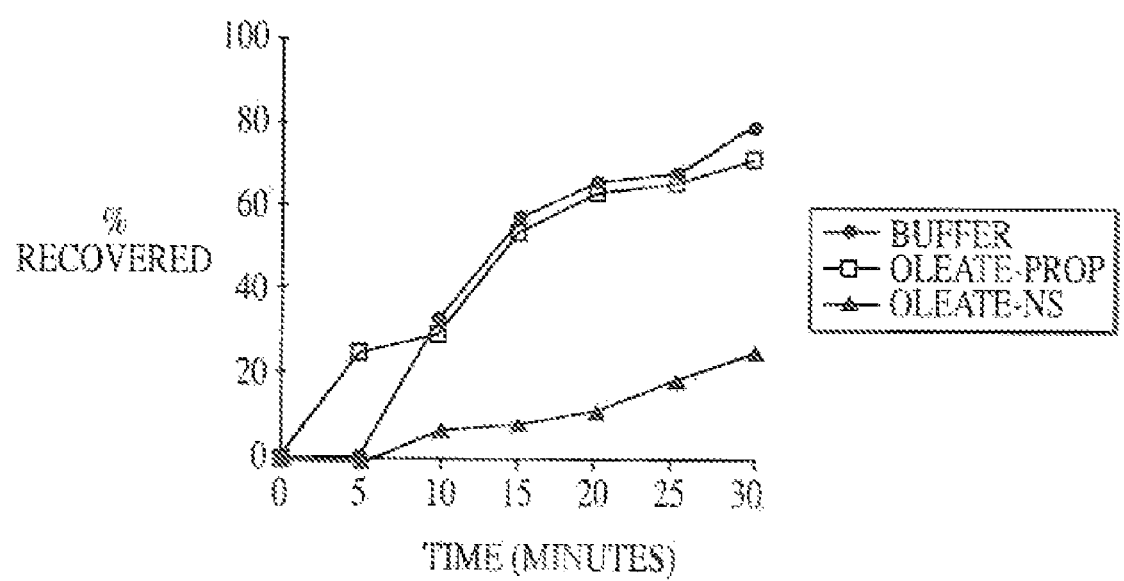
FIG. 17 illustrates that slowing of intestinal transit by distal gut fat depends on an extrinsic adrenergic neural pathway.
Figure 18:
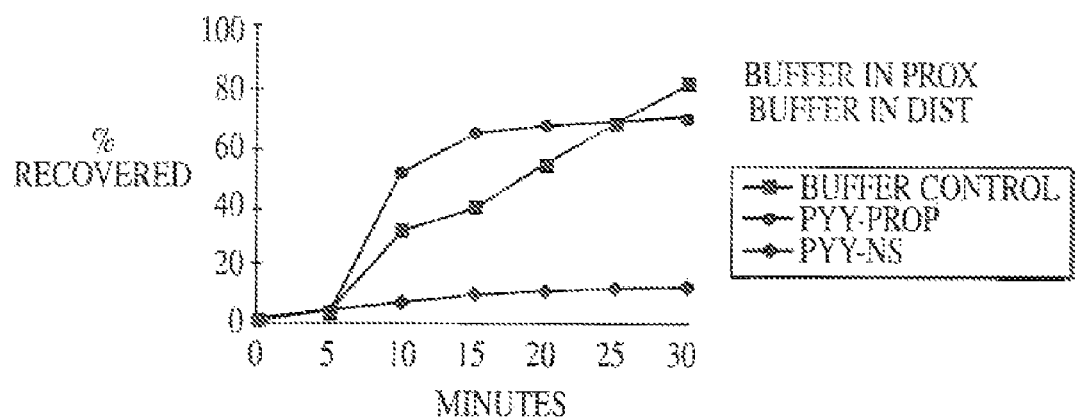
FIG. 18 illustrates that slowing of intestinal transit by PYY depends on an extrinsic adrenergic neural pathway.
Figure 19:
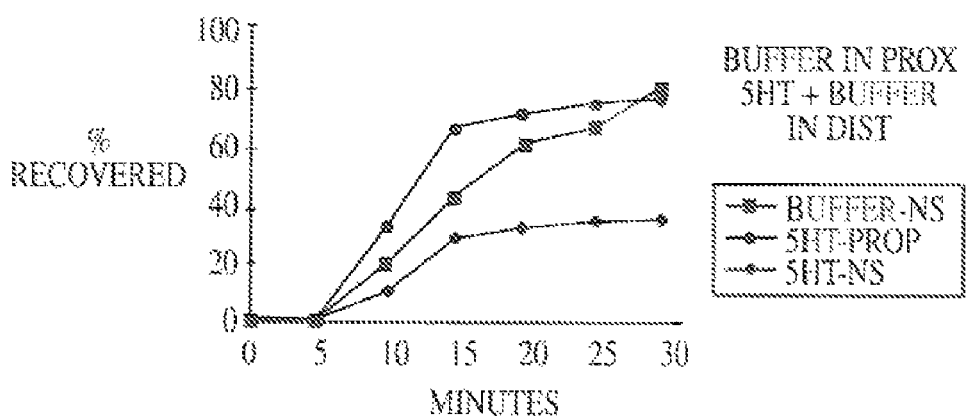
FIG. 19 illustrates that slowing of intestinal transit by 5-HT in the distal gut depends on a propranolol-sensitive extrinsic adrenergic neural pathway.

Intestinal transit was slowed by distal gut fat (79.7±5.8% marker recovery [Buffer Control in FIG. 17]compared to 25.8±5.2% recovery with fat perfusion into the distal gut [Oleate-NS in FIG. 17]). Intravenous propranolol abolished this jejunal brake effect so that recovery increased to 72.1±4.7% (oleate+propanolol, i.e., Oleate-Prop in FIG. 17), implying that the slowing of transit by fat in the distal gut depends on a propranolol-sensitive, adrenergic pathway. This result supports the hypothesis that the response to fat involves an adrenergic efferent, such as the extrinsic nerves projecting through the prevertebral ganglia.

(12) Slowing of Intestinal Transit by PYY Depends on an Extrinsic Adrenergic Neural Pathway.

Intestinal transit during buffer perfusion of the proximal and distal small intestine in the presence or absence of intravenous propranolol (50 μg/kg/h; n=2) was measured, to test the hypothesis that the slowing of intestinal transit by PYY (a fat: signal) also depends on an adrenergic pathway. Perfusion was through both fistulas as described in Example 14(11) except that oleate was not administered to the distal gut, and, instead, 30 μg PYY (0.8 mg/kg/h) was administered intravenously during the 90 minute perfusion period. The results are summarized in FIG. 18.

Slowing of intestinal transit by PYY (78.1±2.2% marker recovery minus PYY [Buffer Control in FIG. 18] vs. 11.8±5.4% recovery with intravenous PYY [PYY-NS in FIG. 18]) was abolished by intravenous propranolol. In the presence of propanolol, marker recovery increased to 66.3±3.1% (PYY-Prop in FIG. 18). This result, consistent with the results of Example 14(11), implies that the slowing of transit by PYY depends on a propranolol-sensitive, adrenergic pathway, which supports the hypothesis that the response to PYY involves an adrenergic efferent such as the extrinsic nerves projecting through the prevertebral ganglia.

(13) Slowing of Intestinal Transit by 5-HT in the Distal Gut Depends on a Propranolol-Sensitive Extrinsic Adrenergic Neural Pathway.

Intestinal transit during buffer perfusion of the proximal and distal small intestine in the presence or absence of intravenous propranolol (50 μg/kg/h; n=2) was measured, to test the hypothesis that the slowing of intestinal transit by 5-HT in the distal gut also depends on an adrenergic pathway. Buffer perfusion was through both fistulas as described in Example 14(12) except that 5-HT (0.05 mg/kg/h) was administered to the distal gut during the 90 minute perfusion period. The results are summarized in FIG. 19.

Slowing of intestinal transit by 5-HT (83.3±3.3% marker recovery minus 5-HT [Buffer Control in FIG. 19] vs. 36.1±2.3% recovery with administration of 5-HT to the distal gut [5-HT-NS in FIG. 19]) was abolished by intravenous propranolol. In the presence of propanolol, marker recovery increased to 77.7±7.6% (5-HT-Prop in FIG. 19). This result implies that the slowing of transit by 5-HT depends on a propranolol-sensitive, extrinsic adrenergic pathway, perhaps similar to that responsible for the response to distal gut fat.

Enterochromaffin cells of the intestinal mucosa and myenteric 5-HT neurons are innervated by adrenergic nerves. (Gershon M D, Sherman D L., *Noradrenergic innervation of serotoninergic neurons in the myenteric plexus*, J Comp Neurol. 1987 May 8; 259(2):193-210 [1987]). To test the hypothesis that the slowing of intestinal transit by distal gut fat (ileal brake) and 5-HT depended on an adrenergic pathway, five dogs: were equipped with duodenal (10 cm from the pylorus) and midgut (160 cm from the pylorus) fistulas as described above. Using occluding Foley catheters, the small intestine was compartmentalized into the proximal (between fistulas) and distal (beyond midgut fistula) one-half of gut. Buffer (pH 7.0) was perfused into the proximal gut while 60 mM oleate was perfused into the distal gut at 2 ml/min for 90 min. Intestinal transit across the proximal gut was compared during intravenous administration of 50 μg/kg/h propranolol or saline. In addition, the effect was also determined of 5-HT administered at 0.1 mg/kg/h on intestinal transit with and without i.v. propranolol. Intestinal transit (mean±SE) was measured by $^{99m}$Tc-DTPA marker recovery in the output of the midgut fistula during the last 30 min of the 90 min experiment. The cumulative % marker recovered was compared using ANOVA and additional analyses by paired t-test.

Results are shown in Table 8 below. Oleate (p<0.002) and 5-HT (p<0.005) perfused into the distal gut slowed transit through the proximal gut as compared to buffer control. The slowing of intestinal transit by distal gut fat or 5-HT was both abolished by iv propranolol (p<0.01). These results provide further evidence that the slowing of intestinal transit by distal gut fat or 5-HT depends on an adrenergic efferent nerve.

TABLE 8

Effect of 5-HT and propranolol on proximal intestinal transit.

| | i.v. Agent | |
|---|---|---|
| Perfusate | Saline (i.v.) | Propranolol (i.v.) |
| Buffer Control | 70.11 ± 6.51 | — |
| Oleate (Ileal brake) | 26.62 ± 5.36 | 66.42 ± 8.26 |
| 5-HT distal gut | 28.27 ± 5.03 | 63.85 ± 8.76 |

(14) Intestinal Transit is Slowed by Norepinephrine in a 5-HT-Mediated Neural Pathway.

Intestinal transit during buffer perfusion of the proximal and distal small intestine with intravenous norepinephrine (NE; adrenergic agent) in the presence or absence of the 5-HT receptor antagonist ondansetron was measured, to test the hypothesis that the slowing of intestinal transit also depends on an adrenergic efferent pathway. Perfusion of buffer was through both the duodenal and mid-gut fistulas (2 mL/min over 90 minutes); norepinephrine (0.12 μg/kg/h) was administered intravenously during the 90 minute perfusion period; and normal saline, with or without ondansetron (0.7 mg/kg/h; n=2) was administered in the perfusate to the proximal gut. The results are summarized in FIG. 20.

Figure 20:
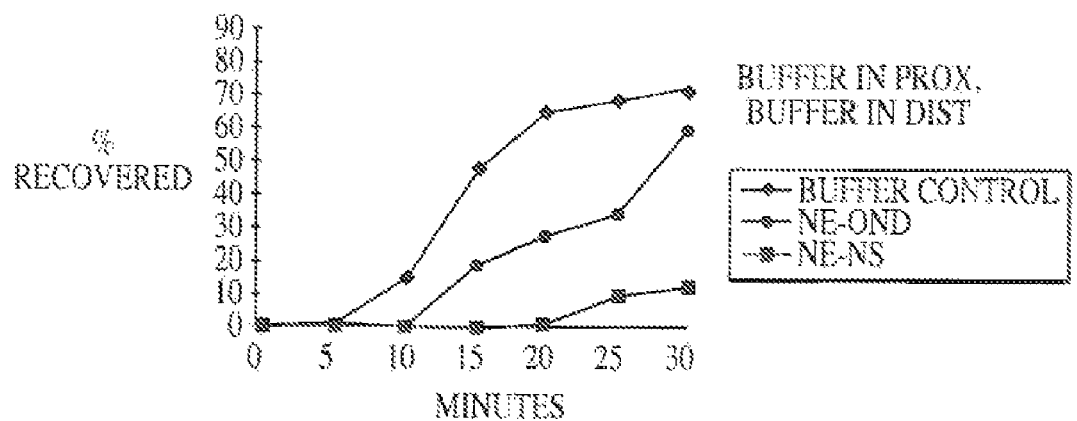
FIG. 20 illustrates that intestinal transit is slowed by norepinephrine (NE) in a 5-HT-mediated neural pathway.

Intestinal transit was slowed by NE so that marker recovery was reduced from 76.9% (Buffer Control in FIG. 20) to 13.3% (NE-NS in FIG. 20). Ondansetron abolished this slowing effect with marker recovery increased to 63.4% (NE-Ond in FIG. 20), to implies that NE (adrenergic efferent) slows transit via a 5-HT-mediated pathway. This result confirms that slowing of intestinal transit is mediated by an adrenergic efferent projecting from the prevertebral ganglion to the gut action on a 5-HT-mediated pathway.

To test the hypothesis that norepinephrine slows intestinal transit via 5-HT3 receptors, buffer transit across the proximal gut was compared during intravenous administration of norepinephrine with and without lumenally-perfused ondansetron. Five dogs were equipped with duodenal (10 cm from the pylorus) and midgut (160 cm from the pylorus) fistulas as described above. Using occluding Foley catheters, the small intestine was compartmentalized into the proximal (between fistulas) and distal (beyond midgut fistula) one-half of gut. Buffer (pH 7.0) was perfused into the proximal gut at 2 ml/min for 90 min. Intestinal transit of buffer across the proximal gut was compared during intravenous administration of 50 mg norepinephrine/30 ml/1.5 h with and without ondansetron perfused lumenally (0.7 mg/kg/h). Intestinal transit (mean±SE) was measured by $^{99m}$Tc-DTPA marker recovery in the output of the midgut fistula during the last 30 min of the 90 min experiment. The cumulative % marker recovered was compared using ANOVA and additional analyses by paired t-test.

Results are shown in Table 9 below. These results show that both an adrenergic and serotonergic pathways are involved in the slowing of intestinal transit.

TABLE 9

Effects of norepinephrine (NE) and ondansetron (Ond) on proximal intestinal transit.

| | Transit Across Proximal Gut (Cumulative % Marker Recovered) |
|---|---|
| Buffer Control | 68.5 ± 5.0$^a$ |
| Buffer + NE | 16.3 ± 3.4$^{ab}$ |
| Buffer + NE + Ond | 63.0 ± 4.4$^b$ |

$^a$p < 0.003
$^b$p < 0.0009

(15) The Fat-Induced Jejunal Brake Depends on the Slowing Effect of a Naloxone-Sensitive, Opioid Neural Pathway.

Figure 21:
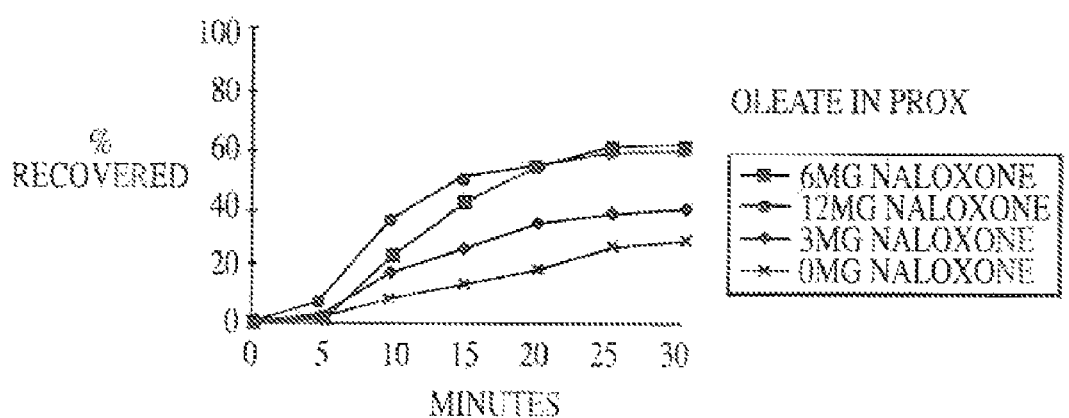
FIG. 21 illustrates that the fat-induced jejunal brake depends on the slowing effect of a naloxone-sensitive, opioid neural pathway.
Figure 22:
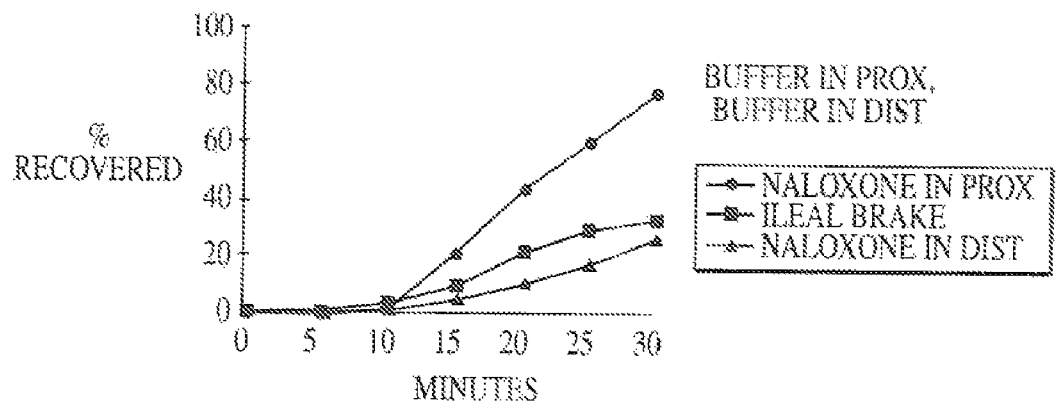
FIG. 22 illustrates that the fat-induced ileal brake-depends on the slowing effect of an efferent, naloxone-sensitive, opioid neural pathway.
Figure 23:
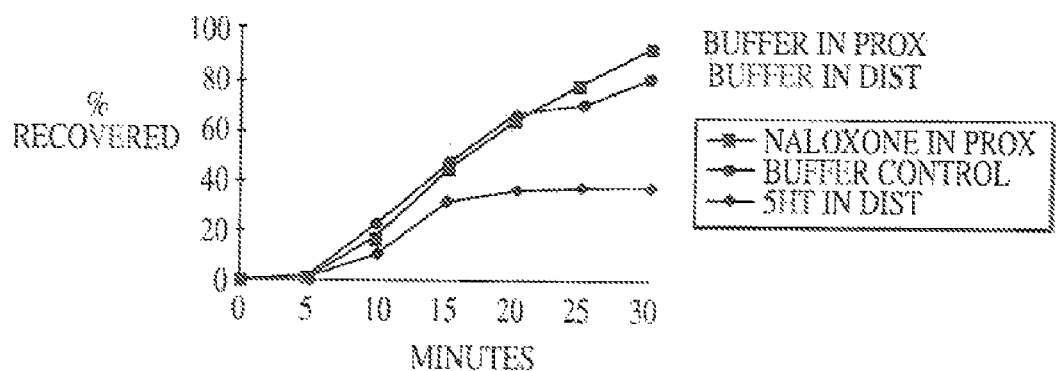
FIG. 23 shows that slowing of intestinal transit by distal gut 5-HT depends on a naloxone-sensitive, opioid neural pathway.

To test the hypothesis that the slowing of intestinal transit depended on an opioid pathway, the proximal gut was perfused (2 mL/minute for 90 minutes) with buffer containing 60 mM oleate and 0 (normal saline), 3, 6, or 12 mg of naloxone mixed therein, an opioid receptor antagonist. As shown in FIG. 21, the fat-induced jejunal brake response depended on the dose of naloxone mixed with the oleate (p<0.05, 1-way ANOVA) (n=7). Specifically, marker recovery was 30.0-3.6% with 0 mg naloxone, 41.0±5.2% with 3 mg naloxone, 62.8±8.2% with 6 mg naloxone and 60.6±6.1% with 12 mg naloxone. This result demonstrates that proximal gut fat slows intestinal transit via opioid pathway.

(16) The Effect of Naloxone was Specific for Fat-Triggered Feedback.

Intestinal transit was compared during perfusion of the proximal gut with buffer containing 0 (normal saline) or 6 mg naloxone (n=3). The rate of intestinal transit was not significantly affected by the opioid receptor antagonist naloxone when fat was not present in the proximal gut. Marker recovery was 88.0±1.3% with naloxone and 81.3±6.1% without naloxone. This implies that the accelerating effect of naloxone was specific for reversing the jejunal brake effect of fat.

(17) The Fat-Induced Ileal Brake Depends on the Slowing Effect of an Efferent, Naloxone-Sensitive, Opioid Neural Pathway.

The fistulated dog model allowed for the compartmentalization of the afferent limb (distal gut) from efferent limb (proximal gut) of the fat-induced deal brake. To test for the location of the opioid pathway involved in the slowing of transit by fat perfusion of buffer was through both the duodenal and mid-gut fistulas (2 mL/min over 90 minutes); the buffer administered through the mid-gut fistula to the distal gut contained 60 mM oleate to induce the ileal brake; 6 mg naloxone was delivered into either the proximal or distal gut (n=1). The results are summarized in FIG. 22.

Naloxone delivered to the proximal gut increased marker recovery from 34.6±4.8% to 76.2±5.2% (Naloxone in Prox in FIG. 21), but naloxone delivered to the distal gut had no effect on the ileal brake (marker recovery of 29.4±5.4% [Naloxone in Dist in FIG. 21]). This result implies that the fat-induced deal brake depends on an efferent, naloxone-sensitive opioid pathway, because an identical amount of naloxone was delivered into either of the two compartments, but the accelerating effect only occurred when naloxone was delivered into the efferent compartment. Therefore, an opioid pathway is involved that is located peripherally, rather than systemically. The accelerating effect in response to the opioid receptor antagonist is a result of the efferent location of the opioid pathway. It cannot be explained on the basis of chemical interaction with the perfusate, since the acceleration of transit was seen when naloxone was mixed with oleate in Example 14(15), as well as with buffer in this experiment.

(18) Mu and Kappa Opioid Antagonists Abolish Fat-Induced Ileal Brake.

The fat-induced deal brake (marker recovery 33.1%) was abolished by a mu antagonist (H2186, Sigma) delivered into the proximal gut so that marker recovery increased to 43.8% at 0.037 mg H2186, 88.2% at 0.05 mg H2186 and 66.8% at 0.1 mg H2186 over 90 minutes. A similar effect was seen when a kappa antagonist (H3116, Sigma) was used (marker recovery increased to 73.2% at 0.075 mg H3116, 90.9% at 0.1 mg H3116, and 61.8% at 0.125 mg H3116 over 90 minutes; n=1).

(19) Slowing of Intestinal Transit by Distal Gut 5-HT Depends on a Naloxone-Sensitive, Opioid Neural Pathway.

In Example 14(5), 5-HT in the distal gut slowed intestinal transit, similar to the effect of fat in the distal gut. Since the deal brake induced by fat in the distal gut was shown to depend on an efferent, naloxone-sensitive opioid pathway (Example 14(17), it was tested whether the slowing of intestinal transit in response to 5-HT in the distal gut also depends on an efferent, opioid pathway. Buffer, was perfused into both the proximal and distal guts at 2 mL/minute for 90 minutes. Either normal saline-(Buffer Control in FIG. 23) or 5-HT (0.05 mg/kg/h; 5-HT in Dist in FIG. 23) was administered to the distal gut over the 90 minute perfusion. When the perfusate to the distal gut contained 5-HT (i.e., 5-HT in Dist), naloxone (6 mg) was simultaneously delivered through the duodenal fistula to the proximal gut over the 90 minutes (Naloxone in Prox in FIG. 23). Results are summarized in FIG. 23.

First, intestinal transit was slowed by 5HT in the distal gut. Marker recovery was reduced from 79.4±4.1% (Buffer Control) to 37.0±1.8% (5-HT in Dist). Second, naloxone in proximal gut abolished this slowing effect with marker recovery increased to 90.1±4.6% (Naloxone in Prox). These results imply that slowed intestinal transit in response to 5-HT in the distal gut, depends on an efferent opioid pathway.

The foregoing examples being illustrative but not an exhaustive description of the embodiments of the present invention, the following claims are presented.

We claim:

1. A method of treating or reducing the recurrence of small intestinal bacterial overgrowth (SIBO) or a SIBO-caused condition in a human subject, comprising:
   providing a pharmaceutically acceptable composition comprising a serotonin receptor agonist; and
   administering the pharmaceutically acceptable composition to said human subject to treat or reduce the recurrence of small intestinal bacterial overgrowth (SIBO) or the SIBO-caused condition.

2. The method of claim 1, wherein the SIBO-caused condition is selected from the group consisting of irritable bowel syndrome, fibromyalgia, chronic pelvic pain syndrome, chronic fatigue syndrome, depression, impaired mentation, impaired memory, halitosis, tinnitus, sugar craving, autism, attention deficit/hyperactivity disorder, drug sensitivity, autoimmune disease, and Crohn's disease.

3. The method of claim 2, wherein the autoimmune disease is systemic lupus erythematous or multiple sclerosis.

4. The method of claim 1, wherein the SIBO-caused condition is irritable bowel syndrome.

5. The method of claim 1, wherein the serotonin receptor agonist is selected from the group consisting of prucalopride, HTF-919, R-093877, 2-[1(4-Piperonyl)piperazinyl]benzothiazole, 1-(4-Amino-5-chloro-2-methoxyphenyl)-3-[1-butyl-4-piperidinyl]-1-propanone, 1-(4-Amino-5-chloro-2-methoxyphenyl)-3-[1-2-methylsulphonylamino)ethyl-4-piperidinyl]-1-propanone, and combinations thereof.

6. The method of claim 1, wherein the serotonin receptor agonist is prucalopride.

7. The method of claim 1, wherein the pharmaceutically acceptable composition is administered by an oral or enteral delivery route.

8. The method of claim 7, wherein the oral delivery route is by ingestion of coated or uncoated microspheres or particles, of a dispersible powder or granule formulation, of a suspension, emulsion, solution, syrup, or elixir, or of a coated or uncoated tablet, troche, capsule, caplet, or lozenge.

9. A method of treating or reducing the recurrence of irritable bowel syndrome in a human subject, comprising:
providing a pharmaceutically acceptable composition comprising prucalopride; and
administering the pharmaceutically acceptable composition to said human subject to treat or reduce the recurrence of irritable bowel syndrome.

10. The method of claim 9, wherein the pharmaceutically acceptable composition is administered by an oral or enteral delivery route.

11. The method of claim 10, wherein the oral delivery route is by ingestion of coated or uncoated microspheres or particles, of a dispersible powder or granule formulation, of a suspension, emulsion, solution, syrup, or elixir, or of a coated or uncoated tablet, troche, capsule, caplet, or lozenge.

12. A method of treating or reducing the recurrence of small intestinal bacterial overgrowth (SIBO) in a human subject, comprising:
providing a pharmaceutically acceptable composition comprising a serotonin receptor agonist; and
administering the pharmaceutically acceptable composition to said human subject to treat or reduce the recurrence of small intestinal bacterial overgrowth (SIBO).

13. The method of claim 12, wherein the serotonin receptor agonist is selected from the group consisting of prucalopride, HTF-919, R-093877, 2-[1-(4-Piperonyl)piperazinyl]benzothiazole, 1-(4-Amino-5-chloro-2-methoxyphenyl)-3-[1-butyl-4-piperidinyl]-1-propanone, 1-(4-Amino-5-chloro-2-methoxyphenyl)-3-[1-2-methylsulphonylamino)ethyl-4-piperidinyl]-1-propanone, and combinations thereof.

14. The method of claim 12, wherein the serotonin receptor agonist is prucalopride.

15. The method of claim 12, wherein the pharmaceutically acceptable composition is administered by an oral or enteral delivery route.

16. The method of claim 15, wherein the oral delivery route is by ingestion of coated or uncoated microspheres or particles, of a dispersible powder or granule formulation, of a suspension, emulsion, solution, syrup, or elixir, or of a coated or uncoated tablet, troche, capsule, caplet, or lozenge.

* * * * *